US012780920B2

(12) United States Patent
Fioretos et al.

(10) Patent No.: US 12,780,920 B2
(45) Date of Patent: Nov. 3, 2026

(54) AGENTS AND USES THEREOF

(71) Applicant: Lead Biologics International AB, Lund (SE)

(72) Inventors: Thoas Fioretos, Lund (SE); Niklas Landberg, Malmo (SE); Carl Sanden, Lund (SE)

(73) Assignee: Lead Biologics International AB, Lund (SE)

( * ) Notice: Subject to any disclaimer, the term of this patent is extended or adjusted under 35 U.S.C. 154(b) by 931 days.

(21) Appl. No.: 17/782,526

(22) PCT Filed: Dec. 7, 2020

(86) PCT No.: PCT/EP2020/084893
§ 371 (c)(1),
(2) Date: Jun. 3, 2022

(87) PCT Pub. No.: WO2021/111005
PCT Pub. Date: Jun. 10, 2021

(65) Prior Publication Data

US 2023/0092356 A1 Mar. 23, 2023

(30) Foreign Application Priority Data

Dec. 6, 2019 (SE) .................................... 1951413-2

(51) Int. Cl.
*A61P 35/02* (2006.01)
*C07K 16/28* (2006.01)
*A61K 39/00* (2006.01)

(52) U.S. Cl.
CPC .......... *C07K 16/2806* (2013.01); *A61P 35/02* (2018.01); *A61K 2039/505* (2013.01); *C07K 2317/732* (2013.01)

(58) Field of Classification Search
CPC .......... C07K 16/2806; C07K 2317/732; C07K 16/2803; A61P 35/02; A61K 2039/505
USPC ....................................................... 424/141.1
See application file for complete search history.

(56) References Cited

FOREIGN PATENT DOCUMENTS

| | | |
|---|---|---|
| WO | WO 2006/110581 | 10/2006 |
| WO | WO 2008/027739 | 3/2008 |
| WO | WO 2009/091547 A1 | 7/2009 |
| WO | WO 2014/100740 | 6/2014 |
| WO | WO 2017/004330 | 1/2017 |
| WO | WO 2017/160954 | 9/2017 |
| WO | WO 2019/155474 | 8/2019 |

OTHER PUBLICATIONS

Appelbaum and Bernstein., "Gemtuzumab ozogamicin for acute myeloid leukemia", *Blood*, 130(22):2373-2376, 2017.

Askmyr et al., "Selective killing of candidate AML stem cells by antibody targeting of IL1RAP", *Blood*, 121(18):3709-3713, 2013.

Baglaenko et al., "Invariant NKT Cell Activation Is Potentiated by Homotypic trans-Ly108 Interactions", *The Journal of Immunology*, 198(10): 3949-3962, 2017.

Barreyro et al., "Overexpression of IL-1 receptor accessory protein in stem and progenitor cells and outcome correlation in AML and MDS", *Blood*, 120(6):1290-1299, 2012.

Beltra et al., "Developmental Relationships of Four Exhausted CD8+ T Cell Subsets Reveals Underlying Transcriptional and Epigenetic Landscape Control Mechanisms", *Immunity*, 52:825-841, 2020.

Calpe et al., "The SLAM and SAP Gene Families Control Innate and Adaptive Immune Responses", *Advances in Immunology*, 97: 177-250, 2008.

Cancer Genome Atlas Research Network. "Genomic and epigenomic landscapes of adult de novo acute myeloid leukemia." *New England Journal of Medicine*, 368 (22): 2059-2074, 2013.

Cao et al., "NTB-A Receptor Crystal Structure: Insights into Homophilic Interactions in the Signaling Lymphocytic Activation Molecule Receptor Family", *Immunity*, 25: 559-570, 2006.

Collins et al., "Elotuzumab directly enhances NK cell cytotoxicity against myeloma via CS1 ligation: evidence for augmented NK cell function complementing ADCC", *Cancer Immunol Immunother.*, 62(12): 1841-1849, 2013.

Cowan et al., "Antibody-based therapy of acute myeloid leukemia with gemtuzumab ozogamicin", *Front Biosci* (Landmark Ed)., 18: 1311-1334, 2013.

Dimopoulos et al., "Elotuzumab plus Pomalidomide and Dexamethasone for Multiple Myeloma", *N engl J med.*, 379(19):1811-1822, 2018.

Döhner et al., "Diagnosis and management of AML in adults: 2017 ELN recommendations from an international expert panel", *Blood*, 129(4):424-447, 2017.

Dombret and Gardin., "An update of current treatments for adult acute myeloid leukemia", *Blood*, 127(1):53-61, 2016.

Dourado et al., "Endoglin: a novel target for therapeutic intervention in acute leukemias revealed in xenograft mouse models", *Blood*, 129(18):2526-2536, 2017.

Dragovich and Mor., "The SLAM family receptors: Potential therapeutic targets for inflammatory and autoimmune diseases", *Autoimmunity Reviews*, 17 :674-682, 2018.

Dragovich et al., "SLAMF6 clustering is required to augment T cell activation", *Plos One*, 14 (6): e0218109, 2019.

(Continued)

*Primary Examiner* — Yan Xiao
(74) *Attorney, Agent, or Firm* — pH IP Law

(57) ABSTRACT

The present invention provides agents comprising or consisting of a binding moiety with specificity for Signaling Lymphocytic Activating Molecule Family Member 6 (SLAMF6) for use in inducing cell death and/or inhibiting the growth and/or proliferation of pathological stem cells and/or progenitor cells associated with a neoplastic hematologic disorder, wherein the cells express SLAMF6 and/or modulating their interactions with immune cells that may also express SLAMF6. A related aspect of the invention provides agents comprising or consisting of a binding moiety with specificity for SLAMF6 for use in detecting pathological stem cells, progenitor cells and/or immune cells associated with a neoplastic hematologic disorder, wherein the cells express SLAMF6. Further provided are pharmacological compositions comprising the agents of the invention and methods of using the same.

9 Claims, 25 Drawing Sheets

(56) References Cited

OTHER PUBLICATIONS

Figure 1:
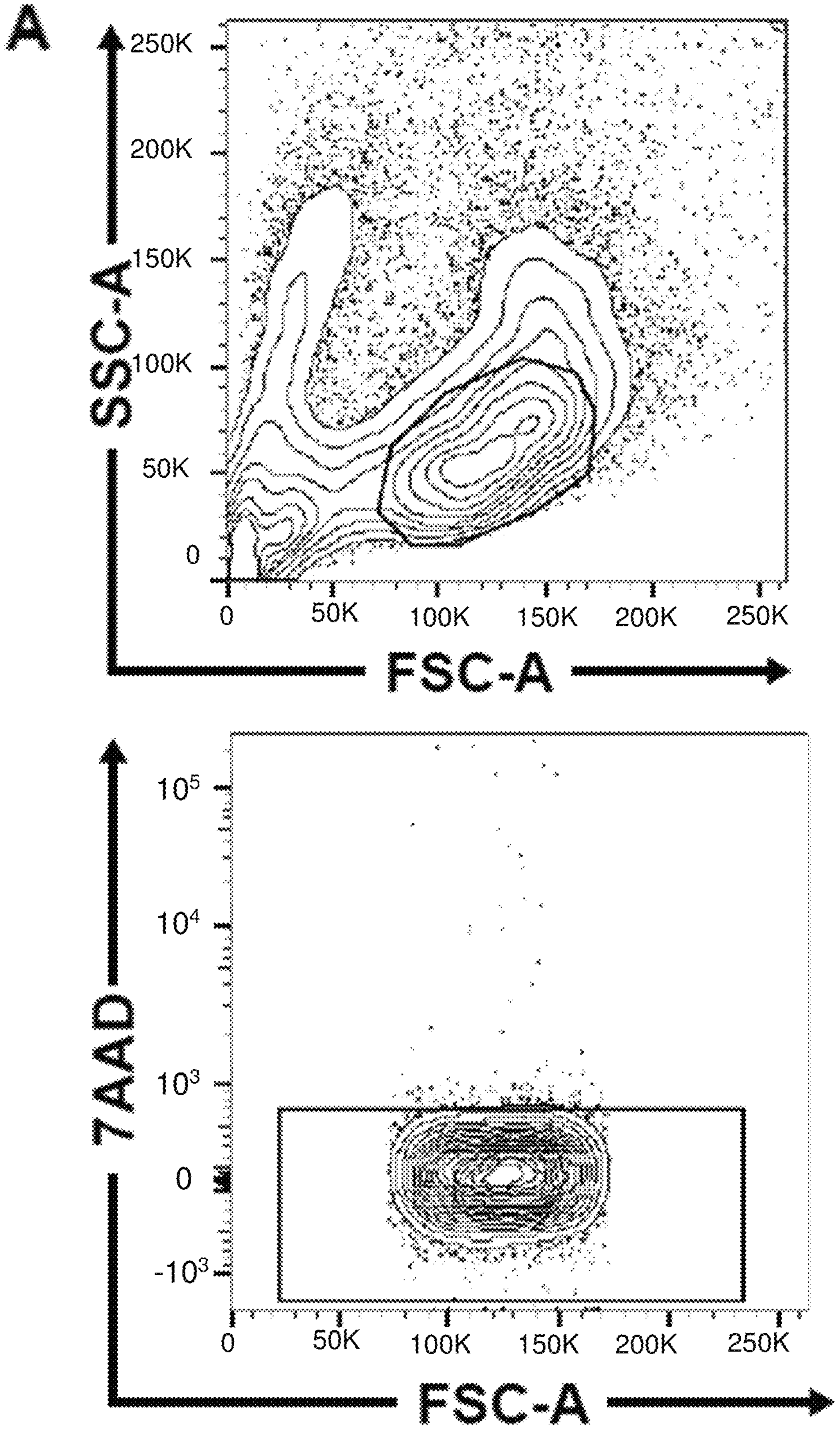

Eisenberg et al., Soluble SLAMF6 Receptor Induces Strong CD8p T-cell Effector Function and Improves Anti-Melanoma Activity In Vivo, *Cancer immunology research*, 6 (2): 127-138, 2018.
Eissmann et al., "Molecular Analysis of NTB-A Signaling: A Role for EAT-2 in NTB-A-Mediated Activation of Human NK Cells", *The Journal of Immunology*, 177 (5): 3170-3177, 2006.
Estey et al., "Acute myeloid leukemia: 2019 update on risk-stratification and Management", *Am J Hematol*., 93:1267-1291, 2018.
Farrell et al., "p53 is frequently mutated in Burkitt's lymphoma cell lines", *The EMBO Journal*, 10(10):2879-2887, 1991.
Flaig et al., "Cutting Edge: NTB-A Activates NK Cells via Homophilic Interaction", *The Journal of Immunology*, 172(11): 6524-6527, 2004.
Fouquet et al., "Signaling lymphocytic activation molecules Slam and cancers: friends or foes?", *Oncotarget*, 9(22): 16248-16262, 2018.
Gal et al., "Gene expression profiles of AML derived stem cells; similarity to hematopoietic stem cells", *Leukemia*, 20: 2147-2154, 2006.
Griewank et al., "Homotypic Interactions Mediated by Slamf1 and Slamf6 Receptors Control NKT Cell Lineage Development", *Immunity*, 27:751-762, 2007.
Hajaj et al., "Alternative splicing of SLAMF6 in human T cells creates a co-stimulatory isoform that counteracts the inhibitory effect of the full-length receptor", *bioRxiv*, 2020.
Hajaj et al., "Alternative Splicing of the Inhibitory Immune Checkpoint Receptor SLAMF6 Generates a Dominant Positive Form, Boosting T-cell Effector Functions", *Cancer immunology research*, 9(6): 637-650, 2021.
Hajaj et al., "SLAMF6 deficiency augments tumor killing and skews toward an effector phenotype revealing it as a novel T cell checkpoint", *eLife*, 9:e52539, 2020.
Howie et al., "Cutting Edge: The SLAM Family Receptor Ly108 Controls T Cell and Neutrophil Functions", *The Journal of Immunology*, 174(10): 5931-5935, 2005.
Humbel et al., "SLAMF Receptor Expression Identifies an Immune Signature that Characterizes Systemic Lupus Erythematosus", *Frontiers in Immunology*, 13(843059): 1-13, 2022.
Iwasaki et al., "CD93 marks a non-quiescent human leukemia stem cell population and is required for development of MLL-rearranged acute myeloid leukemia", *Cell Stem Cell*, 17(4): 412-421, 2015.
Jin et al., "Monoclonal Antibody-Mediated Targeting of CD123, IL-3 Receptor alpha Chain, Eliminates Human Acute Myeloid Leukemic Stem Cells", *Cell Stem Cell*, 5:31-42, 2009.
Jordan et al., "The interleukin-3 receptor alpha chain is a unique marker for human acute myelogenous leukemia stem cells", *Leukemia*, 14, 1777-1784, 2000.
Kageyama et al., "The Receptor Ly108 Functions as a SAP Adaptor-Dependent On-Off Switch for T Cell Help to B Cells and NKT Cell Development", *Immunity*, 36: 986-1002, 2012.
Kikushige et al., "TIM-3 Is a Promising Target to Selectively Kill Acute Myeloid Leukemia Stem Cells", *Cell Stem Cell*, 7: 708-717, 2010.
Korver et al., "The lymphoid cell surface receptor NTB-A: a novel monoclonal antibody target for leukaemia and lymphoma therapeutics", *British Journal of Haematology*, 137:307-318, 2007.
Lewis et al., "Abstract 1195: SGN-CD352A: A novel humanized anti-CD352 antibody-drug conjugate for the treatment of multiple myeloma", *Cancer Res*., 76 (14_Supplement) : 1195, 2016.
Li et al., "SLAMF3 and SLAMF4 are immune checkpoints that constrain macrophage phagocytosis of hematopoietic tumors", *Sci. Immunol*., 7: eabj5501, 2022.
Lu et al., "SLAM receptors foster iNKT cell development by reducing TCR signal strength after positive selection", *Nature Immunology*, 20: 447-457, 2019.
Majeti et al., "CD47 is an adverse prognostic factor and therapeutic antibody target on human acute myeloid leukemia stem cells", *Cell*, 138(2): 286-299, 2009.
Meng et al., "SLAMF6/Ly108 promotes the development of hepatocellular carcinoma via facilitating macrophage M2 polarization", *Oncology Letters*, 23(83):1-13, 2022.
Miller et al., "Subsets of exhausted CD8+ T cells differentially mediate tumor control and respond to checkpoint blockade", *Nature Immunology*, 326(20): 326-336, 2019.
Munitz et al., "2B4 (CD244) Is Expressed and Functional on Human Eosinophils", *The Journal of Immunology*, 174(1): 110-118, 2005.
Oguro et al., "SLAM Family Markers Resolve Functionally Distinct Subpopulations of Hematopoietic Stem Cells and Multipotent Progenitors", *Cell Stem Cell*, 13:102-116, 2013.
Pérez-Carmona et al., "Signaling Lymphocytic Activation Molecule Family Receptor Homologs in New World Monkey Cytomegaloviruses", *Journal of Virology*, 89(22): 11323-11336, 2015.
Pollyea et al., "Targeting acute myeloid leukemia stem cells: a review and principles for the development of clinical trials", haematologica, 99 (8): 1277-1284, 2014.
Radhakrishnan et al., "Novel anti-myeloma immunotherapies targeting the SLAM family of receptors", *Oncoimmunology*, 6(5):e1308618, 2017.
Sasca et al., "NCAM1 (CD56) promotes leukemogenesis and confers drug resistance in AML", *Blood*, 133(21):2305-2320, 2019.
Saxena et al., "Biologic and Clinical Significance of CD7 Expression in Acute Myeloid Leukemia", *American Journal of Hematology*, 58:278-284, 1998.
Schenkel et al., "Conventional type I dendritic cells maintain a reservoir of proliferative tumor-antigen specific TCF-1+ CD8+ T cells in tumor-draining lymph nodes", *Immunity*, 54:1-16, 2021.
Stein and Tallman., "Emerging therapeutic drugs for AML", *Blood*, 217(1):71-79, 2016.
Stengel et al., "The impact of TP53 mutations and TP53 deletions on survival varies between AML, ALL, MDS and CLL: an analysis of 3307 cases", *Leukemia*, 31: 705-711, 2017.
Tai et al., "Anti-CS1 humanized monoclonal antibody HuLuc63 inhibits myeloma cell adhesion and induces antibody-dependent cellular cytotoxicity in the bone marrow milieu", *Blood*, 112(4):1329-1338, 2008.
Testa et al., "CD123 as a Therapeutic Target in the Treatment of Hematological Malignancies", *Cancers*, 11: 1358, 2019.
Thomas and Majeti., "Biology and relevance of human acute myeloid leukemia stem cells", *Blood*, 129 (12): 1577-1585, 2017.
Uzana et al., "Trogocytosis Is a Gateway to Characterize Functional Diversity in Melanoma-Specific CD8+ T Cell Clones", *The Journal of Immunology*, 188(2): 632-640, 2012.
Valdez et al., "NTB-A, a new activating receptor in T cells that regulates autoimmune disease." *Journal of Biological Chemistry*, 279 (18): 18662-18669, 2004.
Van Rhenen et al., "The novel AML stem cell-associated antigen CLL-1 aids in discrimination between normal and leukemic stem cells", Blood, 110(7):2659-2666, 2007.
Wang et al., "Negative regulation of humoral immunity due to interplay between the SLAMF1, SLAMF5, and SLAMF6 receptors", *Frontiers in immunology*, 6 (158): 1-13, 2015.
Wang et al., "Slamf6 negatively regulates autoimmunity", *Clinical Immunology*, 173: 19-26, 2016.
Wu et al., "A hematopoietic cell-driven mechanism involving SLAMF6 receptor, SAP adaptors and SHP-1 phosphatase regulates NK cell education", *Nature Immunology*, 17(4):387-398, 2016.
Yigit et al., "SLAMF6 in health and disease: Implications for therapeutic targeting", *Clinical Immunology*, 204: 3-13, 2019.
Yigit et al., "A combination of an anti-SLAMF6 antibody and ibrutinib efficiently abrogates expansion of chronic lymphocytic leukemia cells", *Oncotarget*, 7(18):26346-26360, 2016.

FIG. 1-cont.
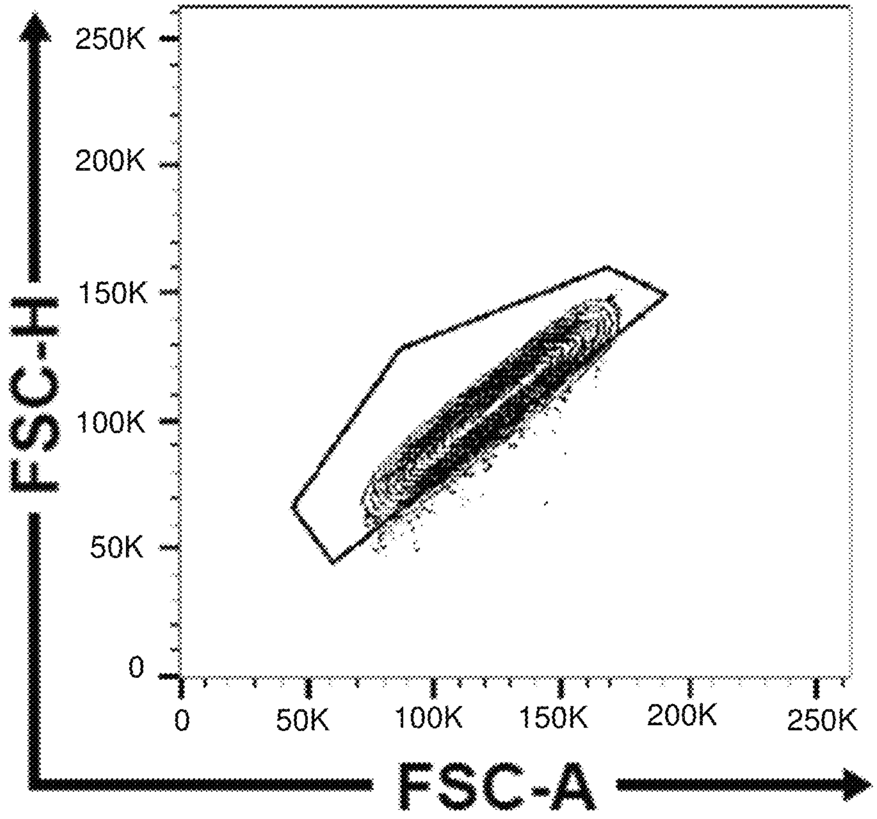
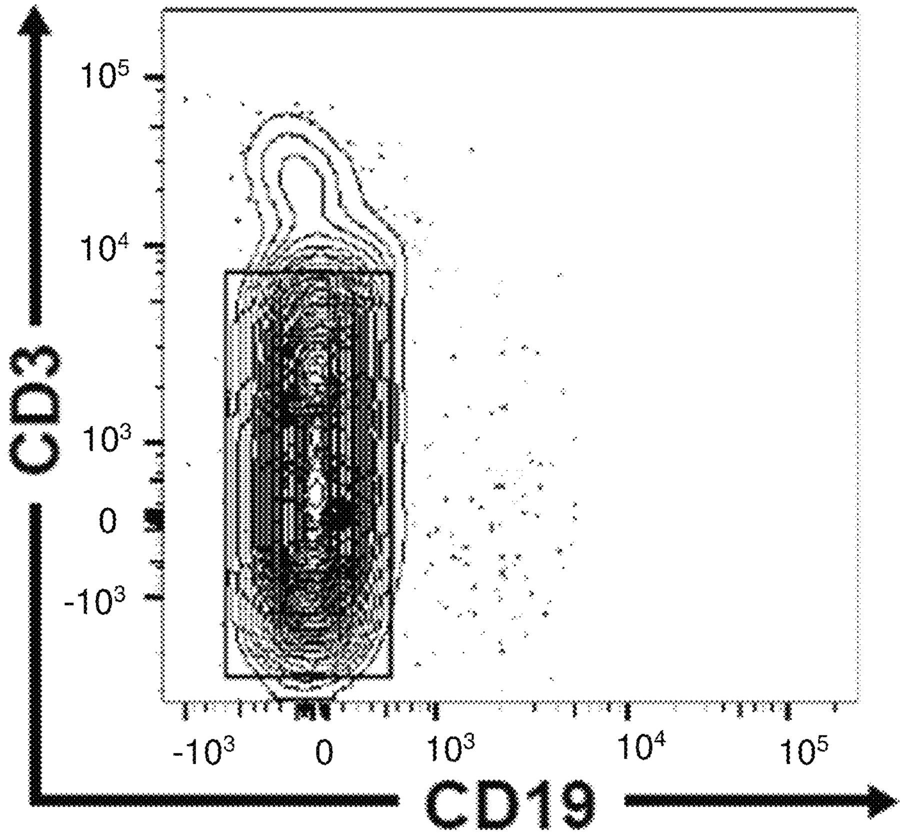

FIG. 1-cont.
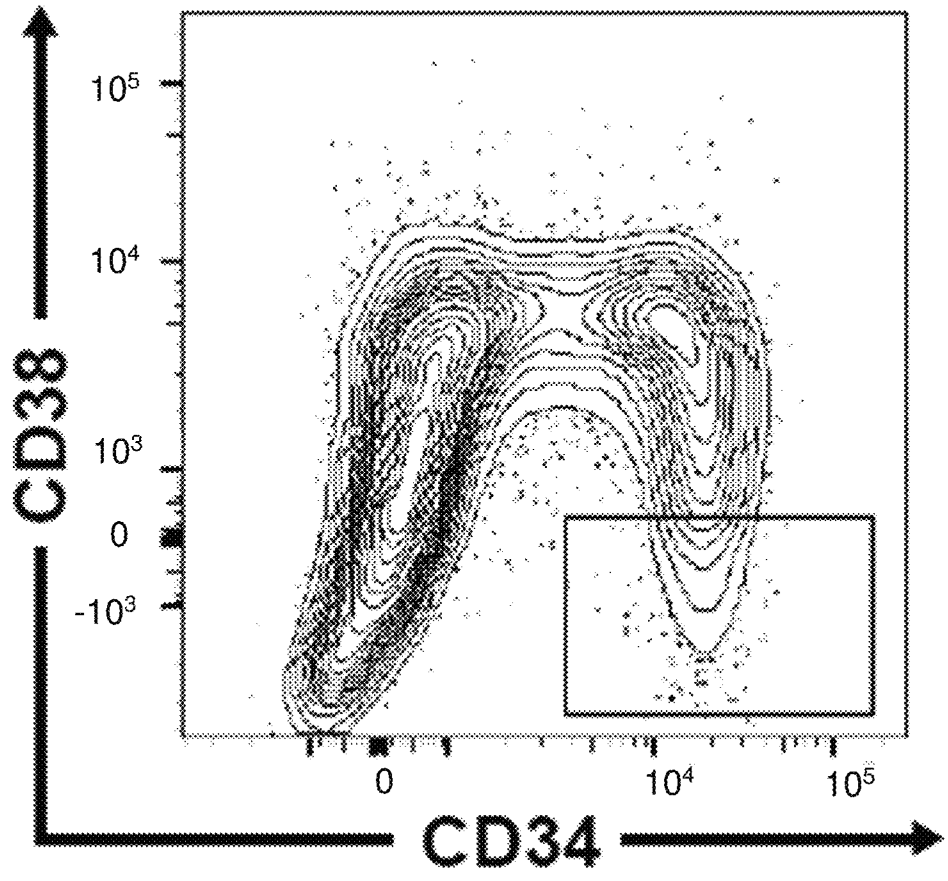

FIG. 1-cont.
B
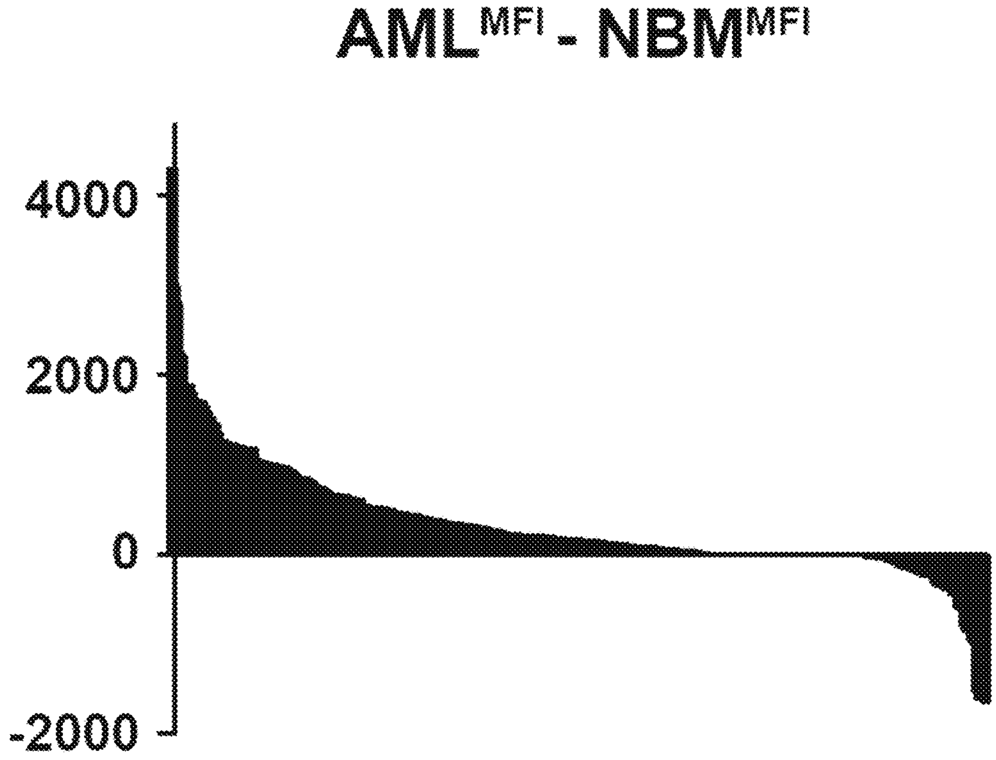
C
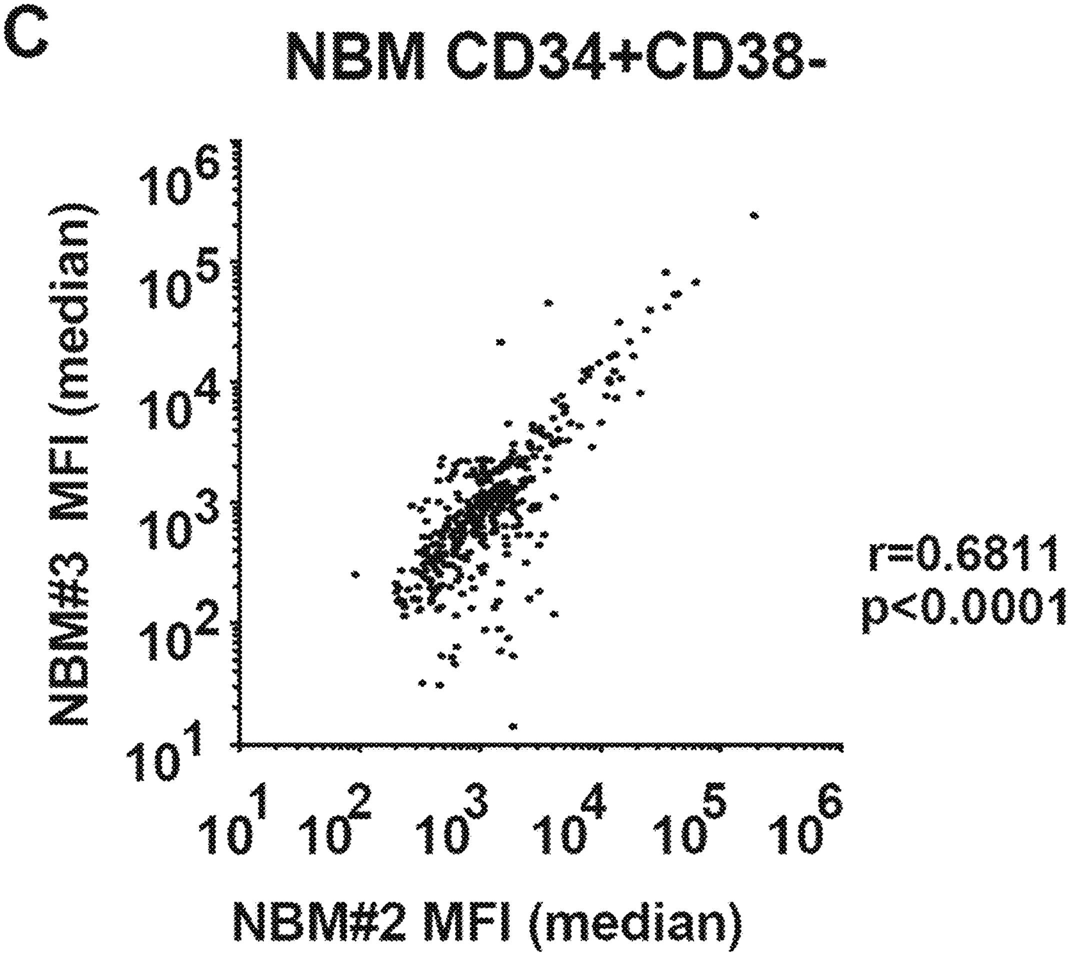

FIG. 1-cont.
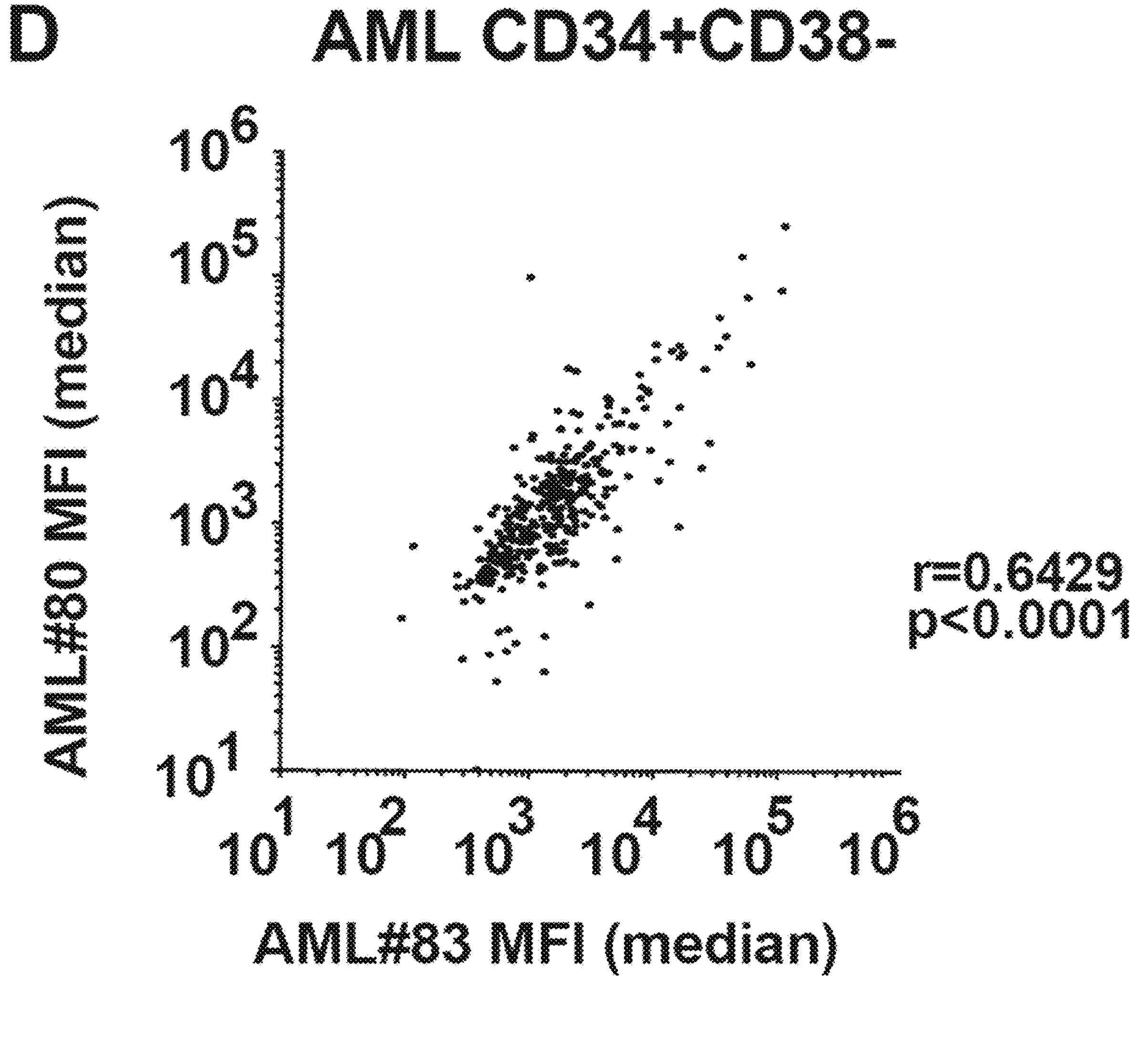

FIG. 1-cont.
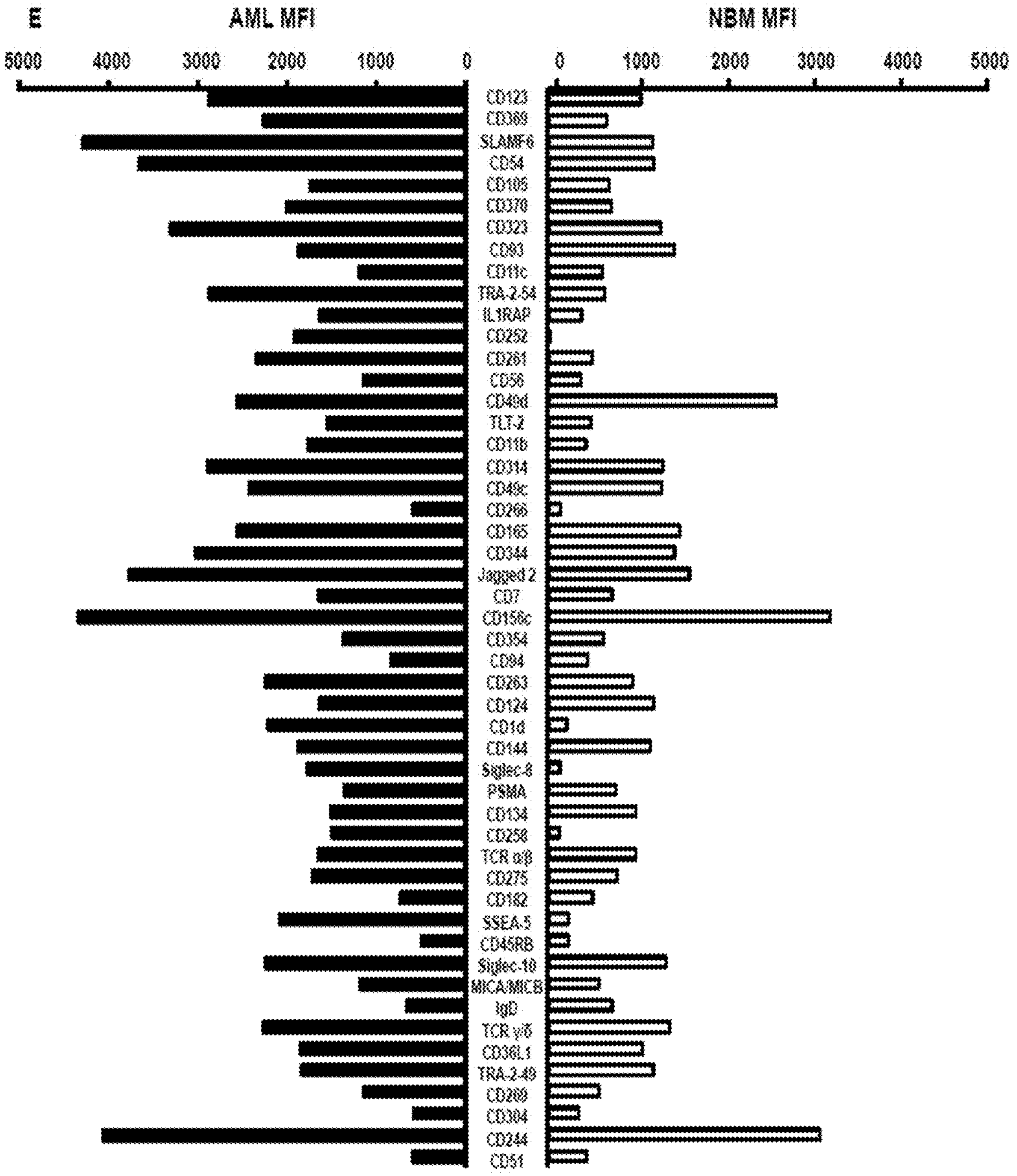

Figure 2:
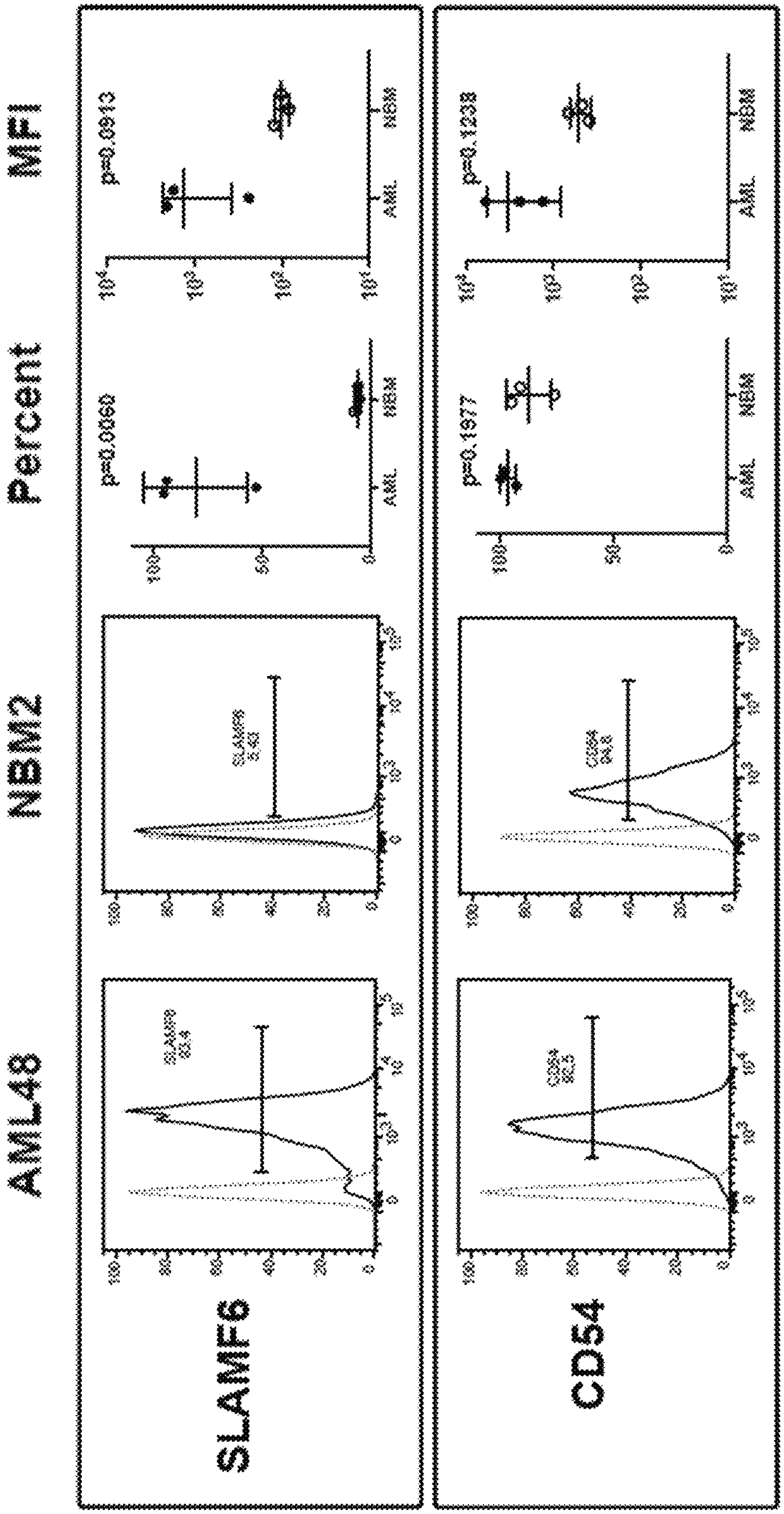

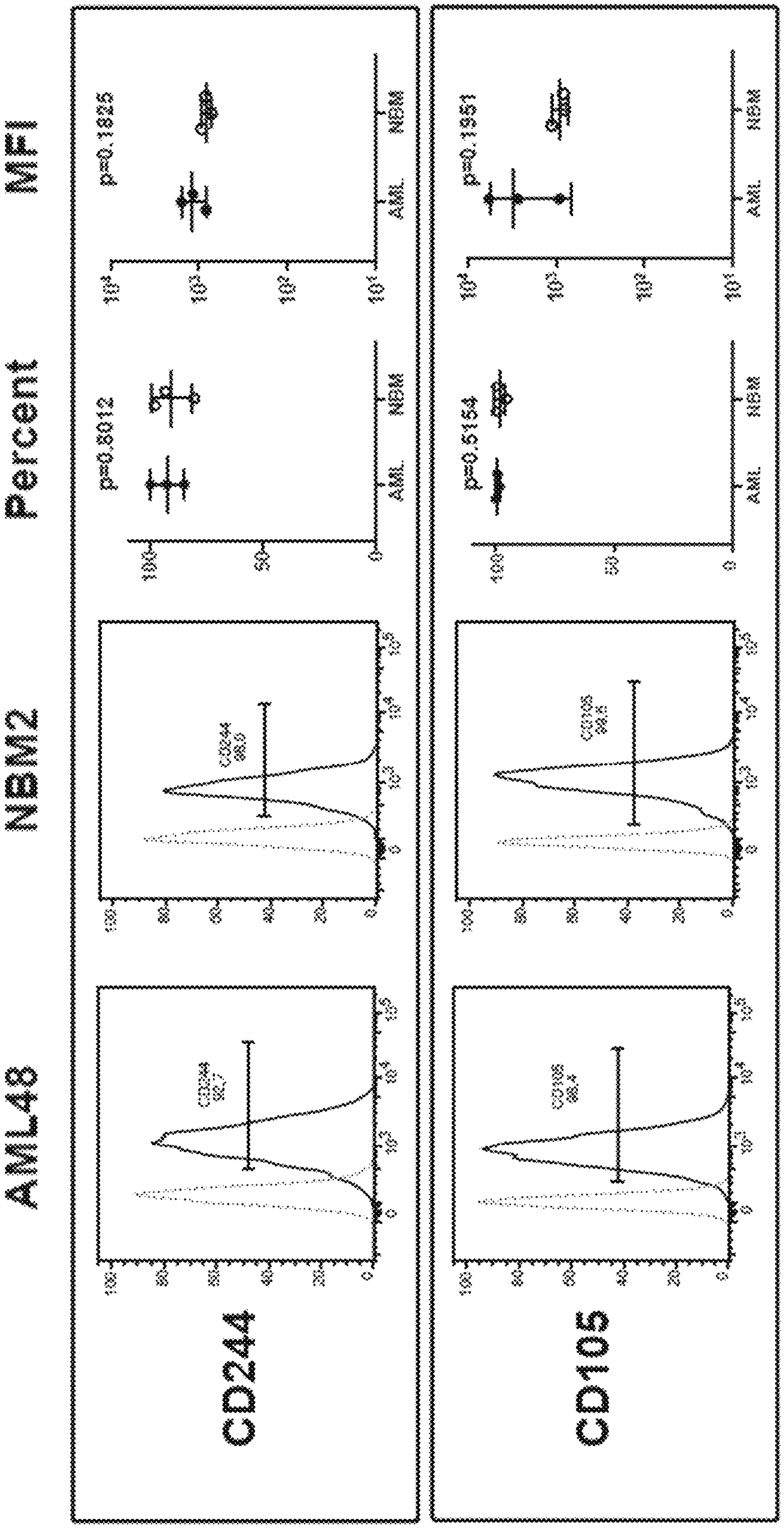
FIG. 2-cont.

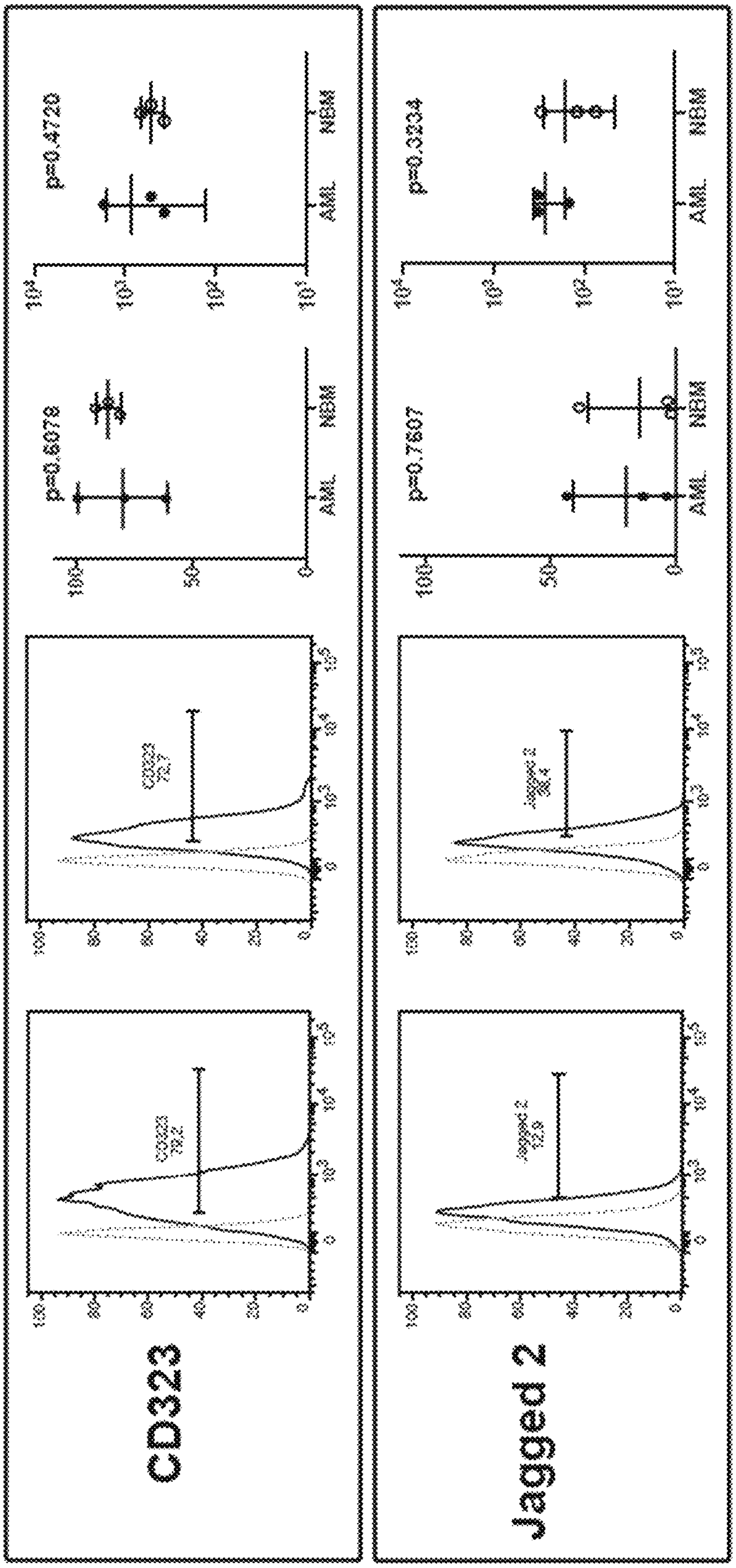
FIG. 2-cont.

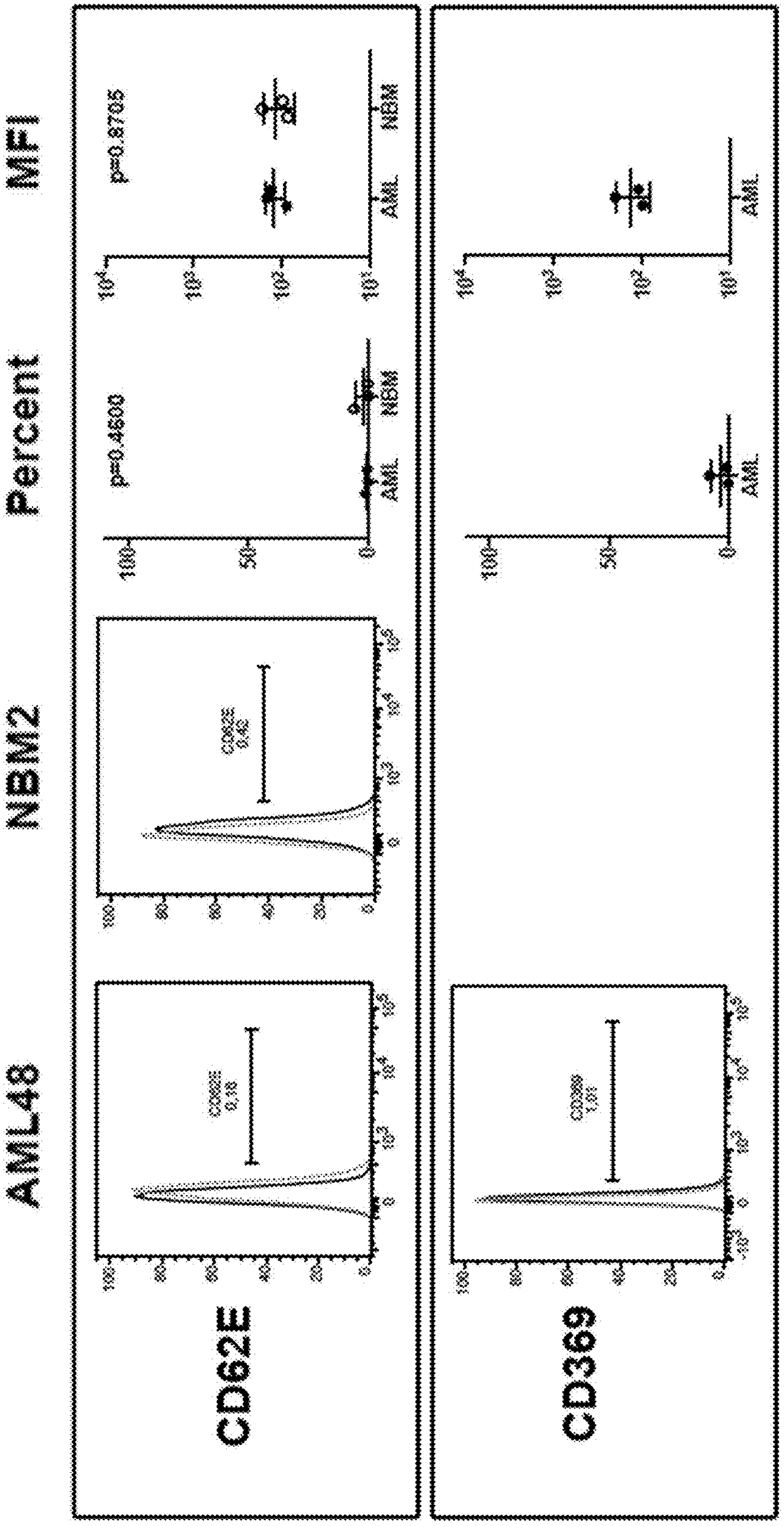
FIG. 2-cont.

Figure 3:
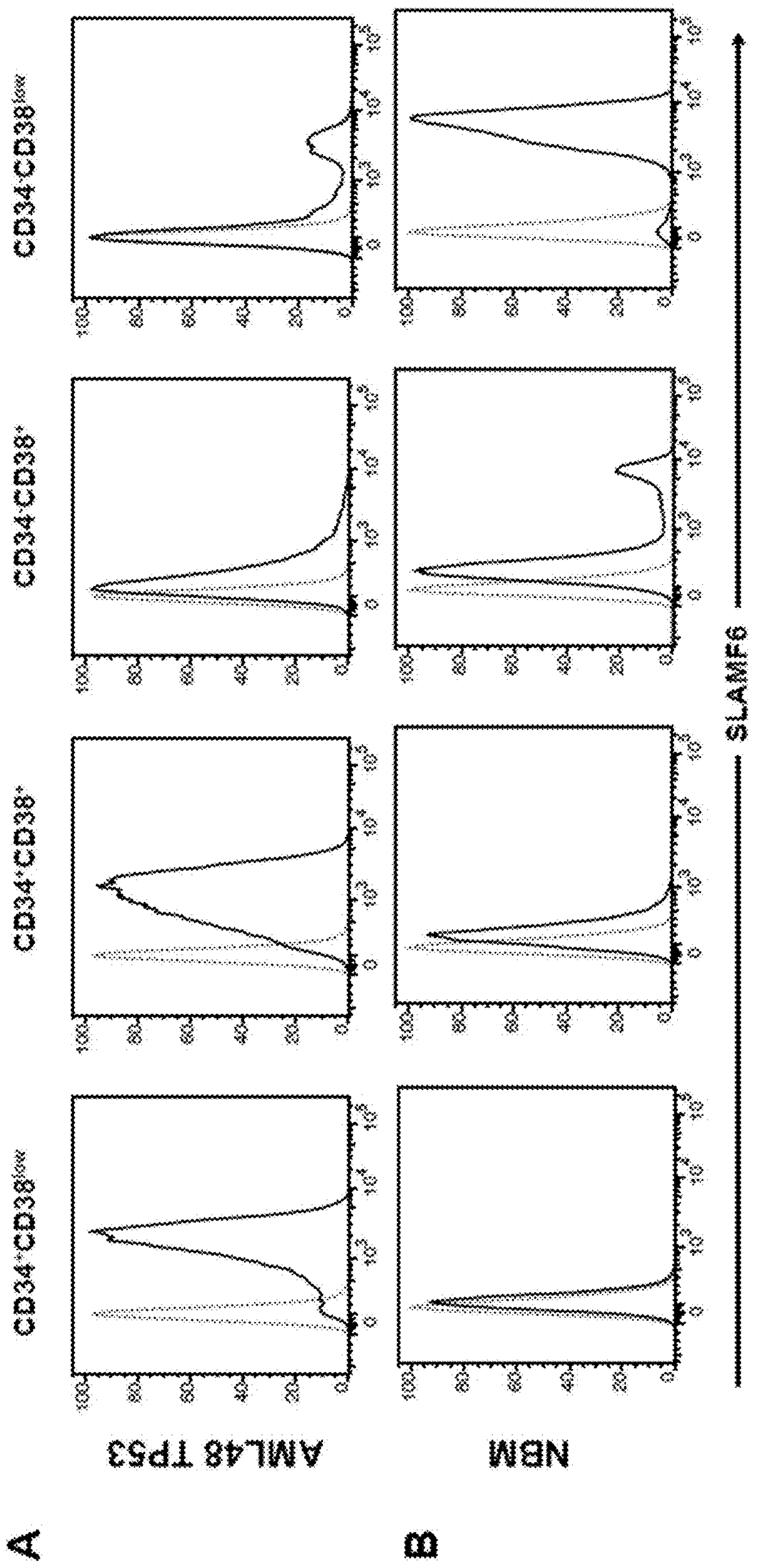

FIG.3-cont.
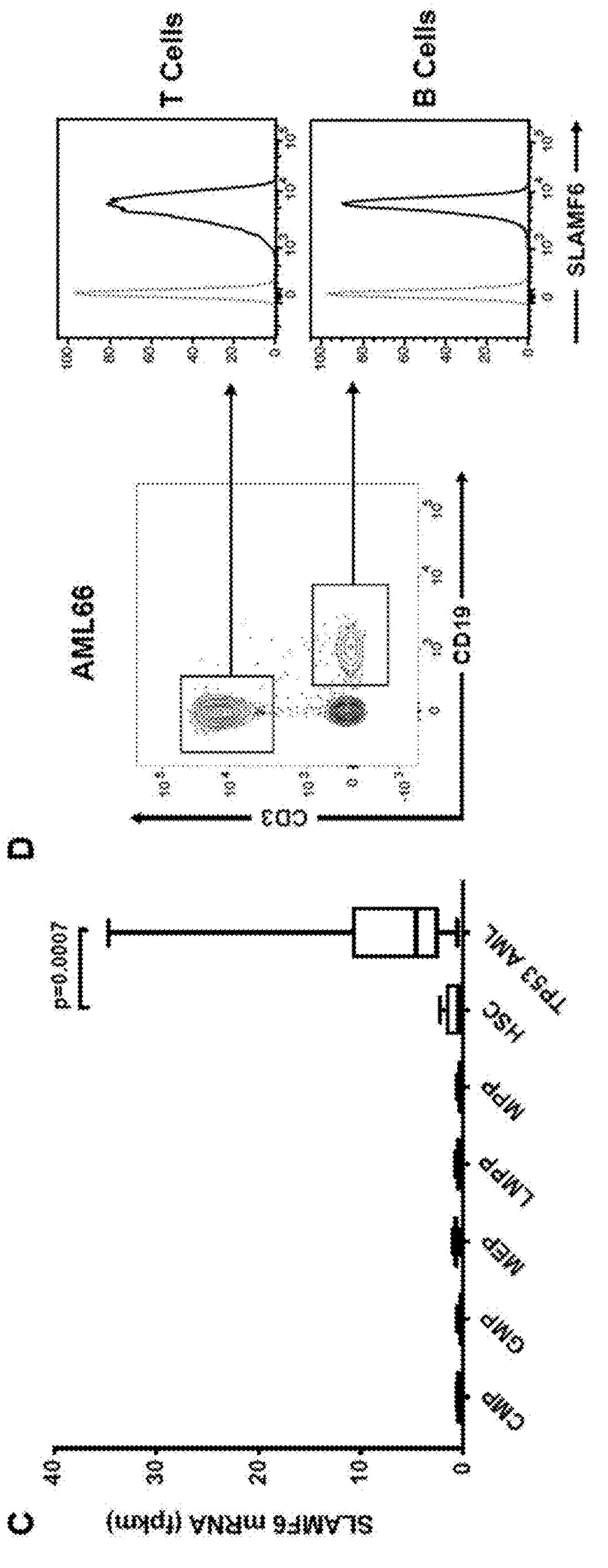

Figure 4:
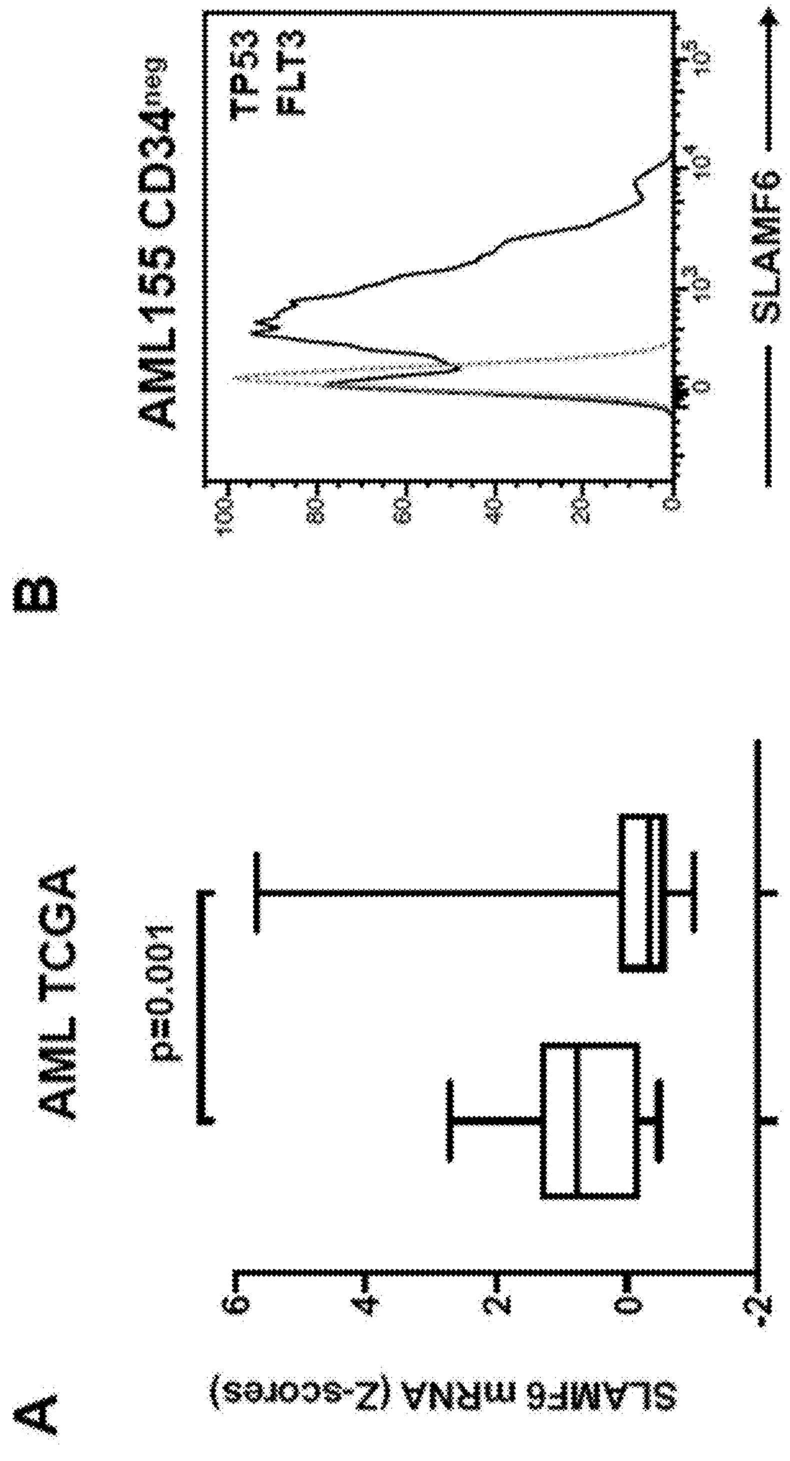

FIG.4-cont.
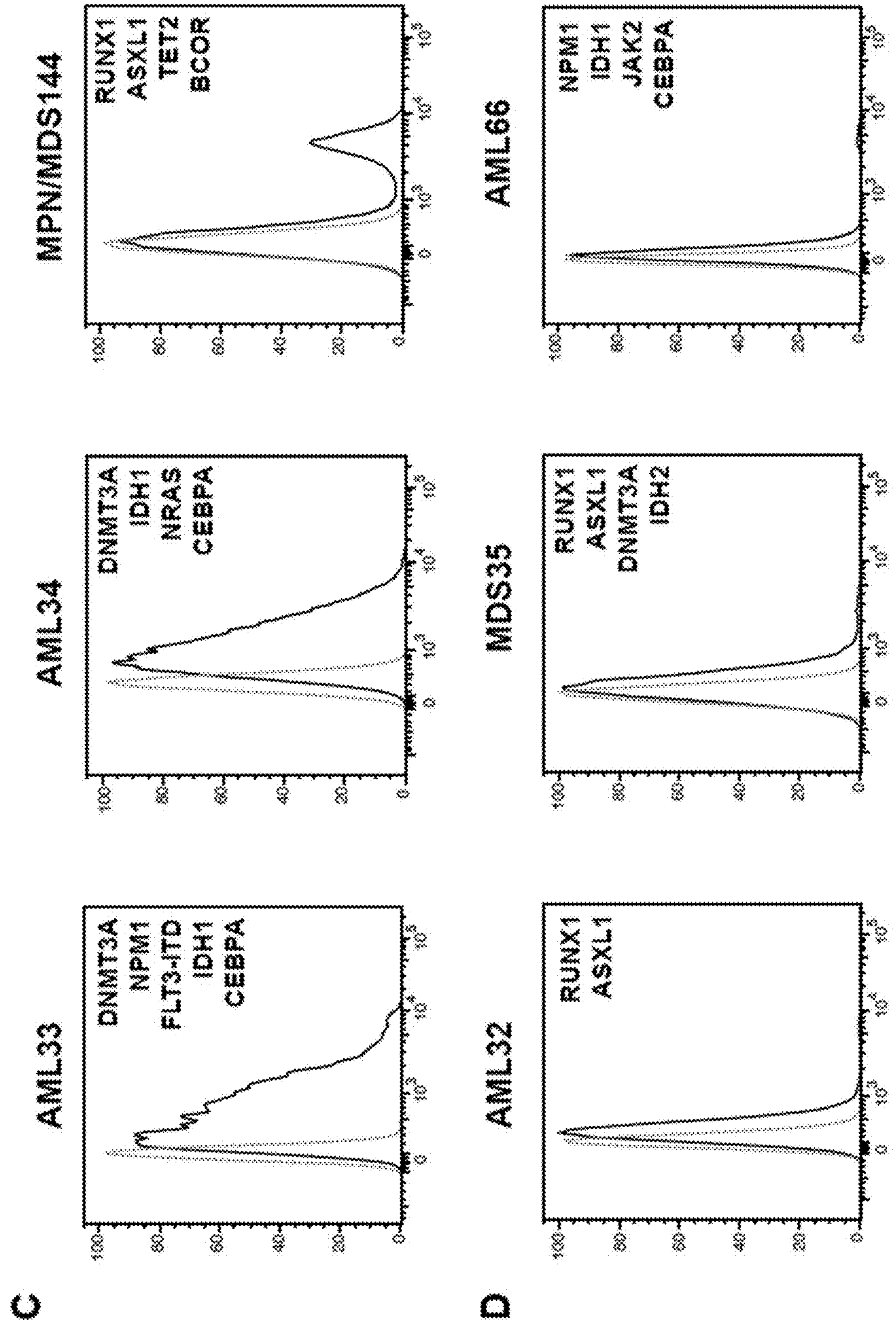

FIG. 4-cont.
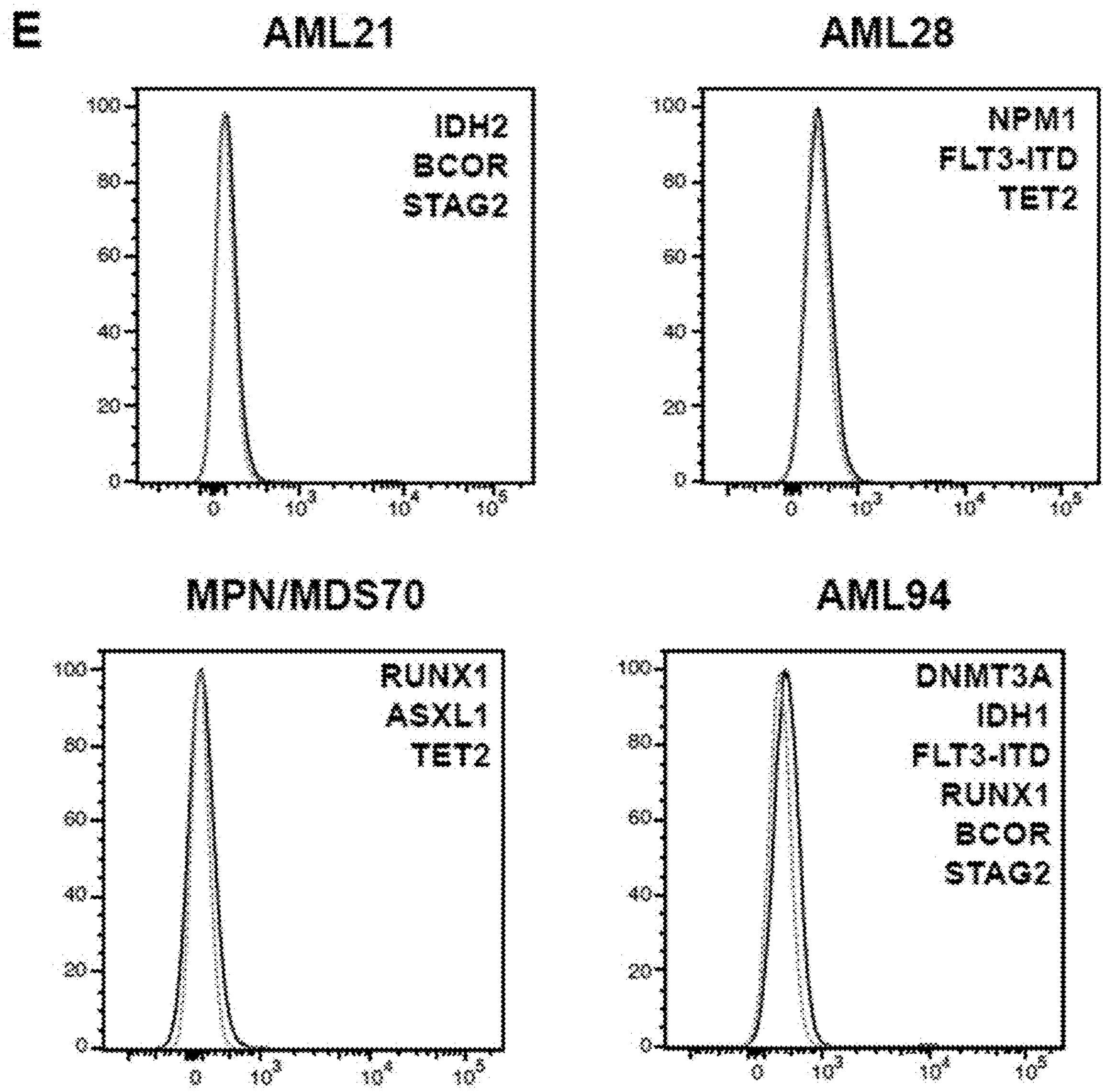

Figure 5:
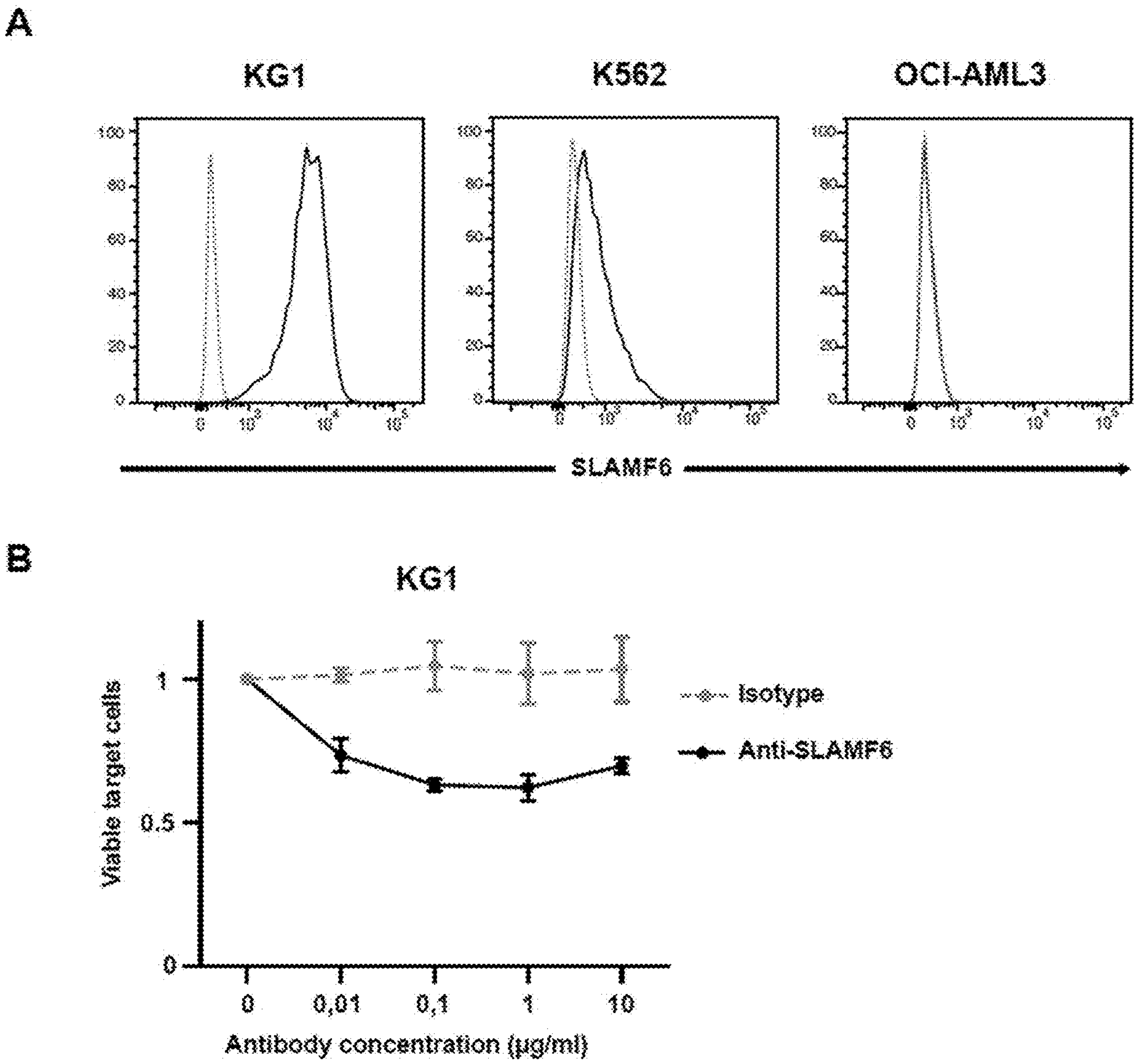

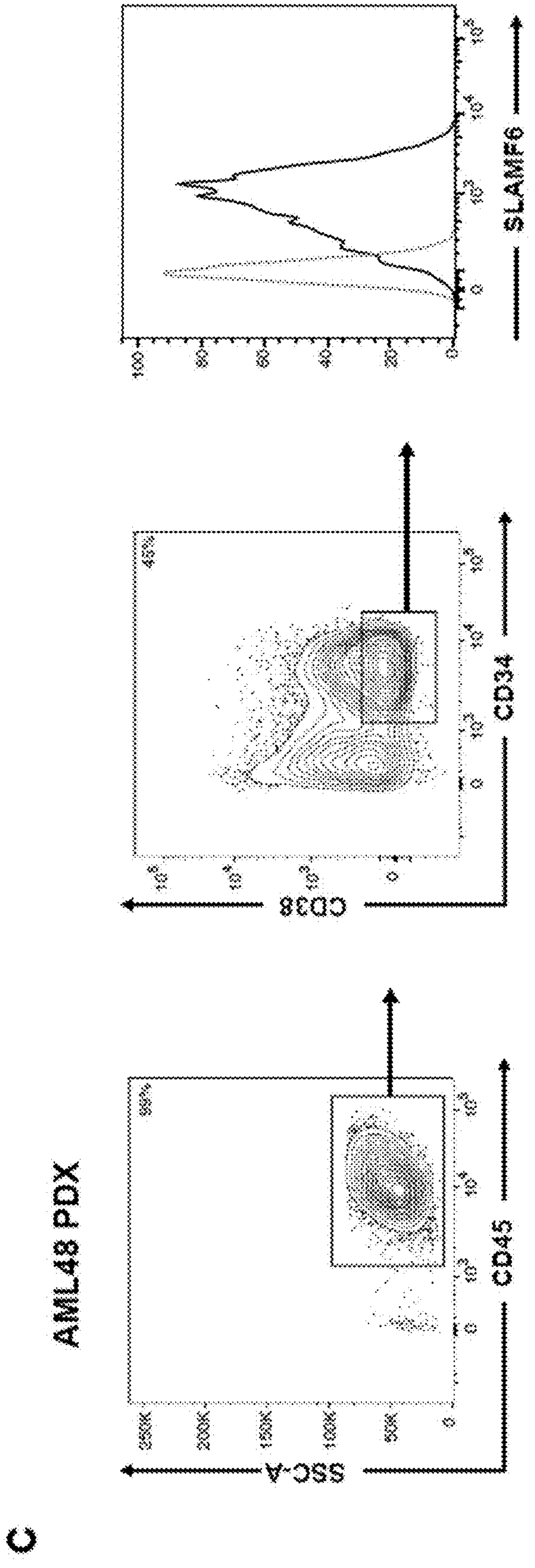
FIG. 5-cont.

A

Figure 6:
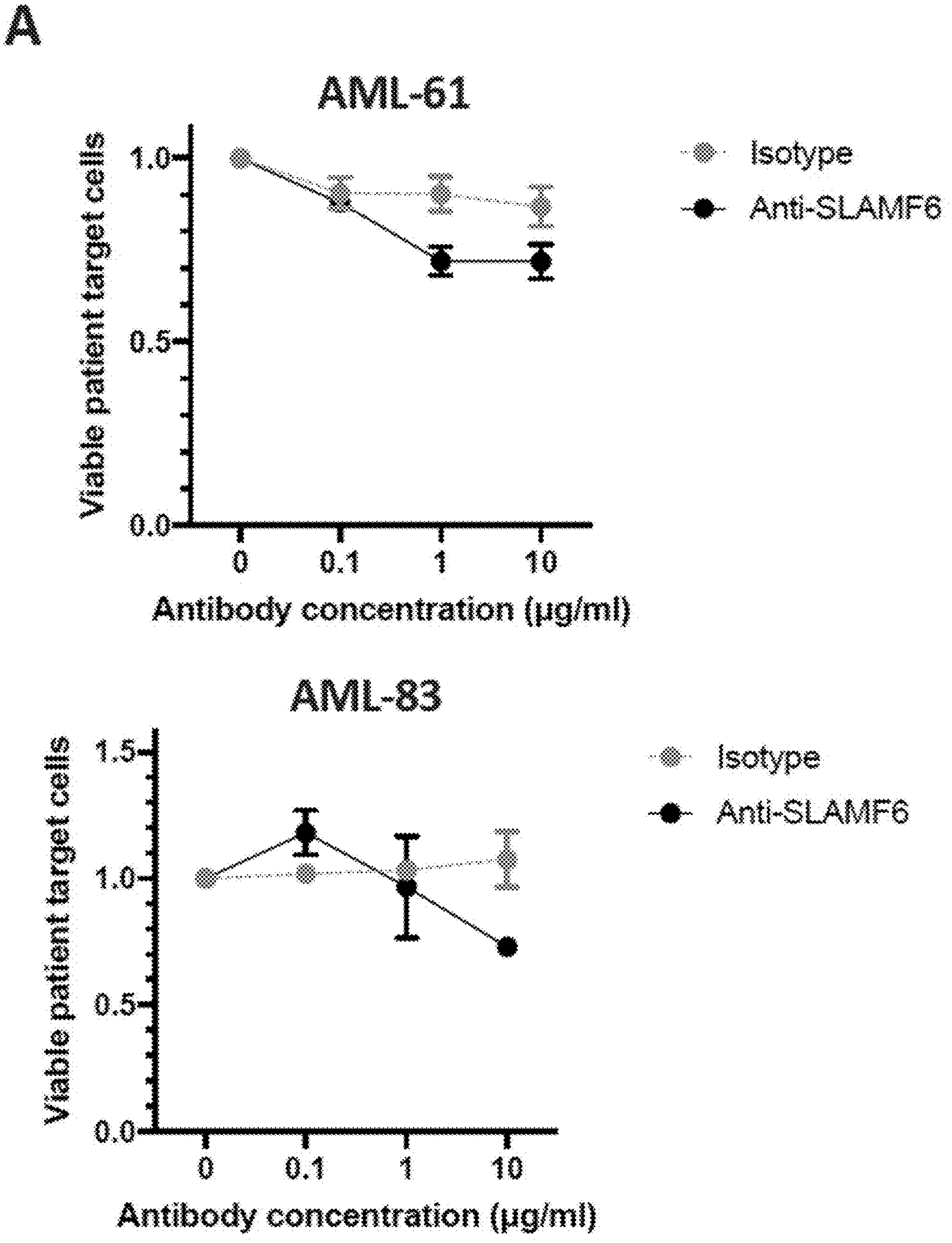

FIG. 6-cont.
B
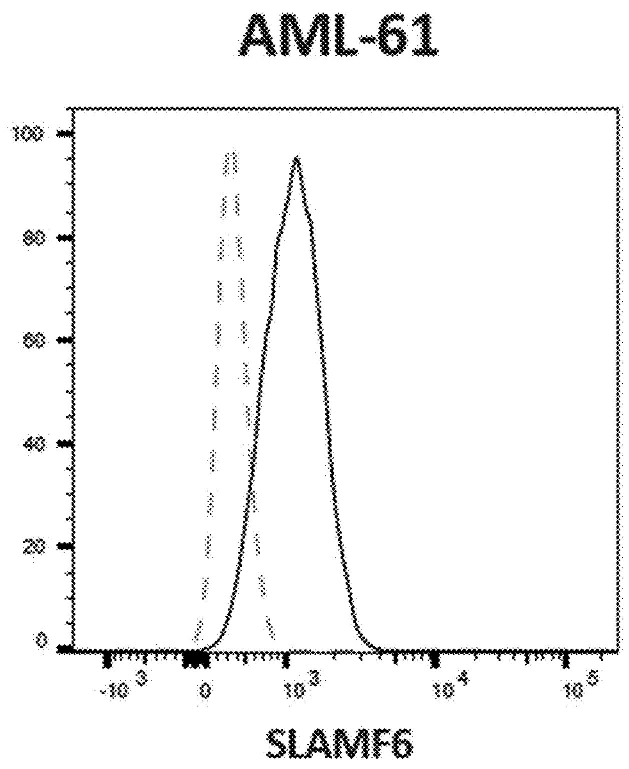
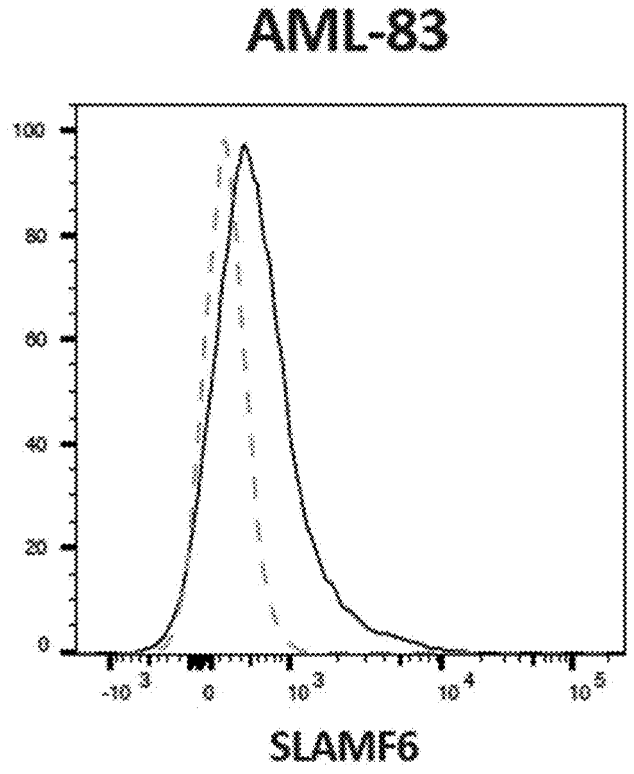

Figure 11:
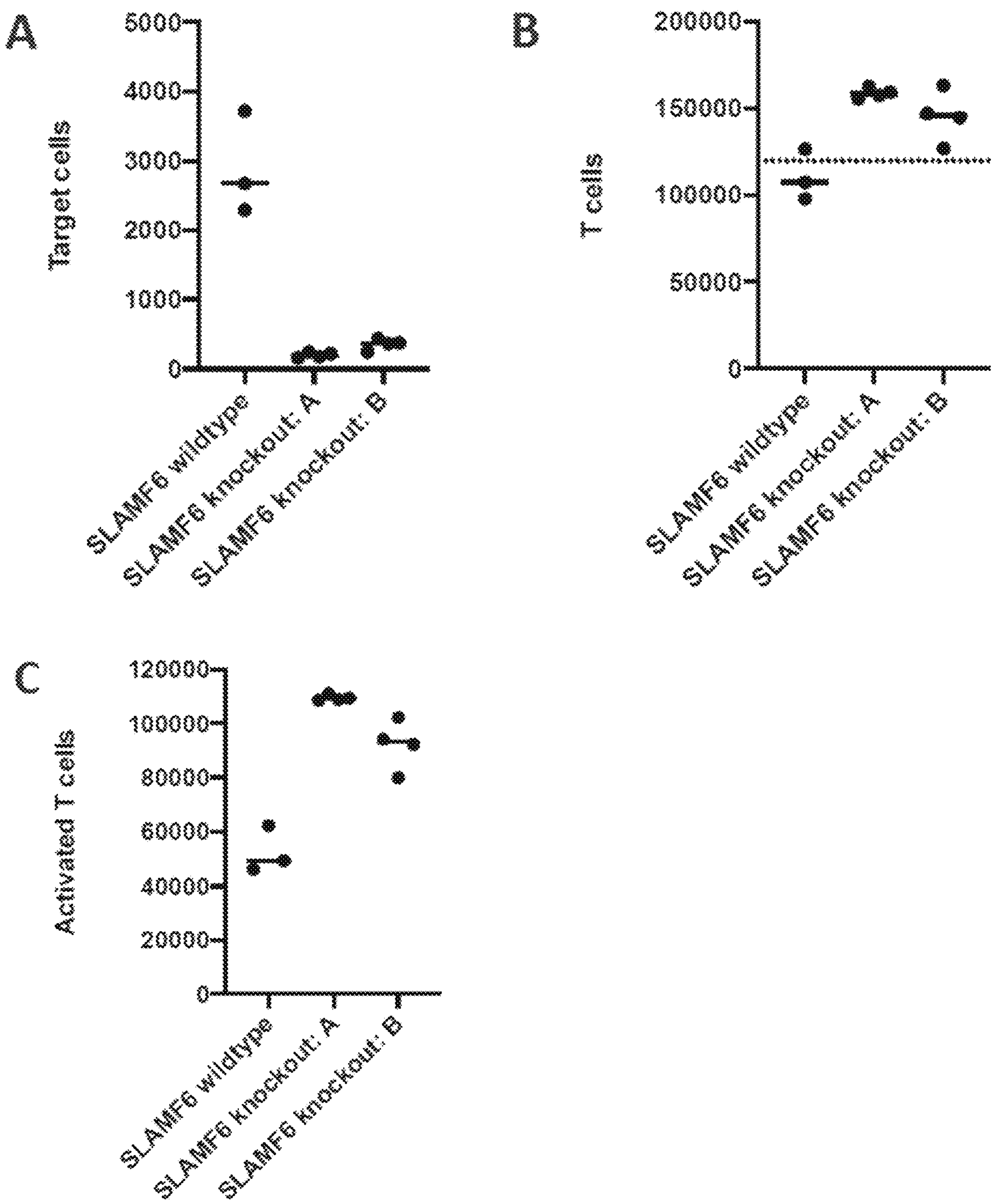

FIG. 11-cont.
D
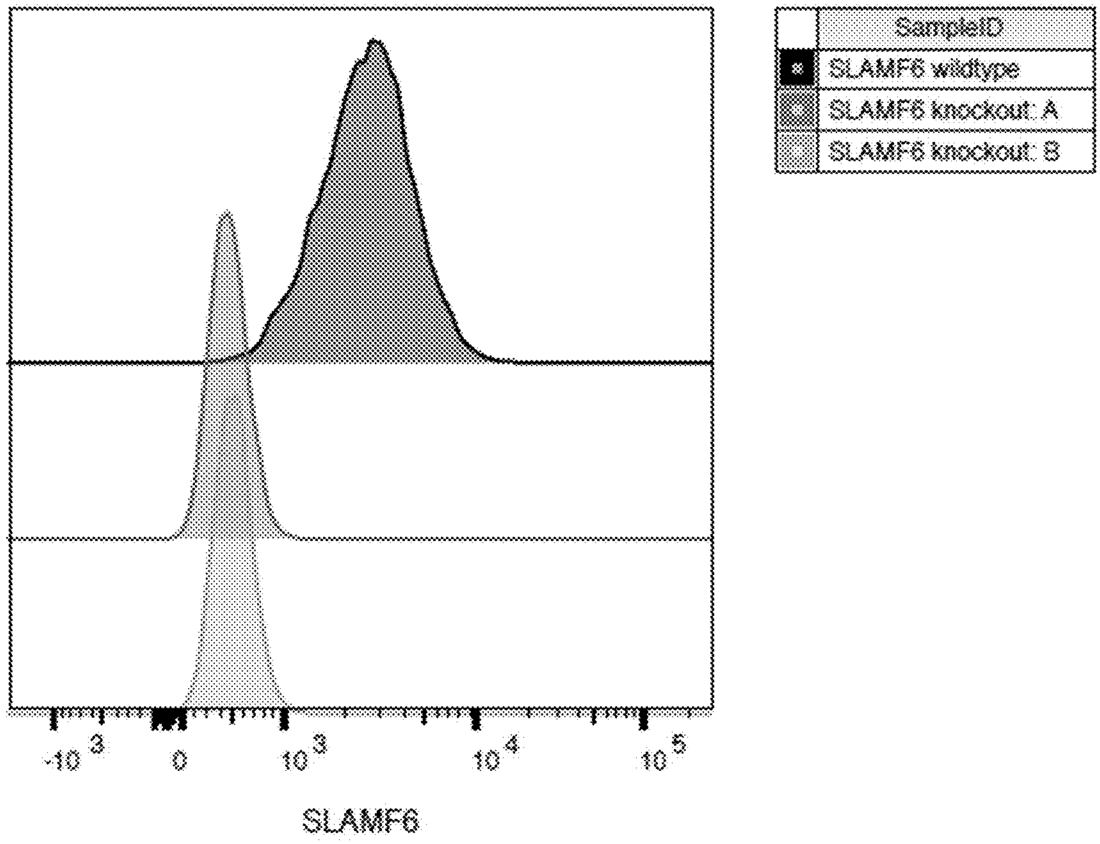

AGENTS AND USES THEREOF

This application is a national phase application under 35 U.S.C. § 371 of International Application No. PCT/EP2020/084893, filed Dec. 7, 2020, which claims the benefit of Sweden Patent Application No. 1951413-2, filed Dec. 6, 2019, the entirety of each of which is incorporated herein by reference.

FIELD OF INVENTION

The present invention relates to agents for use in the treatment and diagnosis of neoplastic hematologic disorders, such as acute myeloid leukemia (AML), acute lymphoblastic leukemia (ALL), myelodysplastic syndrome (MDS), myeloproliferative disorders (MPD)/myeloproliferative neoplasia (MPN) and chronic myeloid leukemia (CML).

BACKGROUND

Acute myeloid leukemia (AML) is, despite recent advancements in targeted therapies, still associated with an overall dismal prognosis. Newly introduced drugs such as inhibitors of FLT3, IDH1, IDH2, and BCL-2 show promise but their effects on disease outcome are still not fully discerned and most likely will not provide a cure for most genetic subgroups of AML.[1-3] Patients carrying a TP53 mutation in their leukemic cells have a poor prognosis and rarely show long term survival despite allogenic stem cell transplantation.[4-6] Recent evidence also suggest that patients that relapse with TP53 mutated AML sometimes carry the mutation at low levels already at the time of diagnosis, further emphasizing the need for specific and novel therapeutic approaches to improve the outcome for this subtype of AML.[7]

Antibody based targeted therapies have long been available in clinical practice, however, reliable and specific targets in AML have proven difficult to identify. Cell surface markers explored for therapeutic purposes in AML using recombinant antibodies include CD123, IL1RAP, CD47, TIM-3, CLL-1 and CD33.[8-13] Apart from the drug-conjugated antibody gemtuzumab ozogamicin targeting CD33 that has been approved for low or intermediate risk AML patients, these markers are still under investigation both in pre-clinical and clinical studies.[14] However, none has been specifically evaluated in the TP53 mutated setting. A therapeutic target in AML should ideally be expressed on the leukemic stem cells (LSC) (also referred to as leukemia stem cells), as these cells have the capacity to regenerate the leukemia and cause relapse but are not effectively targeted by current treatments. The precise phenotype of LSCs is still an unresolved topic but these cells are generally agreed to be enriched in the $CD34^{+}CD38^{-}$ compartment, making this a preferred population for studying LSCs in AML.[15]

In other malignancies, different members of the Signaling Lymphocytic Activating Molecule (SLAM) family have been shown to be upregulated.[16] SLAMF6, also known as NTB-A, Ly108 or CD352 is known to be expressed on human B, T and NK cells and to play a role in immune modulation and NK cell activation.[17] It is also expressed on eosinophils but not basophils or neutrophils.[18] SLAMF6 has been shown to be upregulated in myeloma, some lymphomas as well as chronic lymphocytic leukemia, however it has not been studied in the context of AML.[19-21]

For example, WO 2014/100740 A1 (Seattle Genetics, Inc.) demonstrates the expression of NTB-A on multiple myeloma cell lines and investigates antibodies directed to this target. However, WO 2014/100740 A1 provides no data to support a role for NTB-A in AML LSCs or any primary AML cells and only tests on cell lines that are known to have different surface marker expression compared with primary patient cells. The cell lines used are adapted to in vitro conditions and form homogenous cell populations that fail to recapitulate the hierarchy with a small leukemia stem cell population giving rise to a large population of more mature leukemic cells, which is characteristic of AML and other hematopoietic malignancies. Therefore, the data of WO 2014/100740 A1 fail to demonstrate the expression of SLAMF6 on AML LSCs and its potential as a therapeutic target on this critical cell population.

Furthermore, WO 2008/027739 A2 (Nuvelo, Inc.) contrarily shows all three AML or CML cell lines investigated are NTB-A (SLAMF6) negative (see FIG. 1D). Indeed, the HL-60 AML cell line is used as a negative control for SLAMF6 expression, and SLAMF6 expression is only demonstrated in lymphoid cells. Therefore, the data of WO 2008/027739 A2 does not in any way demonstrate expression of SLAMF6 in myeloid malignancies (including but not limited to AML, MDS, MPN and CML) or on the critical leukemia stem cells.

SLAMF6 is a self-ligand and thus binds to other SLAMF6 molecules, which are expressed on immune cells such as NK, T and B cells, hence its other name NTB-A. It was recently shown that targeting SLAMF6 on exhausted T cells could reactivate them and thus induce killing of leukemia cells (Yigit et al., 2019, Cancer Immunology Research). It has also been shown that SLAMF6 mediates NK cell activity (Wu et al., 2016, Nature Immunology).

SUMMARY OF INVENTION

The invention provides agents for use in the treatment and/or diagnosis of neoplastic hematologic disorders and evolved directly from the discovery by the inventors that stem cells and/or progenitor cells associated with neoplastic hematologic disorders (for example, acute myeloid leukemia (AML)) exhibit an upregulation of Signaling Lymphocytic Activating Molecule Family Member 6 (also known as SLAMF6, NTB-A, Ly108 or CD352) on their surface. In contrast, normal healthy hematopoietic stem cells (as well as progenitor cells) do not express, or show very low expression levels, of SLAMF6. Thus, the invention provides agents for use in the treatment and/or diagnosis of neoplastic hematologic disorders, such as AML, associated with upregulation of SLAMF6 on the surface of stem cells and/or progenitor cells.

Stem cells can be assessed based on the expression of particular markers, indicative of maturity. For example, immature populations can be characterized by being $CD34^{+}CD38^{+}$ or $CD34^{+}CD38^{low/-}$. $CD34^{+}CD38^{-}$ or $CD34^{+}CD38^{low}$ as used herein refer to the same potential stem cell population.

In the present study, a flowcytometry based arrayed screening assay was performed of 362 cell surface markers on diagnostic bone marrow samples from AML patients carrying a TP53 mutation and showed that SLAMF6 is specifically upregulated on immature $CD3^{-}CD19^{-}CD34^{+}CD38^{-}$ cells in TP53 mutated AML but not corresponding cells from normal bone marrow. Antibodies against SLAMF6 are also shown that can target and kill AML cells by antibody dependent cellular cytotoxicity (ADCC). This demonstrates that SLAMF6 is an interesting target for therapies in AML. Until this study, ADCC had not been demonstrated with antibodies against SLAMF6. In view of SLAMF6 being discovered as a novel target of immature $CD34^+CD38^-$ cells from AML patients and not corresponding healthy cells, it follows that cell death mechanisms of action other than ADCC would be workable when directed to these cells based on SLAMF6 expression. One such mechanism would be modulation of SLAMF6-expressing immune cells (e.g. T, B and NK cells) by interference with SLAMF6 function. In the present study, it was observed that disruption of SLAMF6 expression on AML cells increases T cell-mediated killing of said AML cells. It was also demonstrated that a SLAMF6 antibody activates T cells and promotes T cell-mediated killing of leukemia cells. SLAMF6 expression discriminates between healthy stem cells and those that are pathological, thereby providing a previously unknown therapeutic window for direct targeting of SLAMF6-expressing AML stem cells, as well as attracting immune cells for cell killing (e.g. by ADCC), activating SLAMF6-expressing immune cells (e.g. T, B or NK cells), or a combination thereof.

A first aspect of the invention provides an agent comprising or consisting of a binding moiety with specificity for Signaling Lymphocytic Activating Molecule Family Member 6 (SLAMF6) for use in inducing cell death (either directly or indirectly via triggering of the immune system) and/or inhibiting the growth (i.e. size) and/or proliferation (i.e. number) of pathological stem cells and/or progenitor cells associated with a neoplastic hematologic disorder, wherein the stem and/or progenitor cells express SLAMF6. Thus, the agent may be for use in inhibiting the growth and/or proliferation of pathological stem cells alone, of progenitor cells alone, or of both pathological stem cells and progenitor cells.

The agent may also be for use in inducing differentiation of pathological stem and/or progenitor cells which express SLAMF6.

A second, related aspect of the invention provides an agent comprising or consisting of a binding moiety with specificity for Signaling Lymphocytic Activating Molecule Family Member 6 (SLAMF6) for use in detecting pathological stem cells and/or progenitor cells associated with a neoplastic hematologic disorder, wherein the stem cells express SLAMF6. Thus, the agent may be for use in detecting pathological stem cells alone, progenitor cells alone, or both pathological stem cells and progenitor cells.

SLAMF6 may also be an attractive target for identifying subjects susceptible to cancer relapse, and/or in the treatment, prophylaxis or prevention of relapse in subjects. Relapse of cancer may be attributed to a failure of current therapies to target and remove/reduce cancer stem cells, which can often be resistant to known therapies. Cancer stem cells are the only cells with the capacity to regenerate neoplastic hematological disorders, and incomplete eradication of this population can lead to relapse, which is the major cause of death in many such diseases. Thus, having a cancer stem cell-specific marker can be beneficial for detecting and/or preventing cancer relapse (or risk thereof). Therefore, any of the aspects and embodiments described herein may be suitable for a patient subgroup that is at higher risk of cancer relapse. In one embodiment, an agent comprising or consisting of a binding moiety with specificity for Signaling Lymphocytic Activating Molecule Family Member 6 (SLAMF6) is for use in preventing or reducing the risk of relapse of a neoplastic hematologic disorder, for example relapse that develops from pathological stem cells and/or progenitor cells associated with the neoplastic hematologic disorder, wherein the stem and/or progenitor cells express SLAMF6.

By "Signaling Lymphocytic Activating Molecule Family Member 6" and "SLAMF6" we specifically include the human SLAMF6 protein, for example as described in UniProtKB/Swiss-Prot Accession No. Q96DU3. SLAMF6 is also known in the scientific literature as Activating NK Receptor; NK-T-B-Antigen; NTB-A; KALI; Natural Killer-, T- And B-Cell Antigen; NTBA Receptor; CD352 Antigen; SF2000; CD352; KALIb; Ly108; and NTBA.

By "binding moiety" we include all types of chemical entity (for example, oligonucleotides, polynucleotide, polypeptides, peptidomimetics and small compounds/molecules) which are capable of binding to SLAMF6. Advantageously, the binding moiety is capable of binding selectively (i.e. preferentially) to SLAMF6 under physiological conditions. The binding moiety preferably has specificity for human SLAMF6, which may be localised on the surface of a cell (e.g. the pathological stem cell or progenitor cell).

By "pathological stem cells" associated with a neoplastic hematologic disorder we include stem cells which are responsible for the development of a neoplastic hematologic disorder in an individual, i.e. neoplastic stem cells. In particular, the pathological stem cells may be leukemic stem cells (for example, as described in Guo et al., 2008, *Nature* 453(7194):529-33). Such stem cell may be distinguished from normal hematopoietic stem cells by their expression of the cell surface protein, SLAMF6 (see the examples below).

In one embodiment, the pathological stem cells are $CD34^+CD38^-$ cells.

In one embodiment the pathological stem cells are $CD3^-CD19^-CD34^+CD38^-$ cells.

By "progenitor cells" associated with a neoplastic hematologic disorder we include cells derived from pathological stem cells which are responsible for the development of a neoplastic hematologic disorder in an individual. In particular, the progenitor cells may be leukemic progenitor cells (for example, as described in Example 1 below). Such progenitor cells may be distinguished from normal hematopoietic progenitor cells by their higher expression of the cell surface protein, SLAMF6 (see Example 1 below). In one embodiment, the pathological progenitor cells are $CD34^+CD38^+$ cells.

By "neoplastic hematologic disorder" we specifically include hematologic cancers such as leukemias, as well as leukemia-like diseases such as myeloproliferative disorders (MPD) (also referred to as myeloproliferative neoplasia (MPN)) and myelodysplastic syndromes (MDS).

Thus, in one embodiment of the first aspect of the invention, the neoplastic hematologic disorder is a leukemic disease or disorder, i.e. a cancer of the blood or bone marrow, which may be acute or chronic.

More specifically, the neoplastic hematologic disorder may be selected from the group consisting of chronic myeloid leukemia (CML), myeloproliferative disorders (MPD), myelodysplastic syndrome (MDS), acute lymphoblastic leukemia (ALL) and acute myeloid leukemia (AML). In one particularly preferred embodiment, the neoplastic hematologic disorder is acute myeloid leukemia (AML).

In a further embodiment, the neoplastic hematologic disorder is associated with cells comprising a mutation in the TP53 gene. For example, the pathological stem cells and/or progenitor cells may comprise a TP53 mutation, such as $CD34^+CD38^-$ cells having a TP53 mutation.

TP53 mutations define a distinct subtype in AML according to the World Health Organisation (WHO) classification. Mutations of TP53 can occur throughout the gene and abrogate the function of the p53 protein in multiple ways, for example by amino acid substitution, truncation, deletion or altered splicing. Thus, TP53 mutations may refer to any mutations that alter the amino acid sequence of the p53 protein. Further, p53 function can also be disrupted by other mechanisms than TP53 mutation. For example, suitable patients may have observed or predicted loss of p53 function by other means, including but not limited to full or partial loss of chromosome 17, epigenetic silencing and alterations in p53 signaling pathways.

Thus, by "TP53 mutation" we include any observed or predicted loss or reduction of p53 function.

This may be as a result of either one or more structural mutations (i.e. wherein the amino acid sequence of the P53 protein is altered) and/or by a functional alteration (i.e. wherein the function of the p53 mutation is disrupted by other means). In a functional alteration there is an observed or predicted loss of p53 function by other means, including but not limited to full or partial loss of chromosome 17, epigenetic silencing and alterations in p53 signalling pathways, as outlined above.

Thus, in one embodiment, the neoplastic hematologic disorder is TP53 mutated AML.

In relation to the diagnostic aspects of the invention, it is sufficient that the agent is merely capable of binding to SLAMF6 present on the surface of the pathological stem cells and/or progenitor cells (without having any functional impact upon those cells).

In relation to the therapeutic and prophylactic aspects of the invention, it will be appreciated by persons skilled in the art that binding of the agent to SLAMF6 present on the surface of the pathological stem cells and/or progenitor cells may lead to a modulation (i.e. an increase or decrease) of a biological activity of SLAMF6. Modulation can be an increase or decrease in inhibition or activation of biological activity. For example, modulation can mean an increase in inhibition of a biological activity or a decrease in inhibition of a biological activity. However, such modulatory effects are not essential; for example, the agents of the invention may elicit a therapeutic and prophylactic effect simply by virtue of binding to SLAMF6 on the surface of the pathological stem cells and/or progenitor cells, which in turn may trigger the immune system to induce cell death (e.g. by ADCC).

Accordingly, in some embodiments, the therapeutic and/or prophylactic aspects of the invention may be through use of a SLAMF6 binding agent that induces cell death by ADCC; via action of a conjugated moiety, such as a moiety that is cytotoxic or radioactive, i.e. an antibody drug conjugate (ADC); and/or death receptor ligation (for example, a bispecific antibody with specificity to SLAMF6 and to said death receptor).

Additionally, modulating interactions between leukemic stem cells and immune cells and/or leukemic cells and immune cells could modulate immune activity against the leukemia, which could have strong therapeutic potential.

In one embodiment an agent targeting SLAMF6 could bring leukemia stem cells in close proximity to immunological effector cells, activate these effector cells, and enhance killing of the leukemia stem cells by effector cells.

In one embodiment an agent targeting SLAMF6 could bring leukemic cells in close proximity to immunological effector cells, activate these effector cells, and enhance killing of the leukemic cells by effector cells.

In some embodiments, the therapeutic and/or prophylactic aspects of the invention may be through use of a SLAMF6 binding agent that induces cell death by a T cell mediated mechanism. For example, the SLAMF6 binding agent may recruit T cells to target cells (e.g. the pathological stem cells and/or progenitor cells), activate T cells, and induce T cell-mediated apoptosis in the target cells via mechanisms known in the art (e.g. release of cytolytic granules, release of cytokines that recruit other effector cells, etc). Alternatively, or additionally, the SLAMF6 binding agent may prevent a SLAMF6-mediated response that would otherwise prevent T cell function and/or activation, for example by masking or blocking the interaction between SLAMF6 expressing pathological stem cells and/or progenitor cells and T cells. Similarly, the SLAMF6 binding agent may recruit, activate or otherwise stimulate immune cells, such as NK cells, for increased anti-leukemic effects.

By "biological activity of SLAMF6" we include any interaction or signalling event which involves SLAMF6 on pathological stem cells and/or progenitor cells.

Such inhibition of the biological activity of SLAMF6 by an agent of the invention may be in whole or in part. For example, the agent may inhibit the biological activity of SLAMF6 by at least 10%, preferably at least 20%, 30%, 40%, 50%, 60%, 70%, 80% or 90%, and most preferably by 100% compared to the biological activity of SLAMF6 in pathological stem cells and/or progenitor cells which have not been exposed to the agent. In a preferred embodiment, the agent is capable of inhibiting the biological activity of SLAMF6 by 50% or more compared to the biological activity of SLAMF6 in pathological stem cells and/or progenitor cells which have not been exposed to the agent. The biological activity of SLAMF6 that is inhibited could be, for example, its self-ligand activity (SLAMF6 interacting with other SLAMF6) and/or downstream signalling. Examples of downstream signalling include, but are not limited to, recruitment and/or phosphorylation of mediators such as SAP, Fyn, EAT-2 and SHP-1.2 (reviewed in Yigit et al., 2018, Clinical Immunology).

Likewise, it will be appreciated that inhibition of growth and/or proliferation of the pathological stem cells and/or progenitor cells may be in whole or in part. For example, the agent may inhibit the growth and/or proliferation of the pathological stem cells and/or progenitor cells by at least 10%, preferably at least 20%, 30%, 40%, 50%, 60%, 70%, 80% or 90%, and most preferably by 100% compared to the growth and/or proliferation of the pathological stem cells and/or progenitor cells which have not been exposed to the agent.

Similarly, it will be appreciated that the induction of differentiation of pathological stem cells and/or progenitor cells may be to any extent. For example, the agent may induce differentiation of the pathological stem cells and/or progenitor cells by at least 10%, preferably at least 20%, 30%, 40%, 50%, 60%, 70%, 80% or 90%, and most preferably by 100% compared to the differentiation of the pathological stem cells and/or progenitor cells which have not been exposed to the agent.

Additionally, in one embodiment the agent is capable of modulating the interaction between an immune cell and leukemic stem cells. By immune cell, we include B cells, T cells and/or NK cells. In one embodiment, the immune cell expresses SLAMF6.

Additionally, in one embodiment the agent is capable of modulating the interaction between an immune cell and leukemic cells. By immune cell, we include B cells, T cells and/or NK cells. In one embodiment, the immune cell expresses SLAMF6.

Thus, in one embodiment, the agent is capable of recruiting and/or activating (which includes enhancing an ongoing function) immune cells, such as B cells, T cells and/or NK cells that express SLAMF6.

In a further preferred embodiment, the agent is capable of killing the pathological stem cells and/or progenitor cells. In particular, the agent may be capable of inducing stem cell and/or progenitor cell death by apoptosis or autophagy. For example, the agent may induce apoptosis by antibody-dependent cell-mediated cytotoxicity (ADCC). In certain embodiments, the killing of pathogenic stem cells and/or progenitor cells may be enhanced by the agent modulating the interaction between an immune cell and leukemic stem cells. In one embodiment, the immune cells express SLAMF6.

In a further preferred embodiment, the agent is capable of killing the leukemic cells. In particular, the agent may be capable of inducing leukemic cell death by apoptosis or autophagy. For example, the agent may induce apoptosis by antibody-dependent cell-mediated cytotoxicity (ADCC). In certain embodiments, the killing of leukemic cells may be enhanced by the agent modulating the interaction between an immune cell and leukemic cells. In one embodiment, the immune cells express SLAMF6.

In one embodiment, the killing of pathogenic stem cells and/or progenitor cells may be enhanced by the agent recruiting and/or activating immune cells, such as B cells, T cells and/or NK cells, preferably wherein the immune cells recruited are also SLAMF6 positive.

As indicated above, the agents of the invention may comprise or consist of any suitable chemical entity constituting a binding moiety with specificity for SLAMF6.

Methods for detecting interactions between a test chemical entity and SLAMF6 are well known in the art. For example, ultrafiltration with ion spray mass spectroscopy/HPLC methods or other physical and analytical methods may be used. In addition, Fluorescence Energy Resonance Transfer (FRET) methods may be used, in which binding of two fluorescent labelled entities may be observed by measuring the interaction of the fluorescent labels when in close proximity to each other.

Alternative methods of detecting binding of SLAMF6 to macromolecules, for example DNA, RNA, proteins and phospholipids, include a surface plasmon resonance assay, for example as described in Plant et al., 1995, *Analyt Biochem* 226(2), 342-348. Such methods may make use of a polypeptide that is labelled, for example with a radioactive or fluorescent label.

A further method of identifying a chemical entity that is capable of binding to SLAMF6 is one where the protein is exposed to the compound and any binding of the compound to the said protein is detected and/or measured. The binding constant for the binding of the compound to the polypeptide may be determined. Suitable methods for detecting and/or measuring (quantifying) the binding of a compound to a polypeptide are well known to those skilled in the art and may be performed, for example, using a method capable of high throughput operation, for example a chip-based method. Technology called VLSIPS™ has enabled the production of extremely small chips that contain hundreds of thousands or more of different molecular probes. These biological chips have probes arranged in arrays, each probe assigned a specific location. Biological chips have been produced in which each location has a scale of, for example, ten microns. The chips can be used to determine whether target molecules interact with any of the probes on the chip. After exposing the array to target molecules under selected test conditions, scanning devices can examine each location in the array and determine whether a target molecule has interacted with the probe at that location.

Another method of identifying compounds with binding affinity for SLAMF6 is the yeast two-hybrid system, where the polypeptides of the invention can be used to "capture" proteins that bind SLAMF6. The yeast two-hybrid system is described in Fields & Song, *Nature* 340:245-246 (1989).

In one preferred embodiment, the agent comprises or consists of a polypeptide.

For example, the agent may comprise or consist of an antibody or an antigen-binding fragment thereof with binding specificity for SLAMF6, or a variant, fusion or derivative of said antibody or antigen-binding fragment, or a fusion of a said variant or derivative thereof, which retains the binding specificity for SLAMF6.

By "antibody" we include substantially intact antibody molecules, as well as chimaeric antibodies, humanised antibodies, human antibodies (wherein at least one amino acid is mutated relative to the naturally occurring human antibodies), single chain antibodies, bispecific antibodies, antibody heavy chains, antibody light chains, homodimers and heterodimers of antibody heavy and/or light chains, and antigen binding fragments and derivatives of the same.

By "antigen-binding fragment" we mean a functional fragment of an antibody that is capable of binding to SLAMF6.

Preferably, the antigen-binding fragment is selected from the group consisting of Fv fragments (e.g. single chain Fv and disulphide-bonded Fv), Fab-like fragments (e.g. Fab fragments, Fab' fragments and $F(ab)_2$ fragments), single variable domains (e.g. $V_H$ and $V_L$ domains) and domain antibodies (dAbs, including single and dual formats [i.e. dAb-linker-dAb]).

The advantages of using antibody fragments, rather than whole antibodies, are several-fold. The smaller size of the fragments may lead to improved pharmacological properties, such as better penetration of solid tissue. Moreover, antigen-binding fragments such as Fab, Fv, ScFv and dAb antibody fragments can be expressed in and secreted from *E. coli*, thus allowing the production of large amounts of the said fragments.

Also included within the scope of the invention are modified versions of antibodies and antigen-binding fragments thereof, e.g. modified by the covalent attachment of polyethylene glycol or other suitable polymers (see below).

Methods of generating antibodies and antibody fragments are well known in the art. For example, antibodies may be generated via any one of several methods which employ induction of in vivo production of antibody molecules, screening of immunoglobulin libraries (Orlandi et al, 1989. *Proc. Natl. Acad. Sci. U.S.A.* 86:3833-3837; Winter et al., 1991, *Nature* 349:293-299) or generation of monoclonal antibody molecules by cell lines in culture. These include, but are not limited to, the hybridoma technique, the human B-cell hybridoma technique, and the Epstein-Barr virus (EBV)-hybridoma technique (Kohler et al., 1975. *Nature* 256:4950497; Kozbor et al., 1985. *J. Immunol. Methods* 81:31-42; Cote et al., 1983. *Proc. Natl. Acad. Sci. USA* 80:2026-2030; Cole et al., 1984. *Mol. Cell. Biol.* 62:109-120).

Suitable monoclonal antibodies to selected antigens may be prepared by known techniques, for example those disclosed in "*Monoclonal Antibodies: A manual of techniques*", H Zola (CRC Press, 1988) and in "*Monoclonal Hybridoma Antibodies: Techniques and Applications*", J G R Hurrell (CRC Press, 1982).

Likewise, antibody fragments can be obtained using methods well known in the art (see, for example, Harlow & Lane, 1988, *"Antibodies: A Laboratory Manual*", Cold Spring Harbor Laboratory, New York). For example, antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment. Alternatively, antibody fragments can be obtained by pepsin or papain digestion of whole antibodies by conventional methods.

It will be appreciated by persons skilled in the art that for human therapy or diagnostics, human or humanised antibodies are preferably used. Humanised forms of non-human (e.g. murine) antibodies are genetically engineered chimaeric antibodies or antibody fragments having preferably minimal-portions derived from non-human antibodies. Humanised antibodies include antibodies in which complementary determining regions of a human antibody (recipient antibody) are replaced by residues from a complementary determining region of a non-human species (donor antibody) such as mouse, rat of rabbit having the desired functionality. In some instances, Fv framework residues of the human antibody are replaced by corresponding non-human residues. Humanised antibodies may also comprise residues which are found neither in the recipient antibody nor in the imported complementarity determining region or framework sequences. In general, the humanised antibody will comprise substantially all of at least one, and typically two, variable domains, in which all or substantially all of the complementarity determining regions correspond to those of a non-human antibody and all, or substantially all, of the framework regions correspond to those of a relevant human consensus sequence. Humanised antibodies optimally also include at least a portion of an antibody constant region, such as an Fc region, typically derived from a human antibody (see, for example, Jones et al., 1986. *Nature* 321:522-525; Riechmann et al., 1988, *Nature* 332:323-329; Presta, 1992, *Curr. Op. Struct. Biol.* 2:593-596).

Methods for humanising non-human antibodies are well known in the art. Generally, the humanised antibody has one or more amino acid residues introduced into it from a source which is non-human. These non-human amino acid residues, often referred to as imported residues, are typically taken from an imported variable domain. Humanisation can be essentially performed as described (see, for example, Jones et al., 1986, *Nature* 321:522-525; Reichmann et al., 1988. *Nature* 332:323-327; Verhoeyen et al., 1988, *Science* 239: 1534-15361; U.S. Pat. No. 4,816,567) by substituting human complementarity determining regions with corresponding rodent complementarity determining regions. Accordingly, such humanised antibodies are chimaeric antibodies, wherein substantially less than an intact human variable domain has been substituted by the corresponding sequence from a non-human species. In practice, humanised antibodies may be typically human antibodies in which some complementarity determining region residues and possibly some framework residues are substituted by residues from analogous sites in rodent antibodies.

Human antibodies can also be identified using various techniques known in the art, including phage display libraries (see, for example, Hoogenboom & Winter, 1991, *J. Mol. Biol.* 227:381; Marks et al., 1991, *J. Mol. Biol.* 222:581; Cole et al., 1985, In: *Monoclonal antibodies and Cancer Therapy*, Alan R. Liss, pp. 77; Boerner et al., 1991. *J. Immunol.* 147:86-95).

Once suitable antibodies are obtained, they may be tested for activity, for example by ELISA.

In an alternative embodiment of the first aspect of the invention, the agent comprises or consists of a non-immunoglobulin binding moiety, for example as described in Skerra, *Curr Opin Biotechnol.* 2007 August; 18(4):295-304.

In a further alternative embodiment, the agent comprises or consists of an aptamer. For example, the agent may comprise or consist of a peptide aptamer or a nucleic acid aptamer (see Hoppe-Seyler & Butz, 2000, *J Mol Med.* 78 (8): 426-30; Bunka D H & Stockley P G, 2006, *Nat Rev Microbiol.* 4 (8): 588-96 and Drabovich et al., 2006, *Anal Chem.* 78 (9): 3171-8).

In a still further alternative embodiment, the agent comprises or consists of a small chemical entity (i.e. small molecules). Such entities with SLAMF6 binding properties may be identified by screening commercial libraries of small compounds/molecules (for example, as available from ChemBridge Corporation, San Diego, USA)

In addition to the binding moiety, the agents of the invention may further comprise a moiety for increasing the in vivo half-life of the agent, such as but not limited to polyethylene glycol (PEG), human serum albumin, glycosylation groups, fatty acids and dextran. Such further moieties may be conjugated or otherwise combined with the binding moiety using methods well known in the art.

Likewise, it will be appreciated that the agents of the invention may further comprise a cytotoxic moiety. For example, the cytotoxic moiety may comprise or consist of a radioisotope, such as astatine-211, bismuth-212, bismuth-213, iodine-131, yttrium-90, lutetium-177, samarium-153 and palladium-109. Alternatively, the cytotoxic moiety may comprise or consist of a toxin (such as saporin or calicheamicin). In a further alternative, the cytotoxic moiety may comprise or consist of a chemotherapeutic agent (such as an antimetabolite).

Likewise, it will be appreciated that the agents of the invention may further comprise a detectable moiety. For example, the detectable moiety may comprise or consist of a radioisotope, such as technetium-99m, indium-111, gallium-67, gallium-68, arsenic-72, zirconium-89, iodine-12 or thallium-201. Alternatively, the detectable moiety comprises or consists of a paramagnetic isotope, such as gadolinium-157, manganese-55, dysprosium-162, chromium-52 or iron-56.

Cytotoxic and detectable moieties may be conjugated or otherwise combined with the binding moiety using methods well known in the art (for example, the existing immunoconjugate therapy, gemtuzumab ozogamicin [tradename: Mylotarg®], comprises a monoclonal antibody linked to the cytotoxin calicheamicin).

A third aspect of the invention provides a pharmaceutical composition comprising an effective amount of an agent as defined in relation to the first or second aspects of the invention together with a pharmaceutically acceptable buffer, diluent, carrier, adjuvant or excipient.

Additional compounds may also be included in the compositions, including, chelating agents such as EDTA, citrate, EGTA or glutathione.

The pharmaceutical compositions may be prepared in a manner known in the art that is sufficiently storage stable and suitable for administration to humans and animals. For example, the pharmaceutical compositions may be lyophilised, e.g. through freeze drying, spray drying, spray cooling, or through use of particle formation from supercritical particle formation.

By “pharmaceutically acceptable” we mean a non-toxic material that does not decrease the effectiveness of the SLAMF6-binding activity of the agent of the invention. Such pharmaceutically acceptable buffers, carriers or excipients are well-known in the art (see Remington’s Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000), the disclosures of which are incorporated by reference).

The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelacetic acid, PIPES, SSC, SSPE, POPSO, TAPS, TABS, TAPSO and TES.

The term "diluent" is intended to mean an aqueous or non-aqueous solution with the purpose of diluting the agent in the pharmaceutical preparation. The diluent may be one or more of saline, water, polyethylene glycol, propylene glycol, ethanol or oils (such as safflower oil, corn oil, peanut oil, cottonseed oil or sesame oil).

The term "adjuvant" is intended to mean any compound added to the formulation to increase the biological effect of the agent of the invention. The adjuvant may be one or more of zinc, copper or silver salts with different anions, for example, but not limited to fluoride, chloride, bromide, iodide, thiocyanate, sulfite, hydroxide, phosphate, carbonate, lactate, glycolate, citrate, borate, tartrate, and acetates of different acyl composition. The adjuvant may also be cationic polymers such as cationic cellulose ethers, cationic cellulose esters, deacetylated hyaluronic acid, chitosan, cationic dendrimers, cationic synthetic polymers such as poly (vinyl imidazole), and cationic polypeptides such as polyhistidine, polylysine, polyarginine, and peptides containing these amino acids.

The excipient may be one or more of carbohydrates, polymers, lipids and minerals. Examples of carbohydrates include lactose, glucose, sucrose, mannitol, and cyclodextrines, which are added to the composition, e.g. for facilitating lyophilisation. Examples of polymers are starch, cellulose ethers, cellulose carboxymethylcellulose, hydroxypropylmethyl cellulose, hydroxyethyl cellulose, ethylhydroxyethyl cellulose, alginates, carrageenans, hyaluronic acid and derivatives thereof, polyacrylic acid, polysulphonate, polyethylene glycol/polyethylene oxide, polyethylene oxide/polypropylene oxide copolymers, polyvinylalcohol/polyvinylacetate of different degree of hydrolysis, and polyvinylpyrrolidone, all of different molecular weight, which are added to the composition, e.g. for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of the different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The agents of the invention may be formulated into any type of pharmaceutical composition known in the art to be suitable for the delivery thereof.

In one embodiment, the pharmaceutical compositions of the invention may be in the form of a liposome, in which the agent is combined, in addition to other pharmaceutically acceptable carriers, with amphipathic agents such as lipids, which exist in aggregated forms as micelles, insoluble monolayers and liquid crystals. Suitable lipids for liposomal formulation include, without limitation, monoglycerides, diglycerides, sulfatides, lysolecithin, phospholipids, saponin, bile acids, and the like. Suitable lipids also include the lipids above modified by poly(ethylene glycol) in the polar headgroup for prolonging bloodstream circulation time. Preparation of such liposomal formulations is can be found in for example U.S. Pat. No. 4,235,871, the disclosures of which are incorporated herein by reference.

The pharmaceutical compositions of the invention may also be in the form of biodegradable microspheres. Aliphatic polyesters, such as poly(lactic acid) (PLA), poly(glycolic acid) (PGA), copolymers of PLA and PGA (PLGA) or poly(caprolactone) (PCL), and polyanhydrides have been widely used as biodegradable polymers in the production of microspheres. Preparations of such microspheres can be found in U.S. Pat. No. 5,851,451 and in EP 0 213 303, the disclosures of which are incorporated herein by reference.

In a further embodiment, the pharmaceutical compositions of the invention are provided in the form of polymer gels, where polymers such as starch, cellulose ethers, cellulose carboxymethylcellulose, hydroxypropylmethyl cellulose, hydroxyethyl cellulose, ethylhydroxyethyl cellulose, alginates, carrageenans, hyaluronic acid and derivatives thereof, polyacrylic acid, polyvinyl imidazole, polysulphonate, polyethylene glycol/polyethylene oxide, polyethylene oxide/polypropylene oxide copolymers, polyvinylalcohol/polyvinylacetate of different degree of hydrolysis, and polyvinylpyrrolidone are used for thickening of the solution containing the agent. The polymers may also comprise gelatin or collagen.

Alternatively, the agents may simply be dissolved in saline, water, polyethylene glycol, propylene glycol, ethanol or oils (such as safflower oil, corn oil, peanut oil, cottonseed oil or sesame oil), tragacanth gum, and/or various buffers.

It will be appreciated that the pharmaceutical compositions of the invention may include ions and a defined pH for potentiation of action of the active agent. Additionally, the compositions may be subjected to conventional pharmaceutical operations such as sterilisation and/or may contain conventional adjuvants such as preservatives, stabilisers, wetting agents, emulsifiers, buffers, fillers, etc.

The pharmaceutical compositions according to the invention may be administered via any suitable route known to those skilled in the art. Thus, possible routes of administration include parenteral (intravenous, subcutaneous, and intramuscular), topical, ocular, nasal, pulmonary, buccal, oral, parenteral, vaginal and rectal. Also, administration from implants is possible.

In one preferred embodiment, the pharmaceutical compositions are administered parenterally, for example, intravenously, intracerebroventricularly, intraarticularly, intraarterially, intraperitoneally, intrathecally, intraventricularly, intrasternally, intracranially, intramuscularly or subcutaneously, or they may be administered by infusion techniques. They are conveniently used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Thus, the pharmaceutical compositions of the invention are particularly suitable for parenteral, e.g. intravenous, administration.

Alternatively, the pharmaceutical compositions may be administered intranasally or by inhalation (for example, in the form of an aerosol spray presentation from a pressurised container, pump, spray or nebuliser with the use of a suitable propellant, such as dichlorodifluoromethane, trichlorofluoro-methane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas). In the case of a pressurised aerosol, the dosage unit may be determined by providing a valve to deliver a metered amount. The pressurised container, pump, spray or nebuliser may contain a solution or suspension of the active polypeptide, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

The pharmaceutical compositions will be administered to a patient in a pharmaceutically effective dose. A 'therapeutically effective amount', or 'effective amount', or 'therapeutically effective', as used herein, refers to that amount which provides a therapeutic effect for a given condition and administration regimen. This is a predetermined quantity of active material calculated to produce a desired therapeutic effect in association with the required additive and diluent, i.e. a carrier or administration vehicle. Further, it is intended to mean an amount sufficient to reduce and most preferably prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art. The administration of the pharmaceutically effective dose can be carried out both by single administration in the form of an individual dose unit or else several smaller dose units and also by multiple administrations of subdivided doses at specific intervals. Alternatively, the does may be provided as a continuous infusion over a prolonged period.

The polypeptides can be formulated at various concentrations, depending on the efficacy/toxicity of the compound being used. Preferably, the formulation comprises the active agent at a concentration of between 0.1 μM and 1 mM, more preferably between 1 μM and 500 μM, between 500 μM and 1 mM, between 300 μM and 700 μM, between 1 μM and 100 μM, between 100 μM and 200 μM, between 200 μM and 300 μM, between 300 μM and 400 μM, between 400 μM and 500 μM and most preferably about 500 μM.

It will be appreciated by persons skilled in the art that the pharmaceutical compositions of the invention may be administered alone or in combination with other therapeutic agents used in the treatment of a neoplastic hematologic disorder, such as inhibitors of tyrosine kinase (e.g. imatinib mesylate [Glivec®], dasatinib, nilotinib), omacetaxine, antimetabolites (e.g. cytarabine, hydroxyurea), alkylating agents, Interferon alpha-2b and/or steroids.

A fourth aspect of the invention provides a kit comprising an agent as defined in relation to the first or second aspects of the invention or a pharmaceutical composition according to the third aspect of the invention.

A fifth aspect of the invention provides the use of an agent as defined in relation to the first or second aspects of the invention in the preparation of a medicament for inducing cell death and/or inhibiting the growth and/or proliferation of pathological stem cells and/or progenitor cells associated with a neoplastic hematologic disorder, wherein the stem cells and/or progenitor cells express SLAMF6.

The agent may also be for use in inducing differentiation of pathological stem and/or progenitor cells which express SLAMF6.

A related sixth aspect of the invention provides the use of an agent as defined in relation to the first or second aspects of the invention in the preparation of a diagnostic agent for detecting pathological stem cells and/or progenitor cells associated with a neoplastic hematologic disorder, wherein the stem cells and/or progenitor cells express SLAMF6. Another related aspect of the invention may be the diagnosis of a patient population that is at risk of relapse; such as relapse may be caused by the persistence of cancer stem cells.

A related seventh aspect of the invention provides the use of an agent as defined in relation to the first or second aspects of the invention for detecting pathological stem cells and/or progenitor cells associated with a neoplastic hematologic disorder, wherein the stem cells and/or progenitor cells express SLAMF6.

In one embodiment of the above use aspects of the invention, the neoplastic hematologic disorder is a leukemia. In a further embodiment, the neoplastic hematologic disorder may be associated with cells comprising a TP53 mutation. Mutations of TP53 can occur throughout the gene and abrogate the function of the p53 protein in multiple ways, for example by amino acid substitution, truncation, deletion or altered splicing. Thus, TP53 mutations may refer to any mutations that alter the protein sequence of the p53 protein. Further, p53 function can also be disrupted by other mechanisms than TP53 mutation. For example, suitable patients may have observed or predicted loss of p53 function by other means, including but not limited to full or partial loss of chromosome 17, epigenetic silencing and alterations in p53 signaling pathways.

Thus, by "TP53 mutation" we include any observed or predicted loss or reduction of p53 function.

This may be as a result of either one or more structural mutations (i.e. wherein the amino acid sequence of the P53 protein is altered) and/or by a functional alteration (i.e. wherein the function of the p53 mutation is disrupted by other means). In a functional alteration there is an observed or predicted loss of p53 function by other means, including but not limited to full or partial loss of chromosome 17, epigenetic silencing and alterations in p53 signaling pathways, as outlined above.

In another further embodiment, the neoplastic hematologic disorder may be associated with cells expressing CD34$^+$CD38$^-$. In yet another further embodiment, the neoplastic hematologic disorder may be associated with cells comprising a TP53 mutation and expressing CD34$^+$CD38$^-$.

More specifically, the neoplastic hematologic disorder may be selected from the group consisting of chronic myeloid leukemia (CML), myeloproliferative disorders (MPD), myelodysplastic syndrome (MDS), acute lymphoblastic leukemia (ALL) and acute myeloid leukemia (AML). In one particularly preferred embodiment, the neoplastic hematologic disorder is acute myeloid leukemia (AML).

An eighth aspect of the invention provides a method for inducing cell death and/or inhibiting the growth and/or proliferation of pathological stem cells and/or progenitor cells associated with a neoplastic hematologic disorder in an individual, comprising the step of administering to the individual an effective amount of an agent as defined in relation to the first or second aspects of the invention, or a pharmaceutical composition according to the third aspect of the invention, wherein the stem cells and/or progenitor cells express SLAMF6. In a further embodiment, the neoplastic hematologic disorder may be associated with cells comprising a TP53 mutation. In another further embodiment, the neoplastic hematologic disorder may be associated with cells expressing CD34$^+$CD38$^-$. In yet another further embodiment, the neoplastic hematologic disorder may be associated with cells comprising a TP53 mutation and expressing CD34$^+$CD38$^-$.

The method may also be for inducing differentiation of pathological stem and/or progenitor cells which express SLAMF6.

Thus, the invention provides methods for the treatment of neoplastic hematologic disorders. By 'treatment' we include both therapeutic and prophylactic treatment of the patient. The term 'prophylactic' is used to encompass the use of a polypeptide or formulation described herein, which either prevents or reduces the likelihood of a neoplastic hematologic disorder in a patient or subject.

As above, the neoplastic hematologic disorder may be selected from the group consisting of chronic myeloid leukemia (CML), myeloproliferative disorders (MPD), myelodysplastic syndrome (MDS), acute lymphoblastic leukemia (ALL) and acute myeloid leukemia (AML). In one particularly preferred embodiment, the neoplastic hematologic disorder is acute myeloid leukemia (AML).

A ninth aspect of the invention provides a method for detecting pathological stem cells and/or progenitor cells associated with neoplastic hematologic disorder in an individual, comprising the step of administering to the individual an effective amount of an agent as defined in relation to the first or second aspects of the invention, or a pharmaceutical composition according to the third aspect of the invention, wherein the stem cells and/or progenitor cells express SLAMF6. In a further embodiment, the neoplastic hematologic disorder may be associated with cells comprising a TP53 mutation. In another further embodiment, the neoplastic hematologic disorder may be associated with cells expressing CD34$^+$CD38$^-$. In yet another further embodiment, the neoplastic hematologic disorder may be associated with cells comprising a TP53 mutation and expressing CD34$^+$CD38$^-$.

As above, the neoplastic hematologic disorder may be selected from the group consisting of chronic myeloid leukemia (CML), myeloproliferative disorders (MPD), myelodysplastic syndrome (MDS), acute lymphoblastic leukemia (ALL) and acute myeloid leukemia (AML). In one particularly preferred embodiment, the neoplastic hematologic disorder is acute myeloid leukemia (AML).

A tenth aspect of the invention provides an in vitro method for diagnosing or prognosing a neoplastic hematologic disorder.

In one embodiment, the method comprises:

(a) providing a bone marrow or peripheral blood sample of haematopoietic cells from an individual to be tested;
(b) isolating a subpopulation of CD34$^+$, CD38$^-$ cells from the haematopoietic cells; and
(c) determining whether stem cells, contained within the CD34$^+$, CD38$^-$ cells, express the cell surface markers SLAMF6;
    wherein stem cells that exhibit the cell surface marker profile CD34$^+$, CD38$^-$ and SLAMF6$^+$ are indicative of the individual having or developing leukemia.

In one embodiment, the method comprises:

(a) isolating a subpopulation of CD34$^+$, CD38$^-$ cells from haematopoietic cells in a sample; and
(b) determining whether stem cells, contained within the CD34$^+$, CD38$^-$ cells, express the cell surface markers SLAMF6;
    wherein stem cells that exhibit the cell surface marker profile CD34$^+$, CD38$^-$ and SLAMF6$^+$ are indicative of the individual having or developing leukemia. The sample may optionally be a bone marrow sample or peripheral blood sample.

In an alternative embodiment, the in vitro method for diagnosing or prognosing a neoplastic hematologic disorder comprises the following steps:

(a) providing a bone marrow or peripheral blood sample of haematopoietic cells from an individual to be tested; and
(b) isolating a subpopulation of SLAMF6$^+$, CD34$^+$, CD38$^-$ cells from the haematopoietic cells;
    wherein stem cells that exhibit the cell surface marker profile CD34$^+$, CD38$^-$ and SLAMF6$^+$ are indicative of the individual having or developing leukemia.

In one embodiment, the method comprises: isolating a subpopulation of SLAMF6$^+$, CD34$^+$, CD38$^-$ cells from haematopoietic cells in a sample; wherein stem cells that exhibit the cell surface marker profile CD34$^+$, CD38$^-$ and SLAMF6$^+$ are indicative of the individual having or developing leukemia. The sample may optionally be a bone marrow sample or peripheral blood sample.

In all embodiments of the tenth aspect, the provision of a sample is not necessarily to be construed as involving a surgical step. The provision of a sample could be a pre-isolated and stored frozen sample, for example. Further, the term "isolating" is to be construed as meaning the same as "detecting" and "determining". For example, step (b) could be the step of "detecting a subpopulation" or "determining whether a subpopulation exists".

In one embodiment of the above in vitro method, it is used to identify patients that may be at a risk (or increased risk) of cancer relapse. Thus, potentially in addition to diagnosing or prognosing a neoplastic hematologic disorder (such as in a sample derived from a patient), the method may also diagnose or prognose an increased risk of relapse of the neoplastic hematologic disorder. For example, the in vitro method may be used to identify patients with leukemic stem cells (LSC), which are cells that have the capacity to regenerate the leukemia and cause relapse but are not effectively targeted by current treatments. This may be achieved by detecting LSCs that are generally enriched in the $CD34^+CD38^-$ compartment.

In one optional embodiment, the individual has also been tested for the presence of certain immune cells. For example, the in vitro method may be used to quantify the number of immune cells (such as B cells, T cells and NK cells) that express SLAMF6.

For example, in one embodiment the method may further comprise an additional step performing FACS on the bone marrow or peripheral blood sample to identify B cell, T cell and/or NK cell markers with SLAMF6 co-expression, e.g. using CD19 expression as a marker to identify B cells or CD3 expression as a marker to identify T cells. The skilled person would be aware of FACS panels for these cell subsets.

In one embodiment, the method further comprises the step of treating a patient diagnosed as having a neoplastic haematologic disorder with an effective therapy therefor, for example chemotherapy, biological therapy (e.g. immunotherapy), targeted therapy, radiation therapy and/or stem cell or bone marrow transplant.

In one embodiment of the above method aspects of the invention, the neoplastic hematologic disorder is a leukemia. More specifically, the neoplastic hematologic disorder may be selected from the group consisting of chronic myeloid leukemia (CML), myeloproliferative disorders (MPD), myelodysplastic syndrome (MDS), acute lymphoblastic leukemia (ALL) and acute myeloid leukemia (AML). In one particularly preferred embodiment, the neoplastic hematologic disorder is acute myeloid leukemia (AML).

In a further embodiment, the neoplastic hematologic disorder may be associated with cells comprising a TP53 mutation.

However, it will be appreciated by persons skilled in the art that the agents of the invention may also be used in the treatment and/or diagnosis of neoplastic hematologic disorders which are not associated with cells comprising a TP53 mutation (but nevertheless show upregulation of SLAMF6). Such neoplastic hematologic disorders which are associated with cells which do not comprise a TP53 mutation may include the myelodysplastic syndromes (MDS) and myeloproliferative disorders (MPD) such as polycythemia vera (PV), essential thrombocytosis (ET) and myelofibrosis (MF).

Preferred, non-limiting examples which embody certain aspects of the invention will now be described, with reference to the following figures:

FIG. 1: Arrayed antibody screen shows SLAMF6 to be specifically expressed in TP53 mutated AML cells.

A: Gates used to define immature, viable, single cells with a $CD3^-CD19^-CD34^+CD38^-$ phenotype. B: Waterfall plot of median difference in MFI between AML and NBM within the $CD3^-CD19^-CD34^+CD38^-$ compartment. Three TP53 mutated AML and three NBM samples were analyzed. Markers with high expression in NBM are excluded from this plot. C: Spearman correlation of MFI between biological replicates from antibody screen for NBM #2 and NBM #3. 14 values not depicted due to value of zero or negative values and logarithmic axes. D: Spearman correlation of MFI between biological replicates from antibody screen for AML #83 and AML #80. 42 values not depicted due to value of zero or negative values. E: Top ranked cell surface markers based on difference in $AML^{MFI}$ and $NBM^{MFI}$ from three separate analyses of TP53 mutated AML and NBM samples. Median MFI is plotted for AML (black bars) and NBM (white bars).

FIG. 2: Flow cytometric validation of SLAMF6 overexpression in TP53 mutated AML cells.

Eight novel cell surface receptors with high ranking in the screen were analyzed in separate experiments. Representative histograms of an AML (far left), an NBM sample (middle left), percent positive cells (middle right), and MFI (far right) for each marker within the $CD34^+CD38^-$ population are shown. Mean and standard deviation are shown.

FIG. 3: SLAMF6 is upregulated in immature TP53 mutated AML cells.

A: AML SLAMF6 expression is higher in phenotypically immature $CD34^+CD38^+$ and $CD34^+CD38^-$ populations. Histograms from a representative sample (AML 48) shown. B: NBM SLAMF6 expression is detected in mature $CD34^-CD38^-$ and $CD34^-CD38^+$ NBM population but low or absent in more immature $CD34^+CD38^+$ and $CD34^+CD38^-$ respectively. Histograms from one representative sample shown. C: SLAMF6 gene expression levels are higher in TP53 mutated AML MNC cells than in stem and progenitor populations of normal bone marrow. CMP: common myeloid progenitor, GMP: granulocyte-macrophage progenitor, MEP: megakaryocyte-erythroid progenitor, LMPP: lymphoid-primed multipotent progenitor, MPP: multipotent progenitor, HSC: hematopoietic stem cells. D: $CD3^+$ T cells and $CD19^+$ B cells in AML samples retain their SLAMF6 expression in all tested genetic subgroups of AML. AML 66 is shown as a representative example.

FIG. 4: SLAMF6 expression levels in genetic subtypes of AML.

A: SLAMF6 gene expression levels are significantly higher in TP53 mutated AML samples (n=14) compared to AML samples of other genetic subtypes (n=151) in the publicly available TCGA dataset. B: SLAMF6 is expressed in the leukemic $CD19^-CD3^-$ population in a TP53 mutated CD34 negative AML sample. C: SLAMF6 is expressed on leukemic cells in AML 33, AML 34 and on a subpopulation of MDS144. D: SLAMF6 is possibly expressed at low levels on leukemic cells in AML 32, MDS35 and AML 66. E: No expression of SLAMF6 could be detected on the leukemic cells in AML 21, AML 28, MDS70 or AML 94.

FIG. 5: SLAMF6 expression is retained in AML patient derived xenografts and anti-SLAMF6 antibodies induce ADCC killing of KG1 cells.

A: Histograms showing SLAM6 expression in the AML cell lines KG1 and K562 but not OCI-AML 3. B: Specific SLAMF6 mediated ADCC killing of KG1 cells (black, solid line) compared to isotype control (grey, dashed line). Mean effect and standard deviation of three different NK donors are shown, results are normalization to base line killing by the NK cells. C: Xenografts of TP53 mutated AML show high levels of SLAMF6 expression within the human $CD45^+$ $CD34^+CD38^-$ compartment. Spleen from secondary an AML 48 xenograft is shown as a representative example with 99% $CD45^+$ human cells, 45% $CD34^+CD38^-$ cells and a high SLAMF6 expression.

FIG. 6: A SLAMF6 antibody mediates killing of AML patient cells by ADCC.

A. Specific killing of AML patient cells ex vivo by a SLAMF6 antibody eliciting NK cell recruitment and killing through ADCC. Values indicate the average number of remaining viable target cells+/−SEM after treatment with a SLAMF6 antibody (black, solid line) or an isotype control (grey, dashed line), normalized to a control without antibody. For AML-83, cells were passaged in vivo for two generations for LSC enrichment before being subjected to ADCC. One NK cell donor was used for PDX-83 and four for AML-61. B. Protein expression of SLAMF6 on the AML patient cells.

Figure 7:
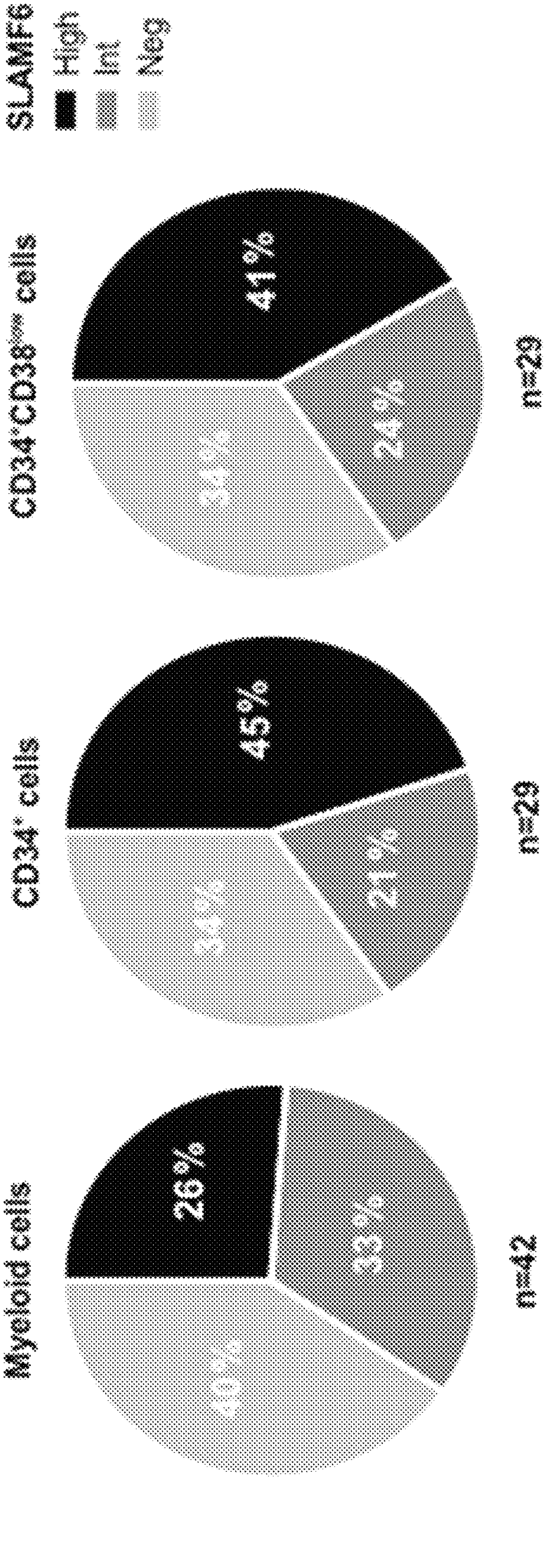

FIG. 7: SLAMF6 expression on AML samples.

SLAMF6 as determined by flow cytometry is expressed on a majority of AML samples, in particular in the CD34+ CD38low leukemic stem cell containing fraction. Samples were classified as "High" when containing >50% SLAMF6 positive cells, "Intermediate" when containing 10-50% SLAMF6 positive cells and "Negative" when containing <10% SLAMF6 positive cells.

Figure 8:
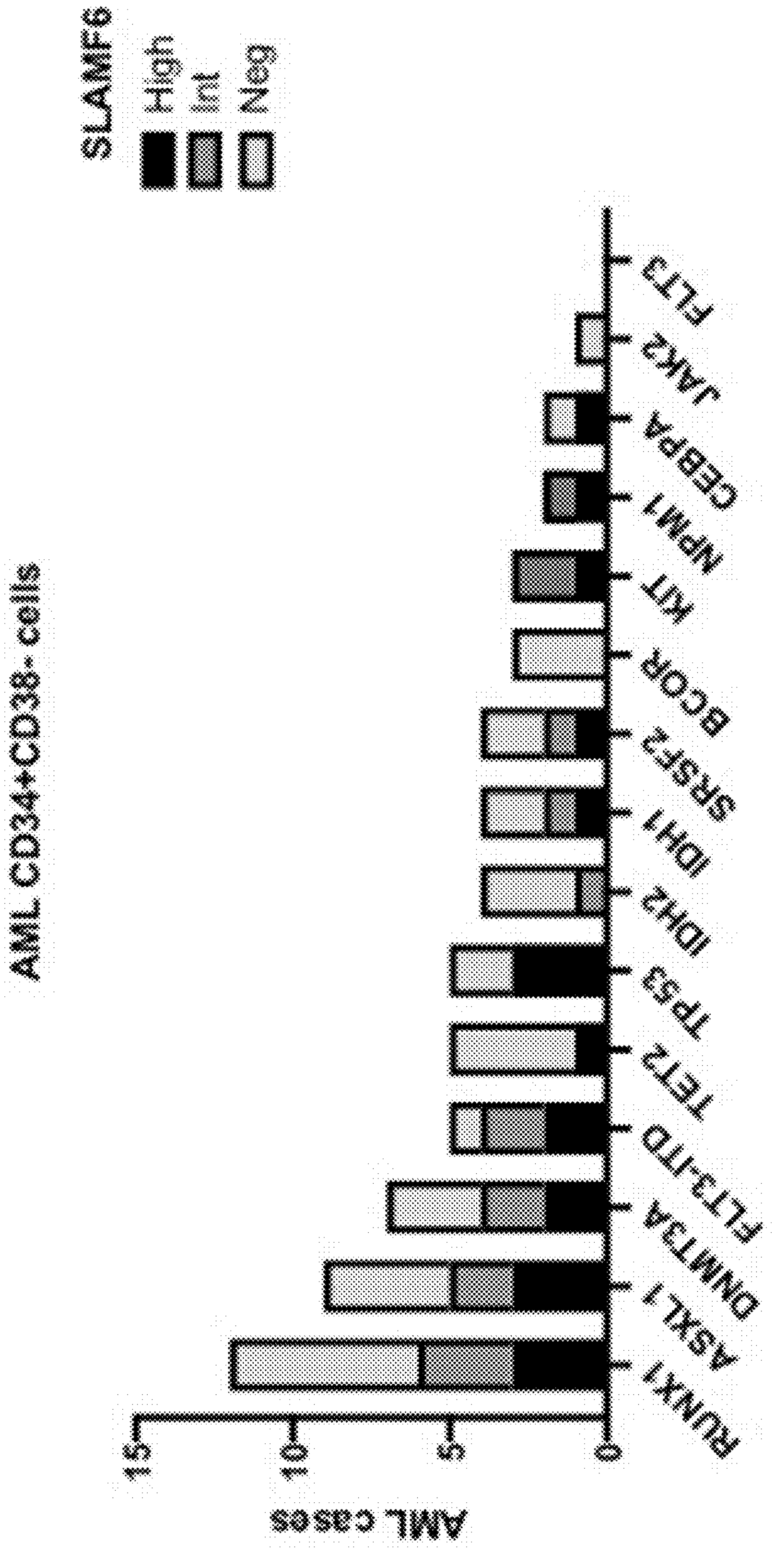

FIG. 8: SLAMF6 expression on leukemic stem cells from AML samples.

SLAMF6 as determined by flow cytometry is expressed on leukemic stem cells from AML samples with a large variety of mutational backgrounds.

Figure 9:
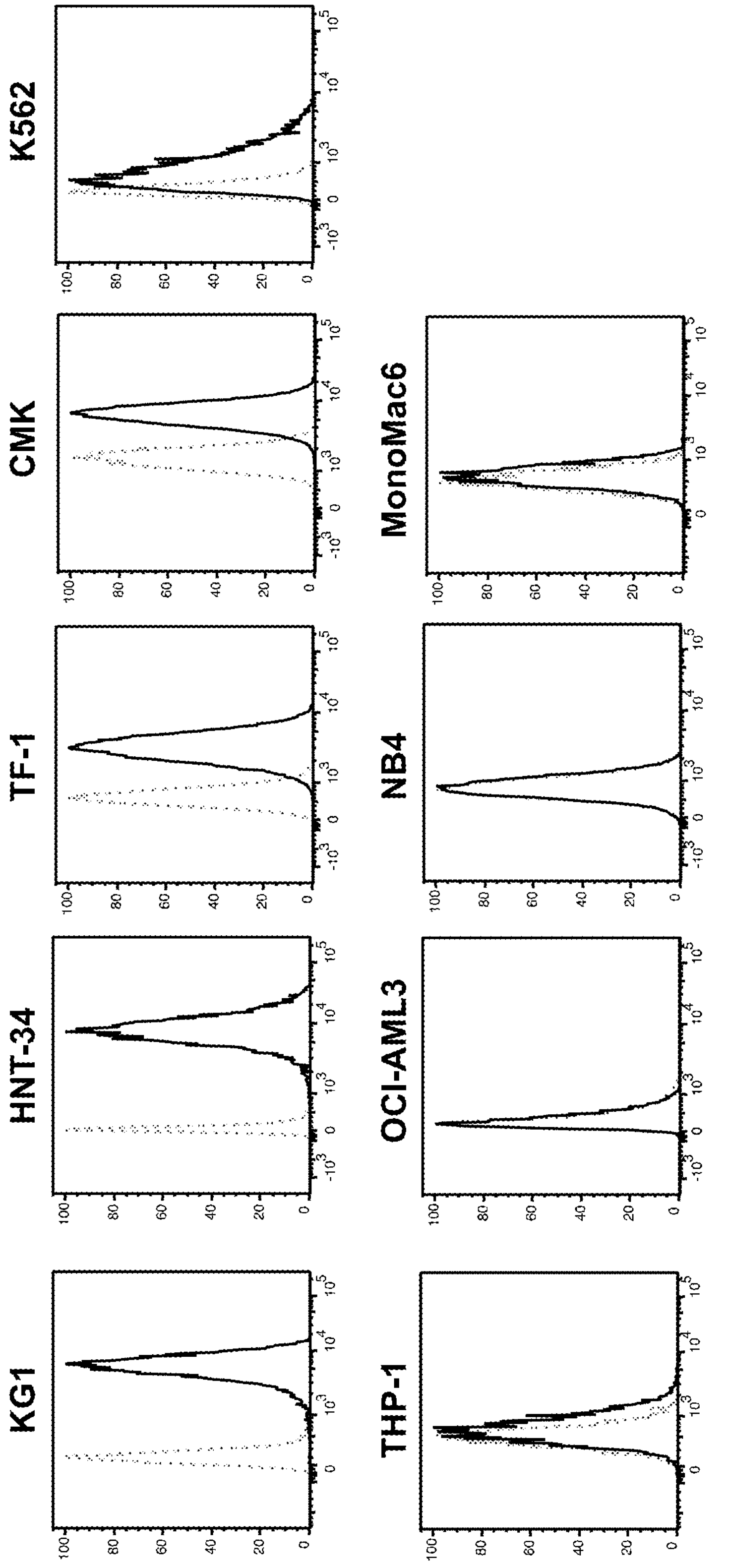

FIG. 9: SLAMF6 expression on cell lines.

SLAMF6 as determined by flow cytometry is expressed on the AML cell lines KG1 (DSMZ #ACC14), HNT-34 (DSMZ #ACC600), TF-1 (DSMZ #ACC334), CMK (DSMZ #ACC392), and K562 (DSMZ #ACC10) but not on THP-1 (DSMZ #ACC16), OCI-AML 3 (DSMZ #ACC582), NB4 (DSMZ #ACC207), or MonoMac6 (DSMZ #ACC124).

Figure 10:
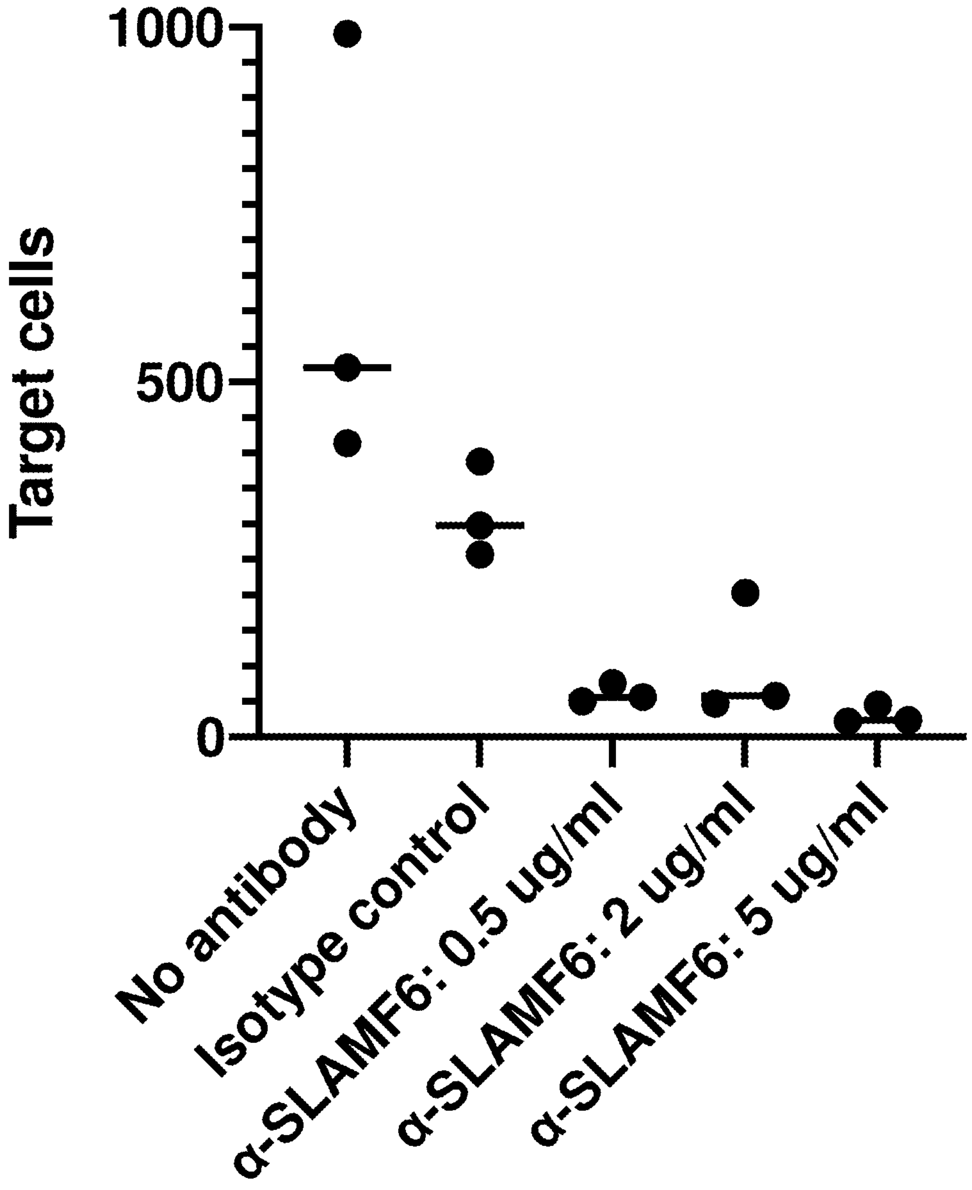

FIG. 10. Antibody-mediated activation of SLAMF6 on T cells promotes killing of AML cells.

T cell-mediated killing of HNT-34 cells, measured as the total number of target cells 72 h after seeding of T cells and HNT-34 target cells at a 4:1 ratio, with the addition of an activating SLAMF6 antibody or an isotype control.

FIG. 11. SLAMF6 mediates resistance to T cell killing.

T cell-mediated killing of SLAMF6 knockout cells, measured as the total number of target cells (A), T cells (B) and activated T cells (C) three days after seeding of T cells and KG-1 target cells at a 4:1 ratio. Dashed line indicates the number of cells seeded. (D) Validation of SLAMF6 knockout by FACS.

EXAMPLE 1

SLAMF6 is a Cell Surface Biomarker for Acute Myeloid Leukemia Stem Cells

Summary

Therapeutic strategies for acute myeloid leukemia (AML) aiming at achieving a permanent cure of the disorder, will require a full eradication of the AML stem cells. The AML stem cells, sharing the capacity to self-renew with normal hematopoietic stem cells (HSCs), represent a small population of leukemic cells that so far have been indistinguishable from normal (HSCs) using cell surface markers. One strategy to target the AML stem cell would be to identify a cell surface biomarker for AML stem cells, to which future therapeutic antibodies could be directed. In this study, SLAMF6 was identified in a surface marker screen of TP53-mutated AML as commonly expressed on primitive $CD34^+CD38^-$ AML cells but not on corresponding normal cells. Furthermore, targeting of SLAMF6 was shown to induce killing of AML cells through antibody-dependent cellular cytotoxicity (ADCC).

This study thus identifies SLAMF6 as a novel cell surface biomarker distinguishing AML stem cells from normal HSC and opens up new avenues for therapeutic and diagnostic strategies in AML. In addition to direct effects on the leukemia cell, targeting of SLAMF6 may also alter its interaction with immune cells to induce an anti-tumor response. Further, as SLAMF6 is also expressed on immune cells (B cells, T cells and NK cells), it is a suitable target for dual targeting on both pathological stem cells (e.g. leukemic stem cells) and immune cells (e.g. B cells, T cells and/or NK cells), whereby the immune cells may be activated to enhance elimination of the pathological stem cells. For example, the agent may be used to target pathological stem cells and B cells; or pathological stem cells, B cells and T cells; or pathological stem cells, NK cells and T cells, etc.

Introduction

To identify a cell surface biomarker for AML stem cells, the inventors performed an antibody screen and identified SLAMF6 as a novel candidate, being upregulated in primitive AML patient cells.

Materials and Methods

Patient Samples

Bone marrow and peripheral blood samples were collected after written informed consent in accordance to the Declaration of Helsinki. Samples were collected from patients with AML, myelodysplastic syndrome (MDS) or healthy controls. Mononuclear cells (MNC) were isolated using Lymphoprep (GE Healthcare Bio-Sciences AB, Sweden) and subsequently viably frozen. Patients included in the study and their clinical characteristics are shown in Table 1. The study was approved by a regional ethics committee in Lund (Dnr2011/289).

Cell Surface Marker Screen

Arrayed antibody libraries were prepared based on the LEGENDScreen system (BioLegend, USA), containing 362 PE-conjugated antibodies. Two different iterations of the LEGENDScreen (BioLegend, USA) were used, containing slightly different antibodies (#700001 had 34 antibodies not included in #700007 which contained 61 antibodies not included in #700001; for a complete list, see Table 2). Antibodies targeting IL1RAP, previously shown to be upregulated on AML stem cells,[9, 22, 23] and CD177, suggested to be upregulated on the mRNA level in AML (data not shown), were added to the arrays. Antibodies against CD3, CD19, CD34, CD38 and the viability marker 7AAD were added to each well of the 96-well U-shaped plates. All antibodies and reagents used are listed in Table 3. Bone marrow mononuclear cells from TP53 mutated AML samples (n=3) or healthy normal bone marrow (NBM) donors (n=3) were added and incubated at 4° C. for 20 minutes and subsequently washed and resuspended. Flow cytometry read out was performed using an LSR Fortessa with an HTS (BD Bioscience, USA). Median fluorescent intensity (MFI) for each marker within the $7AAD^-CD3^-CD19^-CD34^+CD38^-$ fraction were used to compare expression between AML and NBM (FIG. 1A). First, markers with a high expression within the $7AAD^-CD3^-CD19^-CD34^+CD38^-$ fraction of NBM samples (>10% positive or MFI>10000) were excluded. Next, marker $NBM^{MFI}$ were subtracted from paired $AML^{MFI}$ and markers were ranked according to median MFI from three separate experiments. The corresponding analyses and ranking were performed using the quota of $AML^{MFI}/NBM^{MFI}$. The two ranking systems were combined to produce a top list of specifically upregulated cell surface markers (Table 4).

TABLE 1

| AML Patient Characteristics | | | | | | | | | |
|---|---|---|---|---|---|---|---|---|---|
| Pat# | Gender | Disease | FAB | ELN | Karyotype | Mutations | CD34 | SLAMF6 | SLAMF6 in CD34+ CD38− |
| 21 | M | AML-D | M2 | IR | 46, XY | IDH2, STAG2, BCOR | pos | neg | neg |
| 28 | M | SAML-D | M2 | IR | 46, XY | NPM1, FLT3-ITD, TET2 | neg | neg | — |
| 32 | M | AML-D | M2 | HR | 47, XY, +13 | RUNX1, ASXL1, | pos | low | low |
| 33 | F | SAML-R | M4 | IR | 46, XX | DNMT3A, NPM1, FLT3-ITD, IDH1, CEBPA | neg | pos | — |
| 34 | F | AML-D | M5 | IR | 46, XX | DNMT3A, IDH1, NRAS, CEBPA | pos | pos | pos |
| 35 | F | MDS RAEB-2 | — | — | 46, XX | RUNX1, ASXL1, DNMT3A, IDH2 | pos | low | low |
| 48 | F | tAML-D | M2 | HR | Complex1 | TP53 | pos | pos | pos |
| 66 | M | SAML-D | M2 | LR | 46, XY | IDH1, NPM1, JAK2, CEBPA | neg | low | — |
| 70 | M | MPN/MDS | — | — | 46, XY | RUNX1, ASXL1, TET2, | neg | neg | — |
| 80 | M | AML-D | M2 | HR | Complex2 | TP53 | pos | pos | pos |
| 83 | M | SAML-D | M2 | HR | Complex3 | TP53, TET2, NF1 | pos | pos | pos |
| 94 | M | AML-D | M0 | HR | 47, XY, +10 | DNMT3A, IDH1, FLT3-ITD, RUNX1, BCOR, STAG2 | pos | neg | neg |
| 144 | F | MPN/MDS | — | — | 47, XX, +8 | RUNX1, ASXL1, TET2, BCOR | neg | pos | — |
| 155 | M | AML-D | M5 | HR | Complex4 | TP53, FLT3 | neg | pos | — |

Abbreviations:
D: diagnosis,
R: relapse,
sAML: secondary AML,
tAML: therapy-related AML,
ELN: European Leukemia net risk classification 2017,
IR: intermediate risk,
HR: high risk,
CD34 pos: ≥15% CD34+ cells
Complex1: 43-47, XX, del(5)(q13q33), der(8)t(8;12)(p22;p13), add(11)(p15), −12, add(13)(p11), −18, del(20)(q11), add(22)(q13), +mar
Complex2: 48, XXYc, +i(12)(p10), der(17)t(13;17)(q1?4;p1?3)
Complex3: 45, XY, der(13;14)(q10;q10)/42-44, idem, −5, −7, −9, −10, −11, ?hsr(11)(q23), −14, −16, −20, +4mar
Complex4: 47, XY, +8, t(9;11)(p21;q23)/46-47, idem, der(9)del(9)(p12)del(9)(q12), der(17)t(9;17)(q31;p13)/46-47, idem, der(7;10)(q10;q10), +add(8)(p11)

TABLE 2

| Antibodies included in the screen | | | | | |
|---|---|---|---|---|---|
| Screen Iteration 70001 | | | | | |
| Plate | Well ID | Specificity | Clone | Isotype | Cat# |
| Plate 1 | A01 | Blank | | | |
| Plate 1 | A02 | CD1a | HI149 | Mouse IgG1, κ | 300106 |
| Plate 1 | A03 | CD1b | SN13 (K5- 1B8) | Mouse IgG1, κ | 329108 |
| Plate 1 | A04 | CD1c | L161 | Mouse IgG1, κ | 331506 |
| Plate 1 | A05 | CD1d | 51.1 | Mouse IgG2b, κ | 350306 |
| Plate 1 | A06 | CD2 | RPA-2.10 | Mouse IgG1, κ | 300208 |
| Plate 1 | A07 | CD3 | HIT3a | Mouse IgG2a, κ | 300308 |
| Plate 1 | A08 | CD4 | RPA-T4 | Mouse IgG1, κ | 300508 |
| Plate 1 | A09 | CD5 | UCHT2 | Mouse IgG1, κ | 300608 |
| Plate 1 | A10 | CD6 | BL-CD6 | Mouse IgG1, κ | 313906 |
| Plate 1 | A11 | CD7 | CD7-6B7 | Mouse IgG2a, κ | 343106 |
| Plate 1 | A12 | CD8a | HIT8a | Mouse IgG1, κ | 300908 |
| Plate 1 | B01 | CD9 | HI9a | Mouse IgG1, κ | 312106 |
| Plate 1 | B02 | CD10 | HI10a | Mouse IgG1, κ | 312204 |
| Plate 1 | B03 | CD11a | HI111 | Mouse IgG1, κ | 301208 |
| Plate 1 | B04 | CD11b | ICRF44 | Mouse IgG1, κ | 301306 |
| Plate 1 | B05 | CD11b (activated) | CBRM1/5 | Mouse IgG1, κ | 301406 |
| Plate 1 | B06 | CD11c | 3.9 | Mouse IgG1, κ | 301606 |
| Plate 1 | B07 | CD13 | WM15 | Mouse IgG1, κ | 301704 |
| Plate 1 | B08 | CD14 | M5E2 | Mouse IgG2a, κ | 301806 |
| Plate 1 | B09 | CD15 (SSEA-1) | W6D3 | Mouse IgG1, κ | 323006 |
| Plate 1 | B10 | CD16 | 3G8 | Mouse IgG1, κ | 302008 |
| Plate 1 | B11 | CD18 | TS1/18 | Mouse IgG1, κ | 302108 |
| Plate 1 | B12 | CD19 | HIB19 | Mouse IgG1, κ | 302208 |
| Plate 1 | C01 | CD20 | 2H7 | Mouse IgG2b, κ | 302306 |
| Plate 1 | C02 | CD21 | Bu32 | Mouse IgG1, κ | 354904 |
| Plate 1 | C03 | CD22 | HIB22 | Mouse IgG1, κ | 302506 |
| Plate 1 | C04 | CD23 | EBVCS-5 | Mouse IgG1, κ | 338508 |

TABLE 2-continued

| Antibodies included in the screen | | | | | |
|---|---|---|---|---|---|
| Plate 1 | C05 | CD24 | ML5 | Mouse IgG2a, κ | 311106 |
| Plate 1 | C06 | CD25 | BC96 | Mouse IgG1, κ | 302606 |
| Plate 1 | C07 | CD26 | BA5b | Mouse IgG2a, κ | 302706 |
| Plate 1 | C08 | CD27 | O323 | Mouse IgG1, κ | 302808 |
| Plate 1 | C09 | CD28 | CD28.2 | Mouse IgG1, κ | 302908 |
| Plate 1 | C10 | CD29 | TS2/16 | Mouse IgG1, κ | 303004 |
| Plate 1 | C11 | CD30 | BY88 | Mouse IgG1, κ | 333906 |
| Plate 1 | C12 | CD31 | WM59 | Mouse IgG1, κ | 303106 |
| Plate 1 | D01 | CD32 | FUN-2 | Mouse IgG2b, κ | 303206 |
| Plate 1 | D02 | CD33 | WM53 | Mouse IgG1, κ | 303404 |
| Plate 1 | D03 | CD34 | 581 | Mouse IgG1, κ | 343506 |
| Plate 1 | D04 | CD35 | E11 | Mouse IgG1, κ | 333406 |
| Plate 1 | D05 | CD36 | 5-271 | Mouse IgG2a, κ | 336206 |
| Plate 1 | D06 | CD38 | HIT2 | Mouse IgG1, κ | 303506 |
| Plate 1 | D07 | CD39 | A1 | Mouse IgG1, κ | 328208 |
| Plate 1 | D08 | CD40 | HB14 | Mouse IgG1, κ | 313006 |
| Plate 1 | D09 | CD41 | HIP8 | Mouse IgG1, κ | 303706 |
| Plate 1 | D10 | CD42b | HIP1 | Mouse IgG1, κ | 303906 |
| Plate 1 | D11 | CD43 | CD43-10G7 | Mouse IgG1, κ | 343204 |
| Plate 1 | D12 | CD44 | BJ18 | Mouse IgG1, κ | 338808 |
| Plate 1 | E01 | CD45 | HI30 | Mouse IgG1, κ | 304008 |
| Plate 1 | E02 | CD45RA | HI100 | Mouse IgG2b, κ | 304108 |
| Plate 1 | E03 | CD45RB | MEM-55 | Mouse IgG2b, κ | 310204 |
| Plate 1 | E04 | CD45RO | UCHL1 | Mouse IgG2a, κ | 304206 |
| Plate 1 | E05 | CD46 | TRA-2-10 | Mouse IgG1 | 352402 |
| Plate 1 | E06 | CD47 | CC2C6 | Mouse IgG1, κ | 323108 |
| Plate 1 | E07 | CD48 | BJ40 | Mouse IgG1, κ | 336708 |
| Plate 1 | E08 | CD49a | TS2/7 | Mouse IgG1, κ | 328304 |
| Plate 1 | E09 | CD49c | ASC-1 | Mouse IgG1, κ | 343804 |
| Plate 1 | E10 | CD49d | 9F10 | Mouse IgG1, κ | 304304 |
| Plate 1 | E11 | CD49e | NKI-SAM-1 | Mouse IgG2b, κ | 328010 |
| Plate 1 | E12 | CD49f | GoH3 | Rat IgG2a, κ | 313612 |
| Plate 1 | F01 | CD50 (ICAM-3) | CBR-IC3/1 | Mouse IgG1, κ | 330005 |
| Plate 1 | F02 | CD51 | NKI-M9 | Mouse IgG2a, κ | 327910 |
| Plate 1 | F03 | CD51/61 | 23C6 | Mouse IgG1, κ | 304406 |
| Plate 1 | F04 | CD52 | HI186 | Mouse IgG2b, κ | 316006 |
| Plate 1 | F05 | CD53 | HI29 | Mouse IgG1, κ | 325406 |
| Plate 1 | F06 | CD54 | HA58 | Mouse IgG1, κ | 353106 |
| Plate 1 | F07 | CD55 | JS11 | Mouse IgG1, κ | 311308 |
| Plate 1 | F08 | CD56 (NCAM) | HCD56 | Mouse IgG1, κ | 318306 |
| Plate 1 | F09 | CD57 | HCD57 | Mouse IgM, κ | 322312 |
| Plate 1 | F10 | CD58 | TS2/9 | Mouse IgG1, κ | 330905 |
| Plate 1 | F11 | CD59 | p282(H19) | Mouse IgG2a, κ | 304708 |
| Plate 1 | F12 | CD61 | VI-PL2 | Mouse IgG1, κ | 336406 |
| Plate 1 | G01 | CD62E | HAE-1f | Mouse IgG1, κ | 336008 |
| Plate 1 | G02 | CD62L | DREG-56 | Mouse IgG1, κ | 304806 |
| Plate 1 | G03 | CD62P (P-Selectin) | AK4 | Mouse IgG1, κ | 304906 |
| Plate 1 | G04 | CD63 | H5C6 | Mouse IgG1, κ | 353004 |
| Plate 1 | G05 | CD64 | 10.1 | Mouse IgG1, κ | 305008 |
| Plate 1 | G06 | CD66a/c/e | ASL-32 | Mouse IgG2b, κ | 342304 |
| Plate 1 | G07 | CD66b | G10F5 | Mouse IgM, κ | 305106 |
| Plate 1 | G08 | CD69 | FN50 | Mouse IgG1, κ | 310906 |
| Plate 1 | G09 | CD70 | 113-16 | Mouse IgG1, κ | 355104 |
| Plate 1 | G10 | CD71 | CY1G4 | Mouse IgG2a, κ | 334106 |
| Plate 1 | G11 | CD73 | AD2 | Mouse IgG1, κ | 344004 |
| Plate 1 | G12 | CD74 | LN2 | Mouse IgG1, κ | 326808 |
| Plate 1 | H01 | CD79b | CB3-1 | Mouse IgG1, κ | 341404 |
| Plate 1 | H02 | CD80 | 2D10 | Mouse IgG1, κ | 305208 |
| Plate 1 | H03 | CD81 | 5A6 | Mouse IgG1, κ | 349506 |
| Plate 1 | H04 | CD82 | ASL-24 | Mouse IgG1, κ | 342104 |
| Plate 1 | H05 | CD83 | HB15e | Mouse IgG1, κ | 305308 |
| Plate 1 | H06 | CD84 | CD84.1.21 | Mouse IgG2a, κ | 326008 |
| Plate 1 | H07 | CD85a (ILT5) | MKT5.1 | Rat IgG2a, κ | 337704 |
| Plate 1 | H08 | CD85d (ILT4) | 42D1 | Rat IgG2a, κ | 338706 |
| Plate 1 | H09 | CD85g (ILT7) | 17G10.2 | Mouse IgG1, κ | 326408 |
| Plate 1 | H10 | CD85h (ILT1) | 24 | Mouse IgG2b, κ | 337904 |
| Plate 1 | H11 | CD85j (ILT2) | GHI/75 | Mouse IgG2b, κ | 333708 |
| Plate 1 | H12 | CD85k (ILT3) | ZM4.1 | Mouse IgG1, κ | 333008 |
| Plate 2 | A01 | Blank | | | |
| Plate 2 | A02 | CD86 | IT2.2 | Mouse IgG2b, κ | 305406 |
| Plate 2 | A03 | CD87 | VIM5 | Mouse IgG1, κ | 336906 |
| Plate 2 | A04 | CD88 | S5/1 | Mouse IgG2a, κ | 344304 |
| Plate 2 | A05 | CD89 | A59 | Mouse IgG1, κ | 354104 |
| Plate 2 | A06 | CD90 (Thy1) | 50000000000 | Mouse IgG1, κ | 328110 |
| Plate 2 | A07 | CD93 | VIMD2 | Mouse IgG1, κ | 336108 |
| Plate 2 | A08 | CD94 | DX22 | Mouse IgG1, κ | 305506 |
| Plate 2 | A09 | CD95 | DX2 | Mouse IgG1, κ | 305608 |
| Plate 2 | A10 | CD96 | NK92.39 | Mouse IgG1, κ | 338406 |

TABLE 2-continued

| Antibodies included in the screen | | | | | |
|---|---|---|---|---|---|
| Plate 2 | A11 | CD97 | VIM3b | Mouse IgG1, κ | 336308 |
| Plate 2 | A12 | CD99 | HCD99 | Mouse IgG2a, κ | 318008 |
| Plate 2 | B01 | CD100 | A8 | Mouse IgG1, κ | 328408 |
| Plate 2 | B02 | CD101 (BB27) | BB27 | Mouse IgG1, κ | 331006 |
| Plate 2 | B03 | CD102 | CBR-IC2/2 | Mouse IgG2a, κ | 328506 |
| Plate 2 | B04 | CD103 | Ber-ACT8 | Mouse IgG1, κ | 350206 |
| Plate 2 | B05 | CD104 | 58XB4 | Mouse IgG2a, κ | 327808 |
| Plate 2 | B06 | CD105 | 43A3 | Mouse IgG1, κ | 323206 |
| Plate 2 | B07 | CD106 | STA | Mouse IgG1, κ | 305806 |
| Plate 2 | B08 | CD107a (LAMP-1) | H4A3 | Mouse IgG1, κ | 328608 |
| Plate 2 | B09 | CD108 | MEM-150 | Mouse IgM, κ | 315704 |
| Plate 2 | B10 | CD109 | W7C5 | Mouse IgG1, κ | 323306 |
| Plate 2 | B11 | CD111 | R1.302 | Mouse IgG1, κ | 340404 |
| Plate 2 | B12 | CD112 (Nectin-2) | TX31 | Mouse IgG1, κ | 337410 |
| Plate 2 | C01 | CD114 | LMM741 | Mouse IgG1, κ | 346106 |
| Plate 2 | C02 | CD115 | 9-4D2-1E4 | Rat IgG1, κ | 347304 |
| Plate 2 | C03 | CD116 | 4H1 | Mouse IgG1, κ | 305908 |
| Plate 2 | C04 | CD117 (c-kit) | 104D2 | Mouse IgG1, κ | 313204 |
| Plate 2 | C05 | CD119 (IFN-g Rd chain) | GIR-208 | Mouse IgG1, κ | 308606 |
| Plate 2 | C06 | CD122 | TU27 | Mouse IgG1, κ | 339006 |
| Plate 2 | C07 | CD123 | 6H6 | Mouse IgG1, κ | 306006 |
| Plate 2 | C08 | CD124 | G077F6 | Mouse IgG2a, κ | 355004 |
| Plate 2 | C09 | CD126 (IL-6Rα) | UV4 | Mouse IgG1, κ | 352804 |
| Plate 2 | C10 | CD127 (IL-7Rα) | A019D5 | Mouse IgG1, κ | 351304 |
| Plate 2 | C11 | CD129 (IL-9 R) | AH9R7 | Mouse IgG2b, κ | 310404 |
| Plate 2 | C12 | CD131 | 1C1 | Mouse IgG1, κ | 306104 |
| Plate 2 | D01 | CD132 | TUGh4 | Rat IgG2b, κ | 338606 |
| Plate 2 | D02 | CD134 | Ber-ACT35 (ACT35) | Mouse IgG1, κ | 350004 |
| Plate 2 | D03 | CD135 | BV10A4H2 | Mouse IgG1, κ | 313306 |
| Plate 2 | D04 | CD137 (4-1BB) | 4B4-1 | Mouse IgG1, κ | 309804 |
| Plate 2 | D05 | CD137L (4-1BB Ligand) | 5F4 | Mouse IgG1, κ | 311504 |
| Plate 2 | D06 | CD138 | DL-101 | Mouse IgG1, κ | 352306 |
| Plate 2 | D07 | CD140a | 16A1 | Mouse IgG1, κ | 323506 |
| Plate 2 | D08 | CD140b | 18A2 | Mouse IgG1, κ | 323606 |
| Plate 2 | D09 | CD141 | M80 | Mouse IgG1, κ | 344104 |
| Plate 2 | D10 | CD143 | 5-369 | Mouse IgG1, κ | 344204 |
| Plate 2 | D11 | CD144 | BV9 | Mouse IgG2a, κ | 348506 |
| Plate 2 | D12 | CD146 | SHM-57 | Mouse IgG2a, κ | 342004 |
| Plate 2 | E01 | CD148 | A3 | Mouse IgG1, κ | 328708 |
| Plate 2 | E02 | CD150 (SLAM) | A12 (7D4) | Mouse IgG1, κ | 306308 |
| Plate 2 | E03 | CD152 | L3D10 | Mouse IgG1, κ | 349906 |
| Plate 2 | E04 | CD154 | 24-31 | Mouse IgG1, κ | 310806 |
| Plate 2 | E05 | CD155 (PVR) | SKII.4 | Mouse IgG1, κ | 337610 |
| Plate 2 | E06 | CD156c (ADAM10) | SHM14 | Mouse IgG1, κ | 352704 |
| Plate 2 | E07 | CD158a/h | HP-MA4 | Mouse IgG2b, κ | 339506 |
| Plate 2 | E08 | CD158b (KIR2DL2/L3) | DX27 | Mouse IgG2a, κ | 312606 |
| Plate 2 | E09 | CD158d | mAb 33 (33) | Mouse IgG1, κ | 347006 |
| Plate 2 | E10 | CD158e1 (KIR3DL1) | DX9 | Mouse IgG1, κ | 312708 |
| Plate 2 | E11 | CD158f | UP-R1 | Mouse IgG1, κ | 341304 |
| Plate 2 | E12 | CD161 | HP-3G10 | Mouse IgG1, κ | 339904 |
| Plate 2 | F01 | CD162 | KPL-1 | Mouse IgG1, κ | 328806 |
| Plate 2 | F02 | CD163 | GHI/61 | Mouse IgG1, κ | 333606 |
| Plate 2 | F03 | CD164 | 67D2 | Mouse IgG1, κ | 324808 |
| Plate 2 | F04 | CD165 | SN2 (N6- D11) | Mouse IgG1, κ | 329010 |
| Plate 2 | F05 | CD166 | 3A6 | Mouse IgG1, κ | 343904 |
| Plate 2 | F06 | CD167a (DDR1) | 51D6 | Mouse IgG3, κ | 334006 |
| Plate 2 | F07 | CD169 | 7-239 | Mouse IgG1, κ | 346004 |
| Plate 2 | F08 | CD170 (Siglec-5) | 1A5 | Mouse IgG1, κ | 352004 |
| Plate 2 | F09 | CD172a (SIRPa) | SE5A5 | Mouse IgG1, κ | 323806 |
| Plate 2 | F10 | CD172b (SIRPb) | B4B6 | Mouse IgG1, κ | 323906 |
| Plate 2 | F11 | CD172g (SIRPg) | LSB2.20 | Mouse IgG1, κ | 336606 |
| Plate 2 | F12 | CD178 (Fas-L) | NOK-1 | Mouse IgG1, κ | 306407 |
| Plate 2 | G01 | CD179a | HSL96 | Mouse IgG1, κ | 347404 |
| Plate 2 | G02 | CD179b | HSL11 | Mouse IgG1, κ | 349804 |
| Plate 2 | G03 | CD180 (RP105) | MHR73-11 | Mouse IgG1, κ | 312906 |
| Plate 2 | G04 | CD181 (CXCR1) | 8F1/CXCR1 | Mouse IgG2b, κ | 320608 |
| Plate 2 | G05 | CD182 (CXCR2) | 5E8/CXCR2 | Mouse IgG1, κ | 320706 |
| Plate 2 | G06 | CD183 | G025H7 | Mouse IgG1, κ | 353706 |
| Plate 2 | G07 | CD184 (CXCR4) | 12G5 | Mouse IgG2a, κ | 306506 |
| Plate 2 | G08 | CD193 (CCR3) | 500000000 | Mouse IgG2b, κ | 310706 |
| Plate 2 | G09 | CD195 (CCR5) | T21/8 | Mouse IgG1, κ | 321406 |
| Plate 2 | G10 | CD196 | G034E3 | Mouse IgG2b, κ | 353410 |
| Plate 2 | G11 | CD197 (CCR7) | G043H7 | Mouse IgG2a, κ | 353204 |
| Plate 2 | G12 | CD200 (OX2) | OX-104 | Mouse IgG1, κ | 329206 |
| Plate 2 | H01 | CD200 R | OX-108 | Mouse IgG1, κ | 329306 |
| Plate 2 | H02 | CD201 (EPCR) | RCR-401 | Rat IgG1, κ | 351904 |

TABLE 2-continued

Antibodies included in the screen

| | | | | | |
|---|---|---|---|---|---|
| Plate 2 | H03 | CD202b (Tie2/Tek) | 33.1 (Ab33) | Mouse IgG1, κ | 334206 |
| Plate 2 | H04 | CD203c (E-NPP3) | NP4D6 | Mouse IgG1, κ | 324606 |
| Plate 2 | H05 | CD205 (DEC- 205) | HD30 | Mouse IgG1, κ | 342204 |
| Plate 2 | H06 | CD206 (MMR) | 15-2 | Mouse IgG1, κ | 321106 |
| Plate 2 | H07 | CD207 (Langerin) | 10E2 | Mouse IgG1, κ | 352204 |
| Plate 2 | H08 | CD209 (DC- SIGN) | 9E9A8 | Mouse IgG2a, κ | 330106 |
| Plate 2 | H09 | CD210 (IL- 10 R) | 3F9 | Rat IgG2a, κ | 308804 |
| Plate 2 | H10 | CD213a2 | SHM38 | Mouse IgG1, κ | 354404 |
| Plate 2 | H11 | CD215 (IL- 15Rα) | JM7A4 | Mouse IgG2b, κ | 330208 |
| Plate 2 | H12 | CD218a (IL-18Rα) | H44 | Mouse IgG1, κ | 313808 |
| Plate 3 | A01 | Blank | | | |
| Plate 3 | A02 | CD220 | B6.220 | Mouse IgG2b,__ | 352604 |
| Plate 3 | A03 | CD221 (IGF-1R) | 1H7/CD221 | Mouse IgG1,__ | 351806 |
| Plate 3 | A04 | CD226 (DNAM-1) | 11A8 | Mouse IgG1,__ | 338306 |
| Plate 3 | A05 | CD229 (Ly-9) | HLy-9.1.25 | Mouse IgG1,__ | 326108 |
| Plate 3 | A06 | CD231 (TALLA) | SN1a (M3-3D9) | Mouse IgG1,__ | 329406 |
| Plate 3 | A07 | CD235ab | HIR2 | Mouse IgG2b,__ | 306604 |
| Plate 3 | A08 | CD243 | UIC2 | Mouse IgG2a,__ | 348606 |
| Plate 3 | A09 | CD244 (2B4) | C1.7 | Mouse IgG1,__ | 329508 |
| Plate 3 | A10 | CD245 (p220/240) | DY12 | Mouse IgG1,__ | Inquire |
| Plate 3 | A11 | CD252 (OX40L) | 11C3.1 | Mouse IgG1,__ | 326308 |
| Plate 3 | A12 | CD253 (Trail) | RIK-2 | Mouse IgG1,__ | 308206 |
| Plate 3 | B01 | CD254 | MIH24 | Mouse IgG1,__ | 347504 |
| Plate 3 | B02 | CD255 (TWEAK) | CARL-1 | Mouse IgG3,__ | 308305 |
| Plate 3 | B03 | CD257 (BAFF, BLYS) | T7-241 | Mouse IgG1,__ | 318606 |
| Plate 3 | B04 | CD258 (LIGHT) | T5-39 | Mouse IgG2a,__ | 318706 |
| Plate 3 | B05 | CD261 (DR4, TRAIL-R1) | DJR1 | Mouse IgG1,__ | 307206 |
| Plate 3 | B06 | CD262 (DR5, TRAIL-R2) | DJR2-4 (7-8) | Mouse IgG1,__ | 307406 |
| Plate 3 | B07 | CD263 (DcR1, TRAIL-R3) | DJR3 | Mouse IgG1,__ | 307006 |
| Plate 3 | B08 | CD266 (Fn14) | ITEM-1 | Mouse IgG1,__ | 314004 |
| Plate 3 | B09 | CD267 (TACI) | 1A1 | Rat IgG2a,__ | 311906 |
| Plate 3 | B10 | CD268 (BAFF-R, BAFFR) | 11C1 | Mouse IgG1,__ | 316906 |
| Plate 3 | B11 | CD270 (HVEM) | 122 | Mouse IgG1,__ | 318806 |
| Plate 3 | B12 | CD271 | ME20.4 | Mouse IgG1,__ | 345106 |
| Plate 3 | C01 | CD273 (B7- DC, PD-L2) | 24F.10C12 | Mouse IgG2a,__ | 329606 |
| Plate 3 | C02 | CD274 (B7- H1, PD-L1) | 29E.2A3 | Mouse IgG2b,__ | 329706 |
| Plate 3 | C03 | CD275 (B7- H2, B7-RP1) | 9F.8A4 | Mouse IgG1,__ | 329806 |
| Plate 3 | C04 | CD276 | MIH42 | Mouse IgG1,__ | 351004 |
| Plate 3 | C05 | CD277 | BT3.1 | Mouse IgG1,__ | 342704 |
| Plate 3 | C06 | CD278 (ICOS) | C398.4A | Arm. Hamster IgG | 313508 |
| Plate 3 | C07 | CD279 (PD-1) | EH12.2H7 | Mouse IgG1,__ | 329906 |
| Plate 3 | C08 | CD282 (TLR2) | TL2.1 | Mouse IgG2a,__ | 309708 |
| Plate 3 | C09 | CD284 (TLR4) | HTA125 | Mouse IgG2a,__ | 312806 |
| Plate 3 | C10 | CD286 (TLR6) | TLR6.127 | Mouse IgG1,__ | 334708 |
| Plate 3 | C11 | CD290 | 3C10C5 | Mouse IgG1,__ | 354604 |
| Plate 3 | C12 | CD294 | BM16 | Rat IgG2a,__ | 350106 |
| Plate 3 | D01 | CD298 | LNH-94 | Mouse IgG1,__ | 341704 |
| Plate 3 | D02 | CD300e (IREM-2) | UP-H2 | Mouse IgG1,__ | 339704 |
| Plate 3 | D03 | CD300F | UP-D2 | Mouse IgG1,__ | 340604 |
| Plate 3 | D04 | CD301 | H037G3 | Mouse IgG2a,__ | 354704 |
| Plate 3 | D05 | CD303 | 201A | Mouse IgG2a,__ | 354204 |
| Plate 3 | D06 | CD304 | 12C2 | Mouse IgG2a,__ | 354504 |
| Plate 3 | D07 | CD307 | 509f6 | Mouse IgG2a,__ | 340304 |
| Plate 3 | D08 | CD307d (FcRL4) | 413D12 | Mouse IgG2b,__ | 340204 |
| Plate 3 | D09 | CD314 (NKG2D) | 1D11 | Mouse IgG1,__ | 320806 |
| Plate 3 | D10 | CD317 | RS38E | Mouse IgG1,__ | 348406 |
| Plate 3 | D11 | CD318 (CDCP1) | CUB1 | Mouse IgG2b,__ | 324006 |
| Plate 3 | D12 | CD319 (CRACC) | 162.1 | Mouse IgG2b,__ | 331806 |
| Plate 3 | E01 | CD324 (E-Cadherin) | 67A4 | Mouse IgG1,__ | 324106 |
| Plate 3 | E02 | CD325 | 8C11 | Mouse IgG1,__ | 350805 |
| Plate 3 | E03 | CD326 (Ep- CAM) | 9C4 | Mouse IgG2b,__ | 324206 |
| Plate 3 | E04 | CD328 (Siglec-7) | 6-434 | Mouse IgG1,__ | 339204 |
| Plate 3 | E05 | CD334 (FGFR4) | 4FR6D3 | Mouse IgG1,__ | 324306 |
| Plate 3 | E06 | CD335 (NKp46) | 9.00E+02 | Mouse IgG1,__ | 331908 |
| Plate 3 | E07 | CD336 (NKp44) | P44-8 | Mouse IgG1,__ | 325108 |
| Plate 3 | E08 | CD337 (NKp30) | P30-15 | Mouse IgG1,__ | 325208 |
| Plate 3 | E09 | CD338 (ABCG2) | 5D3 | Mouse IgG2b,__ | 332008 |
| Plate 3 | E10 | CD340 (erbB2/HER-2) | 24D2 | Mouse IgG1,__ | 324406 |
| Plate 3 | E11 | CD344 (Frizzled-4) | CH3A4A7 | Mouse IgG1,__ | 326606 |
| Plate 3 | E12 | CD351 | TX61 | Mouse IgG1,__ | 137306 |
| Plate 3 | F01 | CD352 (NTB-A) | NT-7 | Mouse IgG1,__ | 317208 |
| Plate 3 | F02 | CD354 (TREM-1) | TREM-26 | Mouse IgG1,__ | 314906 |
| Plate 3 | F03 | CD355 (CRTAM) | Cr24.1 | Mouse IgG2a,__ | 339106 |
| Plate 3 | F04 | CD357 (GITR) | 621 | Mouse IgG1,__ | 311604 |
| Plate 3 | F05 | CD360 (IL- 21R) | 2G1-K12 | Mouse IgG1,__ | 347806 |
| Plate 3 | F06 | __2- micro- globulin | 2M2 | Mouse IgG1,__ | 316306 |
| Plate 3 | F07 | BTLA | MIH26 | Mouse IgG2a,__ | 344506 |
| Plate 3 | F08 | C3AR | hC3aRZ8 | Mouse IgG2b | 345804 |

TABLE 2-continued

Antibodies included in the screen

| | | | | | |
|---|---|---|---|---|---|
| Plate 3 | F09 | C5L2 | 1D9-M12 | Mouse IgG2a,__ | 342404 |
| Plate 3 | F10 | CCR10 | May-88 | Arm. hamster IgG | 341504 |
| Plate 3 | F11 | CLEC12A | 50C1 | Mouse IgG2a,__ | 353604 |
| Plate 3 | F12 | CLEC9A | 8F9 | Mouse IgG2a,__ | 353804 |
| Plate 3 | G01 | CX3CR1 | 2A9-1 | Rat IgG2b,__ | 341604 |
| Plate 3 | G02 | CXCR7 | 8F11-M16 | Mouse IgG2b,__ | 331104 |
| Plate 3 | G03 | __-Opioid Receptor | DOR7D2A4 | Mouse IgG2b,__ | 327206 |
| Plate 3 | G04 | DLL1 | MHD1-314 | Mouse IgG1,__ | 346404 |
| Plate 3 | G05 | DLL4 | MHD4-46 | Mouse IgG1,__ | 346506 |
| Plate 3 | G06 | DR3 (TRAMP) | JD3 | Mouse IgG1,__ | 307106 |
| Plate 3 | G07 | EGFR | AY13 | Mouse IgG1,__ | 352904 |
| Plate 3 | G08 | erbB3/HER-3 | 1B4C3 | Mouse IgG2a,__ | 324706 |
| Plate 3 | G09 | Fc__Rl__ | AER-37 (CRA-1) | Mouse IgG2b,__ | 334610 |
| Plate 3 | G10 | FcRL6 | 2H3 | Mouse IgG2b,__ | Inquire |
| Plate 3 | G11 | Galectin-9 | 9M1-3 | Mouse IgG1,__ | 348906 |
| Plate 3 | G12 | GARP (LRRC32) | 7B11 | Mouse IgG2b,__ | 352504 |
| Plate 3 | H01 | HLA-A, B, C | W6/32 | Mouse IgG2a,__ | 311406 |
| Plate 3 | H02 | HLA-A2 | BB7.2 | Mouse IgG2b,__ | 343306 |
| Plate 3 | H03 | HLA-DQ | HLADQ1 | Mouse IgG1,__ | 318106 |
| Plate 3 | H04 | HLA-DR | L243 | Mouse IgG2a,__ | 307606 |
| Plate 3 | H05 | HLA-E | 3D12 | Mouse IgG1,__ | 342604 |
| Plate 3 | H06 | HLA-G | 87G | Mouse IgG2a,__ | 335906 |
| Plate 3 | H07 | IFN-g R b chain | 2HUB-159 | Hamster IgG | 308504 |
| Plate 3 | H08 | Ig light chain k | MHK-49 | Mouse IgG1,__ | 316508 |
| Plate 3 | H09 | Ig light chain__ | MHL-38 | Mouse IgG2a,__ | 316608 |
| Plate 3 | H10 | IgD | IA6-2 | Mouse IgG2a,__ | 348204 |
| Plate 3 | H11 | IgM | MHM-88 | Mouse IgG1,__ | 314508 |
| Plate 3 | H12 | IL-28RA | MHLICR2a | Mouse IgG2a,__ | 337804 |
| Plate 4 | A01 | Blank | | | |
| Plate 4 | A02 | Integrin α9β1 | Y9A2 | Mouse IgG1, κ | 351606 |
| Plate 4 | A03 | integrin β5 | AST-3T | Mouse IgG2a, κ | 345204 |
| Plate 4 | A04 | integrin β7 | FIB504 | Rat IgG2a, κ | 321204 |
| Plate 4 | A05 | Jagged 2 | MHJ2-523 | Mouse IgG1, κ | 346904 |
| Plate 4 | A06 | LAP | TW4-6H10 | Mouse IgG1, κ | 349704 |
| Plate 4 | A07 | Lymphotoxin b Receptor | 31G4D8 | Mouse IgG2b, κ | 322008 |
| Plate 4 | A08 | Mac-2 (Ga- lectin-3) | Gal397 | Mouse IgG1, κ | 126705 |
| Plate 4 | A09 | MAIR-II | TX45 | Mouse IgG1, κ | 334804 |
| Plate 4 | A10 | MICA/MICB | 6D4 | Mouse IgG2a, κ | 320906 |
| Plate 4 | A11 | MSC (W3D5) | W3D5 | Mouse IgG2a, κ | 327506 |
| Plate 4 | A12 | MSC (W5C5) | W5C5 | Mouse IgG1, κ | 327406 |
| Plate 4 | B01 | MSC (W7C6) | W7C6 | Mouse IgG1, κ | 327606 |
| Plate 4 | B02 | MSC and NPC (W4A5) | W4A5 | Mouse IgG1, κ | 330806 |
| Plate 4 | B03 | MSCA-1 (MSC, W8B2) | W8B2 | Mouse IgG1, κ | 327306 |
| Plate 4 | B04 | NKp80 | 5D12 | Mouse IgG1, κ | 346706 |
| Plate 4 | B05 | Notch 1 | MHN1-519 | Mouse IgG1, κ | 352106 |
| Plate 4 | B06 | Notch 2 | MHN2-25 | Mouse IgG2a, κ | 348304 |
| Plate 4 | B07 | Notch 3 | MHN3-21 | Mouse IgG1, κ | 345406 |
| Plate 4 | B08 | Notch 4 | MHN4-2 | Mouse IgG1, κ | 349004 |
| Plate 4 | B09 | NPC (57D2) | 57D2 | Mouse IgG1, κ | 327706 |
| Plate 4 | B10 | Podoplanin | NC-08 | Rat IgG2a, λ | 337004 |
| Plate 4 | B11 | Pre-BCR | HSL2 | Mouse IgG1, κ | 347904 |
| Plate 4 | B12 | PSMA | LNI-17 | Mouse IgG1, κ | 342504 |
| Plate 4 | C01 | Siglec-10 | 5G6 | Mouse IgG1, κ | 347604 |
| Plate 4 | C02 | Siglec-8 | 7C9 | Mouse IgG1, κ | 347104 |
| Plate 4 | C03 | Siglec-9 | K8 | Mouse IgG1, κ | 351504 |
| Plate 4 | C04 | SSEA-1 | MC-480 | Mouse IgM, κ | 125606 |
| Plate 4 | C05 | SSEA-3 | MC-631 | Rat IgM, κ | 330312 |
| Plate 4 | C06 | SSEA-4 | MC-813-70 | Mouse IgG3, κ | 330406 |
| Plate 4 | C07 | SSEA-5 | 8E+11 | Mouse IgG1, κ | 355204 |
| Plate 4 | C08 | TCR g/d | B1 | Mouse IgG1, κ | 331210 |
| Plate 4 | C09 | TCR Vβ13.2 | H132 | Mouse IgG1, κ | 333108 |
| Plate 4 | C10 | TCR Vβ23 | αHUT7 | Mouse IgG1, κ | 349406 |
| Plate 4 | C11 | TCR Vβ8 | JR2 (JR.2) | Mouse IgG2b, κ | 348104 |
| Plate 4 | C12 | TCR Vβ9 | MKB1 | Mouse IgG2b, κ | 349204 |
| Plate 4 | D01 | TCR Vδ2 | B6 | Mouse IgG1, κ | 331408 |
| Plate 4 | D02 | TCR Vg9 | B3 | Mouse IgG1, κ | 331308 |
| Plate 4 | D03 | TCR Vα24- Jα18 | 6B11 | Mouse IgG1, κ | 342904 |
| Plate 4 | D04 | TCR Vα7.2 | 3C10 | Mouse IgG1, κ | 351706 |
| Plate 4 | D05 | TCR α/β | IP26 | Mouse IgG1, κ | 306708 |
| Plate 4 | D06 | Tim-1 | 1D12 | Mouse IgG1, κ | 353904 |
| Plate 4 | D07 | Tim-3 | F38-2E2 | Mouse IgG1, κ | 345006 |
| Plate 4 | D08 | Tim-4 | 9F4 | Mouse IgG1, κ | 354004 |
| Plate 4 | D09 | TLT-2 | MIH61 | Mouse IgG1, κ | 351104 |
| Plate 4 | D10 | TRA-1-60-R | TRA-1-60-R | Mouse IgM, κ | 330610 |
| Plate 4 | D11 | TRA-1-81 | TRA-1-81 | Mouse IgM, κ | 330708 |
| Plate 4 | D12 | TSLPR (TSLP-R) | 1B4 | Mouse IgG1, κ | 322806 |
| Plate 4 | E01 | Ms IgG1, κ ITCL | MOPC-21 | Mouse IgG1, κ | 400112 |
| Plate 4 | E02 | Ms IgG2a, κ ITCL | MOPC-173 | Mouse IgG2a, κ | 400212 |

TABLE 2-continued

| Antibodies included in the screen | | | | | |
|---|---|---|---|---|---|
| Plate 4 | E03 | Ms IgG2b, κ ITCL | MPC-11 | Mouse IgG2b, κ | 400314 |
| Plate 4 | E04 | Ms IgG3, κ ITCL | MG3-35 | Mouse IgG3, κ | 401320 |
| Plate 4 | E05 | Ms IgM, κ ITCL | MM-30 | Mouse IgM, κ | 401609 |
| Plate 4 | E06 | Rat IgG1, κ ITCL | RTK2071 | Rat IgG1, κ | 400408 |
| Plate 4 | E07 | Rat IgG2a, κ ITCL | RTK2758 | Rat IgG2a, κ | 400508 |
| Plate 4 | E08 | Rat IgG2b, κ ITCL | RTK4530 | Rat IgG2b, κ | 400636 |
| Plate 4 | E09 | Rat IgM, κ ITCL | RTK2118 | Rat IgM, κ | 400808 |
| Plate 4 | E10 | AH IgG, ITCL | HTK888 | Arm. Hamster IgG | 400907 |
| Plate 4 | E11 | CD177 | MEM-166 | mouse IgG1, k | 315806 |
| Plate 4 | E12 | IL1RAP | 89412 | mouse IgG1, k | FAB676P |

Screen Iteration 70007

| Plate | WELL ID | Specificity | Clone | Isotype |
|---|---|---|---|---|
| Plate 1 | A01 | Blank | | |
| Plate 1 | A02 | IgG Isotype Ctrl | HTK888 | Arm. Hamster IgG |
| Plate 1 | A03 | CCR10 | 6588-5 | Arm. Hamster IgG |
| Plate 1 | A04 | CD278 | C398.4A | Arm. Hamster IgG |
| Plate 1 | A05 | IFN-γ R b chain | 2HUB-159 | Hamster IgG |
| Plate 1 | A06 | IgG1, κ Isotype Ctrl | MOPC-21 | Mouse IgG1, k |
| Plate 1 | A07 | CD46 | TRA-2-10 | Mouse IgG1 |
| Plate 1 | A08 | CD70 | 113-16 | Mouse IgG1 |
| Plate 1 | A09 | CD1a | HI149 | mouse IgG1, k |
| Plate 1 | A10 | CD2 | RPA-2.10 | mouse IgG1, k |
| Plate 1 | A11 | β2-microglobulin | 2M2 | mouse IgG1, k |
| Plate 1 | A12 | B7-H4 | MIH43 | mouse IgG1, k |
| Plate 1 | B01 | Cadherin 11 | 16G5 | mouse IgG1, k |
| Plate 1 | B02 | CD10 | HI10a | mouse IgG1, k |
| Plate 1 | B03 | CD100 | A8 | mouse IgG1, k |
| Plate 1 | B04 | CD103 | Ber-ACT8 | mouse IgG1, k |
| Plate 1 | B05 | CD105 (Endoglin) | SN6h | mouse IgG1, k |
| Plate 1 | B06 | CD106 | STA | mouse IgG1, k |
| Plate 1 | B07 | CD107a | H4A3 | mouse IgG1, k |
| Plate 1 | B08 | CD107b | H4B4 | mouse IgG1, k |
| Plate 1 | B09 | CD109 | W7C5 | mouse IgG1, k |
| Plate 1 | B10 | CD111 | R1.302 | mouse IgG1, k |
| Plate 1 | B11 | CD112 | TX31 | mouse IgG1, k |
| Plate 1 | B12 | CD114 | LMM741 | mouse IgG1, k |
| Plate 1 | C01 | CD116 | 4H1 | mouse IgG1, k |
| Plate 1 | C02 | CD117 | 104D2 | mouse IgG1, k |
| Plate 1 | C03 | CD119 | GIR-208 | mouse IgG1, k |
| Plate 1 | C04 | CD11a | HI111 | mouse IgG1, k |
| Plate 1 | C05 | CD11b | ICRF44 | mouse IgG1, k |
| Plate 1 | C06 | CD122 | TU27 | mouse IgG1, k |
| Plate 1 | C07 | CD123 | 6H6 | mouse IgG1, k |
| Plate 1 | C08 | CD126 | UV4 | mouse IgG1, k |
| Plate 1 | C09 | CD127 | A019D5 | mouse IgG1, k |
| Plate 1 | C10 | CD13 | WM15 | mouse IgG1, k |
| Plate 1 | C11 | CD131 | 1C1 | mouse IgG1, k |
| Plate 1 | C12 | CD134 | Ber-ACT35 (ACT35) | mouse IgG1, k |
| Plate 1 | D01 | CD135 | BV10A4H2 | mouse IgG1, k |
| Plate 1 | D02 | CD137 | 4B4-1 | mouse IgG1, k |
| Plate 1 | D03 | 4-1BB Ligand | 5F4 | mouse IgG1, k |
| Plate 1 | D04 | CD138 | MI15 | mouse IgG1, k |
| Plate 1 | D05 | CD14 | 63D3 | mouse IgG1, k |
| Plate 1 | D06 | CD140a | 16A1 | mouse IgG1, k |
| Plate 1 | D07 | CD140b | 18A2 | mouse IgG1, k |
| Plate 1 | D08 | CD141 | M80 | mouse IgG1, k |
| Plate 1 | D09 | CD142 | NY2 | mouse IgG1, k |
| Plate 1 | D10 | CD143 | 5-369 | mouse IgG1, k |
| Plate 1 | D11 | CD146 | P1H12 | mouse IgG1, k |
| Plate 1 | D12 | CD148 | A3 | mouse IgG1, k |
| Plate 1 | E01 | CD15 | W6D3 | mouse IgG1, k |
| Plate 1 | E02 | CD150 | A12 (7D4) | mouse IgG1, k |
| Plate 1 | E03 | CD151 | 50-6 | mouse IgG1, k |
| Plate 1 | E04 | CD154 | 24-31 | mouse IgG1, k |
| Plate 1 | E05 | CD156c | SHM14 | mouse IgG1, k |
| Plate 1 | E06 | CD158e1 | DX9 | mouse IgG1, k |
| Plate 1 | E07 | CD16 | 3G8 | mouse IgG1, k |
| Plate 1 | E08 | CD161 | HP-3G10 | mouse IgG1, k |
| Plate 1 | E09 | CD162 | KPL-1 | mouse IgG1, k |
| Plate 1 | E10 | CD163 | GHI/61 | mouse IgG1, k |
| Plate 1 | E11 | CD164 | 67D2 | mouse IgG1, k |
| Plate 1 | E12 | CD165 | SN2 (N6- D11) | mouse IgG1, k |
| Plate 1 | F01 | CD166 | 3A6 | mouse IgG1, k |
| Plate 1 | F02 | CD169 | 7-239 | mouse IgG1, k |
| Plate 1 | F03 | CD170 | 1A5 | mouse IgG1, k |

TABLE 2-continued

| Antibodies included in the screen | | | | |
|---|---|---|---|---|
| Plate 1 | F04 | CD172a/b (SIRPα/β) | SE5A5 | mouse IgG1, k |
| Plate 1 | F05 | CD172g (SIRPy) | LSB2.20 | mouse IgG1, k |
| Plate 1 | F06 | CD178 | NOK-1 | mouse IgG1, k |
| Plate 1 | F07 | CD179a | HSL96 | mouse IgG1, k |
| Plate 1 | F08 | CD179b | HSL11 | mouse IgG1, k |
| Plate 1 | F09 | CD18 | TS1/18 | mouse IgG1, k |
| Plate 1 | F10 | CD180 | MHR73-11 | mouse IgG1, k |
| Plate 1 | F11 | CD182 | 5E8/CXCR2 | mouse IgG1, k |
| Plate 1 | F12 | CD183 | G025H7 | mouse IgG1, k |
| Plate 1 | G01 | CD185 | J252D4 | mouse IgG1, k |
| Plate 1 | G02 | CD19 | HIB19 | mouse IgG1, k |
| Plate 1 | G03 | CD191 | 5F10B29 | mouse IgG1, k |
| Plate 1 | G04 | CD194 | L291H4 | mouse IgG1, k |
| Plate 1 | G05 | CD1b | SN13 (K5- 1B8) | mouse IgG1, k |
| Plate 1 | G06 | CD1c | L161 | mouse IgG1, k |
| Plate 1 | G07 | CD200 | OX-104 | mouse IgG1, k |
| Plate 1 | G08 | CD200R | OX-108 | mouse IgG1, k |
| Plate 1 | G09 | CD202b | 33.1 (Ab33) | mouse IgG1, k |
| Plate 1 | G10 | CD203c | NP4D6 | mouse IgG1, k |
| Plate 1 | G11 | CD205 | HD83 | mouse IgG1, k |
| Plate 1 | G12 | CD206 | 15-2 | mouse IgG1, k |
| Plate 1 | H01 | CD207 | 1E3 | mouse IgG1, k |
| Plate 1 | H02 | CD21 | Bu32 | mouse IgG1, k |
| Plate 1 | H03 | CD213a1 | SS12B | mouse IgG1, k |
| Plate 1 | H04 | CD213a2 | SHM38 | mouse IgG1, k |
| Plate 1 | H05 | CD218a | H44 | mouse IgG1, k |
| Plate 1 | H06 | CD221 | 1H7/CD221 | mouse IgG1, k |
| Plate 1 | H07 | CD223 (LAG-3) | 11C3C65 | mouse IgG1, k |
| Plate 1 | H08 | CD226 | 11A8 | mouse IgG1, k |
| Plate 1 | H09 | CD227 | 16A | mouse IgG1, k |
| Plate 1 | H10 | CD229 | HLy-9.1.25 | mouse IgG1, k |
| Plate 1 | H11 | CD23 | EBVCS-5 | mouse IgG1, k |
| Plate 1 | H12 | CD231 | SN1a (M3- 3D9) | mouse IgG1, k |
| Plate 2 | A01 | Blank | | |
| Plate 2 | A02 | CD244 (2B4) | C1.7 | mouse IgG1, k |
| Plate 2 | A03 | CD245 | DY12 | mouse IgG1, k |
| Plate 2 | A04 | CD25 | M-A251 | mouse IgG1, k |
| Plate 2 | A05 | CD252 | 11C3.1 | mouse IgG1, k |
| Plate 2 | A06 | CD261 | DJR1 | mouse IgG1, k |
| Plate 2 | A07 | CD262 | DJR2-4 (7-8) | mouse IgG1, k |
| Plate 2 | A08 | CD263 | DJR3 | mouse IgG1, k |
| Plate 2 | A09 | CD266 | ITEM-1 | mouse IgG1, k |
| Plate 2 | A10 | CD268 | 11C1 | mouse IgG1, k |
| Plate 2 | A11 | CD27 | M-T271 | mouse IgG1, k |
| Plate 2 | A12 | CD271 | ME20.4 | mouse IgG1, k |
| Plate 2 | B01 | CD275 | 9F.8A4 | mouse IgG1, k |
| Plate 2 | B02 | CD276 | MIH42 | mouse IgG1, k |
| Plate 2 | B03 | CD277 | BT3.1 | mouse IgG1, k |
| Plate 2 | B04 | CD279 | EH12.2H7 | mouse IgG1, k |
| Plate 2 | B05 | CD28 | CD28.2 | mouse IgG1, k |
| Plate 2 | B06 | CD29 | TS2/16 | mouse IgG1, k |
| Plate 2 | B07 | CD290 | 3C10C5 | mouse IgG1, k |
| Plate 2 | B08 | CD298 | LNH-94 | mouse IgG1, k |
| Plate 2 | B09 | CD3 | UCHT1 | mouse IgG1, k |
| Plate 2 | B10 | CD30 | BY88 | mouse IgG1, k |
| Plate 2 | B11 | CD300c | TX45 | mouse IgG1, k |
| Plate 2 | B12 | CD309 | 7D4-6 | mouse IgG1, k |
| Plate 2 | C01 | CD31 | WM59 | mouse IgG1, k |
| Plate 2 | C02 | CD314 | 1D11 | mouse IgG1, k |
| Plate 2 | C03 | CD317 | RS38E | mouse IgG1, k |
| Plate 2 | C04 | CD324 | 67A4 | mouse IgG1, k |
| Plate 2 | C05 | CD325 | 8C11 | mouse IgG1, k |
| Plate 2 | C06 | CD328 | 6-434 | mouse IgG1, k |
| Plate 2 | C07 | CD33 | WM53 | mouse IgG1, k |
| Plate 2 | C08 | CD334 | 4FR6D3 | mouse IgG1, k |
| Plate 2 | C09 | CD335 | 9E2 | mouse IgG1, k |
| Plate 2 | C10 | CD336 | P44-8 | mouse IgG1, k |
| Plate 2 | C11 | CD337 | P30-15 | mouse IgG1, k |
| Plate 2 | C12 | CD34 | 581 | mouse IgG1, k |
| Plate 2 | D01 | CD340 | 24D2 | mouse IgG1, k |
| Plate 2 | D02 | CD344 | CH3A4A7 | mouse IgG1, k |
| Plate 2 | D03 | CD35 | E11 | mouse IgG1, k |
| Plate 2 | D04 | CD354 | TREM-26 | mouse IgG1, k |
| Plate 2 | D05 | CD360 | 17A12 | mouse IgG1, k |
| Plate 2 | D06 | CD365 | 1D12 | mouse IgG1, k |
| Plate 2 | D07 | CD366 | F38-2E2 | mouse IgG1, k |
| Plate 2 | D08 | CLEC4A | 9E8 | mouse IgG1, k |
| Plate 2 | D09 | CD36L1 | m1b9 | mouse IgG1, k |

TABLE 2-continued

| Antibodies included in the screen | | | | |
|---|---|---|---|---|
| Plate 2 | D10 | CD38 | HIT2 | mouse IgG1, k |
| Plate 2 | D11 | CD39 | A1 | mouse IgG1, k |
| Plate 2 | D12 | CD4 | RPA-T4 | mouse IgG1, k |
| Plate 2 | E01 | CD40 | 5C3 | mouse IgG1, k |
| Plate 2 | E02 | CD41 | HIP8 | mouse IgG1, k |
| Plate 2 | E03 | CD42b | HIP1 | mouse IgG1, k |
| Plate 2 | E04 | CD43 | CD43-10G7 | mouse IgG1, k |
| Plate 2 | E05 | CD44 | BJ18 | mouse IgG1, k |
| Plate 2 | E06 | CD45 | HI30 | mouse IgG1, k |
| Plate 2 | E07 | CD47 | CC2C6 | mouse IgG1, k |
| Plate 2 | E08 | CD48 | BJ40 | mouse IgG1, k |
| Plate 2 | E09 | CD49a | TS2/7 | mouse IgG1, k |
| Plate 2 | E10 | CD49b | P1E6-C5 | mouse IgG1, k |
| Plate 2 | E11 | CD49c | ASC-1 | mouse IgG1, k |
| Plate 2 | E12 | CD49d | 9F10 | mouse IgG1, k |
| Plate 2 | F01 | CD5 | UCHT2 | mouse IgG1, k |
| Plate 2 | F02 | CD50 | CBR-IC3/1 | mouse IgG1, k |
| Plate 2 | F03 | CD54 | HA58 | mouse IgG1, k |
| Plate 2 | F04 | CD55 | JS11 | mouse IgG1, k |
| Plate 2 | F05 | CD56 (NCAM) | 5.1H11 | mouse IgG1, k |
| Plate 2 | F06 | CD58 | TS2/9 | mouse IgG1, k |
| Plate 2 | F07 | CD6 | BL-CD6 | mouse IgG1, k |
| Plate 2 | F08 | CD61 | VI-PL2 | mouse IgG1, k |
| Plate 2 | F09 | CD62E | HAE-1f | mouse IgG1, k |
| Plate 2 | F10 | CD62L | DREG-56 | mouse IgG1, k |
| Plate 2 | F11 | CD62P | AK4 | mouse IgG1, k |
| Plate 2 | F12 | CD63 | H5C6 | mouse IgG1, k |
| Plate 2 | G01 | CD64 | 10.1 | mouse IgG1, k |
| Plate 2 | G02 | CD69 | FN50 | mouse IgG1, k |
| Plate 2 | G03 | CD73 | AD2 | mouse IgG1, k |
| Plate 2 | G04 | CD74 | LN2 | mouse IgG1, k |
| Plate 2 | G05 | CD79b | CB3-1 | mouse IgG1, k |
| Plate 2 | G06 | CD8a | SK1 | mouse IgG1, k |
| Plate 2 | G07 | CD80 | 2D10 | mouse IgG1, k |
| Plate 2 | G08 | CD81 | 5A6 | mouse IgG1, k |
| Plate 2 | G09 | CD82 | ASL-24 | mouse IgG1, k |
| Plate 2 | G10 | CD83 | HB15e | mouse IgG1, k |
| Plate 2 | G11 | CD85 | 17G10.2 | mouse IgG1, k |
| Plate 2 | G12 | CD85k | ZM4.1 | mouse IgG1, k |
| Plate 2 | H01 | CD87 | VIM5 | mouse IgG1, k |
| Plate 2 | H02 | CD89 | A59 | mouse IgG1, k |
| Plate 2 | H03 | CD8a | RPA-T8 | mouse IgG1, k |
| Plate 2 | H04 | CD9 | HI9a | mouse IgG1, k |
| Plate 2 | H05 | CD90 | 5E10 | mouse IgG1, k |
| Plate 2 | H06 | CD93 | VIMD2 | mouse IgG1, k |
| Plate 2 | H07 | CD94 | DX22 | mouse IgG1, k |
| Plate 2 | H08 | CD95 | DX2 | mouse IgG1, k |
| Plate 2 | H09 | CD96 | NK92.39 | mouse IgG1, k |
| Plate 2 | H10 | CD97 | VIM3b | mouse IgG1, k |
| Plate 2 | H11 | CD99 | 3B2/TA8 | mouse IgG1, k |
| Plate 2 | H12 | CXCL16 | 22-19-12 | mouse IgG1, k |
| Plate 3 | A01 | Blank | | |
| Plate 3 | A02 | DLL1 | MHD1-314 | mouse IgG1, k |
| Plate 3 | A03 | DLL4 | MHD4-46 | mouse IgG1, k |
| Plate 3 | A04 | DR3 | JD3 | mouse IgG1, k |
| Plate 3 | A05 | EGFR | AY13 | mouse IgG1, k |
| Plate 3 | A06 | CD357 | 108-17 | mouse IgG1, k |
| Plate 3 | A07 | GPR19 | K152D10 | mouse IgG1, k |
| Plate 3 | A08 | GPR56 | CG4 | mouse IgG1, k |
| Plate 3 | A09 | HLA-E | 3D12 | mouse IgG1, k |
| Plate 3 | A10 | HVEM | 122 | mouse IgG1, k |
| Plate 3 | A11 | Ig light chain κ | MHK-49 | mouse IgG1, k |
| Plate 3 | A12 | IgM | MHM-88 | mouse IgG1, k |
| Plate 3 | B01 | CD360 | 2G1-K12 | mouse IgG1, k |
| Plate 3 | B02 | Integrin α9β1 | Y9A2 | mouse IgG1, k |
| Plate 3 | B03 | Jagged 2 | MHJ2-523 | mouse IgG1, k |
| Plate 3 | B04 | Ksp37 | TDA3 | mouse IgG1, k |
| Plate 3 | B05 | LAP | TW4-2F8 | mouse IgG1, k |
| Plate 3 | B06 | LY6G6D | 13.8 | mouse IgG1, k |
| Plate 3 | B07 | MERTK | 590H11G1E3 | mouse IgG1, k |
| Plate 3 | B08 | MSC | W7C6 | mouse IgG1, k |
| Plate 3 | B09 | MSC, NPC | W4A5 | mouse IgG1, k |
| Plate 3 | B10 | TNAP | W8B2 | mouse IgG1, k |
| Plate 3 | B11 | MUC-13 | TCC16 | mouse IgG1, k |
| Plate 3 | B12 | NKp80 | 5D12 | mouse IgG1, k |
| Plate 3 | C01 | Notch 1 | MHN1-519 | mouse IgG1, k |
| Plate 3 | C02 | Notch3 | MHN3-21 | mouse IgG1, k |
| Plate 3 | C03 | Notch 4 | MHN4-2 | mouse IgG1, k |

TABLE 2-continued

| Antibodies included in the screen | | | | |
|---|---|---|---|---|
| Plate 3 | C04 | NPC | 57D2 | mouse IgG1, k |
| Plate 3 | C05 | CD352 | NT-7 | mouse IgG1, k |
| Plate 3 | C06 | PSMA | LNI-17 | mouse IgG1, k |
| Plate 3 | C07 | ROR1 | 2A2 | mouse IgG1, k |
| Plate 3 | C08 | Siglec-10 | 5G6 | mouse IgG1, k |
| Plate 3 | C09 | CD328 | S7.7 | mouse IgG1, k |
| Plate 3 | C10 | Siglec-8 | 7C9 | mouse IgG1, k |
| Plate 3 | C11 | Siglec-9 | K8 | mouse IgG1, k |
| Plate 3 | C12 | SSEA-5 | 8E11 | mouse IgG1, k |
| Plate 3 | D01 | SUSD2 | W5C5 | mouse IgG1, k |
| Plate 3 | D02 | TCR α/β | IP26 | mouse IgG1, k |
| Plate 3 | D03 | TCR γ/δ | B1 | mouse IgG1, k |
| Plate 3 | D04 | Tim-4 | 9F4 | mouse IgG1, k |
| Plate 3 | D05 | TLT-2 | MIH61 | mouse IgG1, k |
| Plate 3 | D06 | TM4SF20 | C9 | mouse IgG1, k |
| Plate 3 | D07 | TRA-2-49 | TRA-2- 49/6E | mouse IgG1, k |
| Plate 3 | D08 | TRA-2-54 | TRA-2-54/2J | mouse IgG1, k |
| Plate 3 | D09 | TSLPR | 1B4 | mouse IgG1, k |
| Plate 3 | D10 | VEGFR-3 | 9D9F9 | mouse IgG1, k |
| Plate 3 | D11 | IgG2a, κ Isotype Ctrl | MOPC-173 | mouse IgG2a, k |
| Plate 3 | D12 | APCDD1 | 7.13 | mouse IgG2a, k |
| Plate 3 | E01 | CD272 | MIH26 | mouse IgG2a, k |
| Plate 3 | E02 | CD198 | L263G8 | mouse IgG2a, k |
| Plate 3 | E03 | CCRL2 | K097F7 | mouse IgG2a, k |
| Plate 3 | E04 | CD102 | CBR-IC2/2 | mouse IgG2a, k |
| Plate 3 | E05 | CD104 | 58XB4 | mouse IgG2a, k |
| Plate 3 | E06 | CD124 | G077F6 | mouse IgG2a, k |
| Plate 3 | E07 | CD130 | 2E1B02 | mouse IgG2a, k |
| Plate 3 | E08 | CD144 | BV9 | mouse IgG2a, k |
| Plate 3 | E09 | CD152 (CTLA-4) | BNI3 | mouse IgG2a, k |
| Plate 3 | E10 | CD155 | TX24 | mouse IgG2a, k |
| Plate 3 | E11 | CD158b | DX27 | mouse IgG2a, k |
| Plate 3 | E12 | CD184 | 12G5 | mouse IgG2a, k |
| Plate 3 | F01 | CD186 | K041E5 | mouse IgG2a, k |
| Plate 3 | F02 | CD192 | K036C2 | mouse IgG2a, k |
| Plate 3 | F03 | CD197 | G043H7 | mouse IgG2a, k |
| Plate 3 | F04 | CD199 | L053E8 | mouse IgG2a, k |
| Plate 3 | F05 | CD209 | 9E9A8 | mouse IgG2a, k |
| Plate 3 | F06 | CD217 | W15177A | mouse IgG2a, k |
| Plate 3 | F07 | CD230 (Prion) | 3F4 | mouse IgG2a, k |
| Plate 3 | F08 | CD24 | ML5 | mouse IgG2a, k |
| Plate 3 | F09 | CD243 | UIC2 | mouse IgG2a, k |
| Plate 3 | F10 | CD26 | BA5b | mouse IgG2a, k |
| Plate 3 | F11 | CD269 | 19F2 | mouse IgG2a, k |
| Plate 3 | F12 | CD282 | TL2.1 | mouse IgG2a, k |
| Plate 3 | G01 | CD284 | HTA125 | mouse IgG2a, k |
| Plate 3 | G02 | CD301 | H037G3 | mouse IgG2a, k |
| Plate 3 | G03 | CD303 | 201A | mouse IgG2a, k |
| Plate 3 | G04 | CD304 | 12C2 | mouse IgG2a, k |
| Plate 3 | G05 | CD307e | 509f6 | mouse IgG2a, k |
| Plate 3 | G06 | CD323 | SHM33 | mouse IgG2a, k |
| Plate 3 | G07 | CD357 | 108-17 | mouse IgG2a, k |
| Plate 3 | G08 | CD36 | 5-271 | mouse IgG2a, k |
| Plate 3 | G09 | CD369 | 15E2 | mouse IgG2a, k |
| Plate 3 | G10 | CD370 | 8F9 | mouse IgG2a, k |
| Plate 3 | G11 | CD371 | 50C1 | mouse IgG2a, k |
| Plate 3 | G12 | CD45RO | UCHL1 | mouse IgG2a, k |
| Plate 3 | H01 | CD51 | NKI-M9 | mouse IgG2a, k |
| Plate 3 | H02 | CD59 | p282 (H19) | mouse IgG2a, k |
| Plate 3 | H03 | CD7 | CD7-6B7 | mouse IgG2a, k |
| Plate 3 | H04 | CD71 | CY1G4 | mouse IgG2a, k |
| Plate 3 | H05 | CD84 | CD84.1.21 | mouse IgG2a, k |
| Plate 3 | H06 | CD88 | S5/1 | mouse IgG2a, k |
| Plate 3 | H07 | CD355 | Cr24.1 | mouse IgG2a, k |
| Plate 3 | H08 | erbB3 | 1B4C3 | mouse IgG2a, k |
| Plate 3 | H09 | FPR3 | K102B9 | mouse IgG2a, k |
| Plate 3 | H10 | Ganglioside GD2 | 14G2a | mouse IgG2a, k |
| Plate 3 | H11 | GPR83 | K07JP05 | mouse IgG2a, k |
| Plate 3 | H12 | HLA-A, B, C | W6/32 | mouse IgG2a, k |
| Plate 4 | A01 | Blank | | |
| Plate 4 | A02 | HLA-DR | L243 | mouse IgG2a, k |
| Plate 4 | A03 | Ig light chain λ | MHL-38 | mouse IgG2a, k |
| Plate 4 | A04 | IgD | IA6-2 | mouse IgG2a, k |
| Plate 4 | A05 | IL-28RA | MHLICR2a | mouse IgG2a, k |
| Plate 4 | A06 | integrin β5 | AST-3T | mouse IgG2a, k |
| Plate 4 | A07 | KLRG1 | SA231A2 | mouse IgG2a, k |
| Plate 4 | A08 | LOX-1 | 15C4 | mouse IgG2a, k |
| Plate 4 | A09 | MICA/MICB | 6D4 | mouse IgG2a, k |

TABLE 2-continued

| Antibodies included in the screen | | | | |
|---|---|---|---|---|
| Plate 4 | A10 | SUSD2 | W3D5 | mouse IgG2a, k |
| Plate 4 | A11 | Notch 2 | MHN2-25 | mouse IgG2a, k |
| Plate 4 | A12 | TACSTD2 | NY18 | mouse IgG2a, k |
| Plate 4 | B01 | TIGIT (VSTM3) | A15153G | mouse IgG2a, k |
| Plate 4 | B02 | IgG2b, κ Isotype Ctrl | MPC-11 | mouse IgG2b, k |
| Plate 4 | B03 | C3aR | hC3aRZ8 | mouse IgG2b, k |
| Plate 4 | B04 | CCX-CKR (CCRL1) | 13E11 | mouse IgG2b, k |
| Plate 4 | B05 | CD110 | S-HCL-3 | mouse IgG2b, k |
| Plate 4 | B06 | CD129 | AH9R7 | mouse IgG2b, k |
| Plate 4 | B07 | CD158 | HP-MA4 | mouse IgG2b, k |
| Plate 4 | B08 | CD181 | 8F1/CXCR1 | mouse IgG2b, k |
| Plate 4 | B09 | CD193 | 5E8 | mouse IgG2b, k |
| Plate 4 | B10 | CD196 | G034E3 | mouse IgG2b, k |
| Plate 4 | B11 | CD1d | 51.1 | mouse IgG2b, k |
| Plate 4 | B12 | CD20 | 2H7 | mouse IgG2b, k |
| Plate 4 | C01 | CD22 | S-HCL-1 | mouse IgG2b, k |
| Plate 4 | C02 | CD220 | B6.220 | mouse IgG2b, k |
| Plate 4 | C03 | CD235ab | HIR2 | mouse IgG2b, k |
| Plate 4 | C04 | CD258 | T5-39 | mouse IgG2b, k |
| Plate 4 | C05 | CD274 | 29E.2A3 | mouse IgG2b, k |
| Plate 4 | C06 | CD319 | 162.1 | mouse IgG2b, k |
| Plate 4 | C07 | CD32 | FUN-2 | mouse IgG2b, k |
| Plate 4 | C08 | CD326 | 9C4 | mouse IgG2b, k |
| Plate 4 | C09 | CD338 | 5D3 | mouse IgG2b, k |
| Plate 4 | C10 | CD368 | 9B9 | mouse IgG2b, k |
| Plate 4 | C11 | CD45RA | HI100 | mouse IgG2b, k |
| Plate 4 | C12 | CD45RB | MEM-55 | mouse IgG2b, k |
| Plate 4 | D01 | CD49e | NKI-SAM-1 | mouse IgG2b, k |
| Plate 4 | D02 | CD52 | HI186 | mouse IgG2b, k |
| Plate 4 | D03 | CD66a/c/e | ASL-32 | mouse IgG2b, k |
| Plate 4 | D04 | CD85h | 24 | mouse IgG2b, k |
| Plate 4 | D05 | CD85 | GHI/75 | mouse IgG2b, k |
| Plate 4 | D06 | CD86 | IT2.2 | mouse IgG2b, k |
| Plate 4 | D07 | CD92 | VIM15b | mouse IgG2b, k |
| Plate 4 | D08 | CXCR7 | 8F11-M16 | mouse IgG2b, k |
| Plate 4 | D09 | Delta Opioid Receptor | DOR7D2A4 | mouse IgG2b, k |
| Plate 4 | D10 | Dopamine Receptor D1 | L205G1 | mouse IgG2b, k |
| Plate 4 | D11 | EphA2 | SHM16 | mouse IgG2b, k |
| Plate 4 | D12 | FcεRIα | AER-37 (CRA-1) | mouse IgG2b, k |
| Plate 4 | E01 | GARP | 7B11 | mouse IgG2b, k |
| Plate 4 | E02 | CD215 | JM7A4 | mouse IgG2b, k |
| Plate 4 | E03 | Lymphotoxin β Receptor | 31G4D8 | mouse IgG2b, k |
| Plate 4 | E04 | MRGX2 | K125H4 | mouse IgG2b, k |
| Plate 4 | E05 | TMEM8A | SA065C3 | mouse IgG2b, k |
| Plate 4 | E06 | CD254 | MIH24 | mouse IgG2b, k |
| Plate 4 | E07 | CD318 | CUB1 | mouse IgG2b, k |
| Plate 4 | E08 | IgG3, k Isotype Ctrl | MG3-35 | mouse IgG3, k |
| Plate 4 | E09 | CD255 | CARL-1 | Mouse IgG3, k |
| Plate 4 | E10 | SSEA-4 | MC-813-70 | Mouse IgG3, k |
| Plate 4 | E11 | IgM, κ Isotype Ctrl | MM-30 | Mouse IgM, k |
| Plate 4 | E12 | Sialyl Lewis X (dimeric) | FH6 | Mouse IgM, k |
| Plate 4 | F01 | TRA-1-81 | TRA-1-81 | Mouse IgM, k |
| Plate 4 | F02 | CD160 | BY55 | Mouse IgM, k |
| Plate 4 | F03 | CD57 | HNK-1 | Mouse IgM, k |
| Plate 4 | F04 | CD66b | G10F5 | Mouse IgM, k |
| Plate 4 | F05 | TRA-1-60-R | TRA-1-60-R | Mouse IgM, k |
| Plate 4 | F06 | IgG1, κ Isotype Ctrl | RTK2071 | Rat IgG1, k |
| Plate 4 | F07 | CD115 | 9-4D2-1E4 | Rat IgG1, k |
| Plate 4 | F08 | CD201 | RCR-401 | Rat IgG1, k |
| Plate 4 | F09 | IgG2a, κ Isotype Ctrl | RTK2758 | Rat IgG2a, k |
| Plate 4 | F10 | CD120b | 3G7A02 | Rat IgG2a, k |
| Plate 4 | F11 | CD210 | 3F9 | Rat IgG2a, k |
| Plate 4 | F12 | CD267 | 1A1 | Rat IgG2a, k |
| Plate 4 | G01 | CD294 | BM16 | Rat IgG2a, k |
| Plate 4 | G02 | CD49f | GoH3 | Rat IgG2a, k |
| Plate 4 | G03 | CD85 | MKT5.1 | Rat IgG2a, k |
| Plate 4 | G04 | CD85d | 42D1 | Rat IgG2a, k |
| Plate 4 | G05 | IgG Fc | M1310G05 | Rat IgG2a, k |
| Plate 4 | G06 | Integrin β7 | FIB504 | Rat IgG2a, k |
| Plate 4 | G07 | XCR1 | S15046E | Rat IgG2a, k |
| Plate 4 | G08 | Podoplanin | NC-08 | Rat IgG2a, l |
| Plate 4 | G09 | IgG2b, κ Isotype Ctrl | RTK4530 | Rat IgG2b, k |
| Plate 4 | G10 | CD132 | TUGh4 | Rat IgG2b, k |
| Plate 4 | G11 | CD195 | J418F1 | Rat IgG2b, k |
| Plate 4 | G12 | CX3CR1 | 2A9-1 | Rat IgG2b, k |

TABLE 2-continued

| Antibodies included in the screen | | | | |
|---|---|---|---|---|
| Plate 4 | H01 | IgM, κ Isotype Ctrl | RTK2118 | Rat IgM, k |
| Plate 4 | H02 | SSEA-3 | MC-631 | Rat IgM, k |
| Plate 4 | H03 | CD177 | MEM-166 | mouse IgG1, k |
| Plate 4 | H04 | IL1RAP | 89412 | mouse IgG1, k |

TABLE 3

Antibodies and Reagents

| Name of Product | Target | Fluorochrome | Company | Isotype | Catalog # |
|---|---|---|---|---|---|
| LEGENDScreen[a] Human PE Kit | SCREEN | PE | BioLegend | 10 different | 700001 |
| LEGENDScreen[a] Human PE Kit | SCREEN | PE | BioLegend | 10 different | 700007 |
| PE/Cy7 anti-human CD3 Antibody | CD3 | PE-Cy7 | BioLegend | mouse IgG2a, k | 300316 |
| APC/Cy7 anti-human CD19 Antibody | CD19 | APC-Cy7 | BioLegend | mouse IgG1, k | 302218 |
| Alexa Fluor¨ 488 anti-human CD34 Antibody | CD34 | AF488 | BioLegend | mouse IgG1, k | 343518 |
| APC/Cy7 anti-human CD34 Antibody | CD34 | APC-Cy7 | BioLegend | mouse IgG2a, k | 343614 |
| BV421 Mouse Anti-Human CD34 | CD34 | BV421 | BD | mouse IgG1, k | 562577 |
| BV711 Mouse Anti-Human CD38 Clone HIT2 (RUO) | CD38 | BV711 | BD | mouse IgG1, k | 563965 |
| PE-Cy7 Mouse Anti-Human CD45RA | CD45RA | PE-Cy7 | BD | mouse IgG2b, k | 560675 |
| Alexa Fluor 488 anti-human CD123 Antibody | CD123 | AF488 | BioLegend | mouse IgG1, k | 306036 |
| PerCP/Cyanine5.5 anti-human CD90 (Thy1) Antibody | CD90 | PerCP-Cy5.5 | BioLegend | mouse IgG1, k | 328117 |
| APC anti-human CD45 Antibody | CD45 | APC | BioLegend | mouse IgG1, k | 982304 |
| PE anti-human CD177 Antibody | CD177 | PE | BioLegend | mouse IgG1, k | 315806 |
| Human IL-1 RAcP/IL-1 R3 PE-conjugated Antibody | IL1RAP | PE | RnD Systems | mouse IgG1, k | FAB676P |
| PE anti-human CD62E Antibody | CD62E | PE | BioLegend | mouse IgG1, k | 336008 |
| PE anti-human CD54 Antibody | CD54 | PE | BioLegend | mouse IgG1, k | 353105 |
| PE anti-human CD244 (2B4) Antibody | CD244 | PE | BioLegend | mouse IgG1, k | 393507 |
| PE anti-human Jagged 2 Antibody | Jagged 2 | PE | BioLegend | mouse IgG1, k | 346904 |
| PE anti-human CD323 (JAM3) Antibody | CD323 | PE | BioLegend | mouse IgG2a, k | 356703 |
| PE anti-CD105 (Endoglin) Antibody | CD105 | PE | BioLegend | mouse IgG1, k | 800503 |
| PE anti-human CD369 (Dectin-1/CLEC7A) Antibody | CD369 | PE | BioLegend | mouse IgG2a, k | 355403 |
| PE anti-human CD352 (NTB-A) Antibody | SLAMF6 | PE | BioLegend | mouse IgG1, k | 317207 |
| Anti-SLAMF6 antibody [EPR22170] | SLAMF6 | — | Abcam | mono IgG rabbit | ab238421 |
| PE Mouse IgG1, κ Isotype Ctrl Antibody | ISO | PE | BioLegend | mouse IgG1, k | 400112 |
| PE Mouse IgG2a, κ Isotype Ctrl (FC) Antibody | ISO | PE | BioLegend | mouse IgG2a | 400214 |
| Rabbit IgG, monoclonal [EPR25A] | ISO | — | Abcam | mono IgG rabbit | ab199376 |
| 7-AAD Viability Staining Solution | 7AAD | — | BioLegend | — | 420404 |
| 4',6-Diamidine-2'-phenylindole dihydrochloride | DAPI | — | Sigma-Aldrich | — | D9542 |

TABLE 4

Top Cell Surface Marker Candidates

| Rank | Specificity | Gene Symbol | NBM#1 MFI | NBM#2 MFI | NBM#3 MFI | AML#48 MFI | AML#83 MFI | AML#80 MFI | Rank AML − NBM | Rank AML/NBM | Mean Rank |
|---|---|---|---|---|---|---|---|---|---|---|---|
| 1 | CD123 | IL3RA | 86.7 | 1000 | 1059 | 2893 | 4057 | 1121 | 3 | 12 | 7.5 |
| 2 | CD369 | CLEC7A | | 1106 | 88.7 | | 2650 | 1920 | 15 | 1 | 8 |
| 3 | CD352 | SLAMF6, NTB-A | 153 | 689 | 627 | 1754 | 1495 | 3253 | 14 | 6 | 10 |
| 4 | CD54 | ICAM1 | −427 | 1302 | 1134 | 633 | 4308 | 8953 | 2 | 18 | 10 |
| 5 | CD105 | ENG | 320 | 1764 | 1154 | 1199 | 3678 | 6067 | 6 | 14 | 10 |
| 6 | CD370 | CLEC9A | 33.3 | 653 | 1197 | 241 | 2025 | 4185 | 18 | 4 | 11 |
| 7 | CD323 | JAM3 | | 1384 | 1067 | | 3292 | 3345 | 7 | 24 | 15.5 |
| 8 | CD93 | CD93 | 140 | 1381 | 1906 | 1890 | 1784 | 5837 | 9 | 22 | 15.5 |
| 9 | CD11c | ITGAX | −1528 | 988 | 550 | −249 | 1206 | 3379 | 19 | 15 | 17 |
| 10 | TRA-2-54 | ALPL | | 692 | 465 | | 4091 | 1686 | 26 | 8 | 17 |
| 11 | IL1RAP | IL1RAP | −53.3 | 564 | 305 | 440 | 1818 | 1655 | 22 | 20 | 21 |
| 12 | CD252 | TNFSF4 | −300 | | 194 | 42.7 | 4159 | 1931 | 35 | 7 | 21 |
| 13 | CD261 | TNFRSF10A | −414 | 1130 | 434 | −849 | 2609 | 2359 | 16 | 33 | 24.5 |
| 14 | CD56 | NCAM1 | −80 | 587 | 302 | 19.4 | 3138 | 1165 | 49 | 13 | 31 |
| 15 | CD49d | ITGA4 | 1295 | 2558 | 3163 | 2574 | 2495 | 7646 | 20 | 43 | 31.5 |
| 16 | TLT-2 | TRML2 | −883 | 646 | 420 | 7.77 | 1621 | 1567 | 44 | 21 | 32.5 |
| 17 | CD11b | ITGAM | −541 | 758 | 358 | 34.9 | 1784 | 1931 | 36 | 31 | 33.5 |
| 18 | CD314 | KLRK1 | −501 | 1251 | 2231 | −793 | 2911 | 4049 | 13 | 55 | 34 |
| 19 | CD49c | ITGA3 | −681 | 1244 | 1774 | −2513 | 2442 | 3525 | 30 | 44 | 37 |
| 20 | CD266 | TNFRSF12A | −1309 | 641 | 64.2 | 73.8 | 694 | 602 | 77 | 5 | 41 |
| 21 | CD165 | ADAMTSL1 | 60 | 1448 | 1902 | 303 | 4281 | 2578 | 62 | 23 | 42.5 |
| 22 | CD344 | FZD4 | −675 | 2283 | 1392 | −745 | 3040 | 4116 | 56 | 41 | 48.5 |
| 23 | Jagged 2 | JAG2 | −7099 | 2676 | 1561 | 637 | 4057 | 3785 | 5 | 93 | 49 |
| 24 | CD7 | CD7 | −387 | 661 | 676 | 6668 | 1667 | 1183 | 41 | 58 | 49.5 |
| 25 | CD156c | ADAM10 | 856 | 3189 | 4176 | 3403 | 4903 | 4352 | 12 | 88 | 50 |
| 26 | CD354 | TREM1 | 40 | 1280 | 567 | 562 | 1392 | 2168 | 81 | 27 | 54 |
| 27 | CD94 | KLRD1 | −2968 | 383 | 516 | −42.7 | 851 | 1136 | 71 | 38 | 54.5 |
| 28 | CD263 | TNFRSF10C | −340 | 1523 | 903 | −233 | 2505 | 2262 | 43 | 69 | 56 |
| 29 | CD124 | IL4R | 127 | 1310 | 1152 | 507 | 3145 | 1658 | 83 | 29 | 56 |
| 30 | CD1d | CD1D | −795 | 1327 | 136 | −813 | 2231 | 2609 | 47 | 67 | 57 |
| 31 | CD144 | CDH5 | 133 | 1106 | 1138 | −350 | 1892 | 3641 | 54 | 60 | 57 |
| 32 | Siglec-8 | SIGLEC8 | −2353 | 1478 | 59.1 | −315 | 2099 | 1788 | 10 | 105 | 57.5 |
| 33 | PSMA | FOLH1 | −133 | 817 | 705 | 50.5 | 1532 | 1376 | 65 | 53 | 59 |
| 34 | CD134 | TNFSRF4 | 40 | 982 | 943 | 284 | 1529 | 1856 | 74 | 45 | 59.5 |
| 35 | CD258 | TNFSRF14 | −73.3 | 1874 | 53.9 | −483 | 2177 | 1518 | 119 | 3 | 61 |
| 36 | TCR α/β | TRAC | −3013 | 1227 | 939 | 159 | 1670 | 1798 | 51 | 72 | 61.5 |
| 37 | CD275 | ICOSLG | 80 | 1278 | 722 | 491 | 1822 | 1735 | 76 | 48 | 62 |
| 38 | CD182 | CXCR2 | 180 | 483 | 438 | 745 | 1002 | −594 | 82 | 42 | 62 |
| 39 | SSEA-5 | | −1099 | 1418 | 152 | 117 | 2095 | 2414 | 27 | 99 | 63 |
| 40 | CD45RB | PTPRC | 153 | 395 | 151 | 503 | 1957 | 500 | 109 | 17 | 63 |
| 41 | Siglec-10 | SIGLEC10 | −748 | 1424 | 1290 | −257 | 2266 | 3234 | 52 | 79 | 65.5 |
| 42 | MICA/MICB | MICA/MICB | −534 | 1076 | 504 | −3.88 | 1199 | 1337 | 79 | 52 | 65.5 |
| 43 | IgD | IGHD | −2154 | 978 | 661 | −11.6 | 1358 | | 21 | 113 | 67 |
| 44 | TCR γ/δ | | −3825 | 1964 | 1332 | −307 | 2975 | 2283 | 40 | 94 | 67 |
| 45 | CD36L1 | SCARB1 | | 1072 | 974 | | 1600 | 2128 | 80 | 54 | 67 |
| 46 | TRA-2-49 | ALPL | | 1405 | 884 | | 1950 | 1758 | 75 | 64 | 69.5 |
| 47 | CD269 | TNFRSF17 | | 614 | 406 | | 958 | 1360 | 112 | 28 | 70 |
| 48 | CD304 | NRP1 | −80 | 283 | 275 | 54.4 | 862 | 593 | 117 | 25 | 71 |
| 49 | CD244 | SLAMF4, 2B4 | 1817 | 4008 | 3077 | 4077 | 2461 | 5676 | 4 | 139 | 71.5 |
| 50 | CD51 | ITGAV | −86.7 | 457 | 370 | −1099 | 1888 | 605 | 135 | 10 | 72.5 |

Flow Cytometry Target Validation

Protein expression of the top candidates from the screen was confirmed using separate flow cytometry analyses of mononuclear cells from AML and NBM bone marrow samples. Analyses were performed on an LSR Fortessa (BD Bioscience, USA), corresponding isotype controls were used to determine positive cells. All antibodies and reagents used are listed in Table 3.

Antibody Dependent Cellular Cytotoxicity

Antibody dependent cellular cytotoxicity (ADCC) assays were performed as previously described in Landberg et al., 2018[24]. Target cells were labeled with the membrane dye PKH26 (Sigma-Aldrich, USA) and subsequently incubated with antibodies of varying concentrations for 30 minutes. Freshly isolated or frozen NK cells from healthy donors were then added in a 10:1 ratio compared to target cells. Corresponding isotype antibodies and wells with only NK and target cells were used as controls. The ADCC effect was assessed by flow cytometry after 12-18 hours using an LSR Fortessa (BD Bioscience, USA), with the viability dye DAPI (Sigma-Aldrich, USA) and CountBright Absolute Counting Beads (Thermo Fisher Inc, USA) added to each well. Specific ADCC-induced cell death was calculated with the formula: percentage viable cells$^{antibody}$/percentage viable cells$^{no\ antibody}$, and percentage viable cell$^{isotype}$/percentage viable cells$^{no\ antibody}$ respectively.

AML Xenografts

Viably frozen mononuclear cells from bone marrow of AML patients were thawed and T cell depleted using CD3 microbead separation (Miltenyi Biotec) or OKT3 anti-CD3 antibody (BioXCell). For primary and secondary transplantations, ≥5 million cells were transplanted by tail vein injection to sublethally irradiated (250 cGy) NOD.Cg-Prkdc$^{scid}$Il2rg$^{tm1Wjl}$/SzJ-SGM3 (NSGS) mice, a variant of the NSG mouse overexpressing hGM-CSF, hIL-3 and hSCF (Jackson laboratory). Mice were euthanized upon signs of serious illness. In vivo experiments were approved by the regional Animal Ethics Committee of Malmö/Lund.

Statistical Analyses

Statistical tests were performed using Prism 6 (GraphPad Software, USA). Students T-test or Mann-Whitney U test was used when comparing two groups. Spearman's rank test was used to determine correlations between biological replicates when conducting the antibody screen.

Results

Antibody Based Screen Identifies Multiple Candidate Cell Surface Markers

To identify new cell surface markers specifically expressed on immature AML cells, an arrayed antibody screening system was used to evaluate 362 different cell surface markers within the immature $7AAD^-CD3^-CD19^-CD34^+CD38^-$ fraction of TP53 mutated AML bone marrow and NBM controls (FIGS. 1A and B). High consistency in marker expression was seen between the different biological replicates analyzed with the same iteration of the screen although the correlation co-efficient was higher for NBM samples (NBM #2 compared to NBM #3 r=0.6811, p<0.0001; FIG. 1C) than for AML samples (AML #80 compared to AML #83 r=0.647, p<0.0001; FIG. 1D). Two different ranking systems were combined to obtain a top list of the most promising cell surface markers (FIG. 1E). Markers that appeared to be specifically expressed in the $CD3^-CD19^-$ $CD34^+CD38^-$ compartment of TP53 mutated AML compared to NBM included the known markers CD123/IL3RA,[25] IL1RAP,[23] CD93,[26] CD7,[27] CD244,[28] CD56/NCAM1,[29] Jagged 2/JAG2,[30] and CD105/ENG,[31] as well as multiple new candidate markers not previously described in AML.

Flow Cytometric Validation Show Overexpression of SLAMF6 in TP53 Mutated AML Samples Based on the antibody screen, eight novel markers were chosen for further validation (FIG. 2). SLAMF6 was confirmed to be significantly overexpressed on immature $CD34^+CD38^-$ cells from primary TP53 mutated AML bone marrow compared to corresponding cells from normal bone marrow (p=0.006 comparing percent positive cells). CD54/ICAM1 also showed a trend towards higher MFI in AML compared to NBM (p=0.12 comparing median MFI). CD244, CD105/Endoglin, CD323/JAM3, and Jagged 2/JAG2 were expressed in AML but also showed a similar expression in the immature compartment of normal bone marrow. CD62E/SELE and CD369/CLEC7A expression could not be confirmed in either of the three tested AML samples.

SLAMF6 is Expressed on Immature TP53 AML Cells

To further delineate SLAMF6 expression in TP53 mutated AML, different cellular compartments were examined in AML samples with retained CD34/CD38 phenotypic hierarchies. All three TP53 mutated AML samples showed high SLAMF6 expression in the immature $CD34^+CD38^-$ compartment as compared to the more mature $CD34^-$ compartments (FIG. 3A). The opposite was seen in normal bone marrow where SLAMF6 was absent in the $CD34^+CD38^-$ HSC compartment but expressed in more mature cells, presumably B, T and NK cells (FIG. 3B). The gene expression level of SLAMF6 was also investigated in FACS sorted normal hematopoietic progenitor populations and compared to the expression levels to bulk MNC from TP53 mutated AMLs (n=18), showed a striking overexpression in the AML samples (p=0.0007 for Mann-Whitney test comparing AML to hematopoietic stem cells (HSC, n=6), FIG. 3C). All tested AML samples (n=14, Table 1) showed SLAMF6 expression on $CD3^+$ T-cells and $CD19^+$ B-cells cells independent of genetic subtype (FIG. 3D).

SLAMF6 is Expressed in AMLs of Diverse Genetic Subtypes

Given that all tested TP53 mutated AML samples showed SLAMF6 expression, the gene expression levels of SLAMF6 in MNC were investigated in the publicly available TCGA data set.[32] A higher mean expression in TP53 mutated (n=14) compared to wild type AML (n=151) was observed (p=0.001, FIG. 4A). The SLAMF6 protein expression was next examined by flow cytometry. A TP53 mutated AML sample with a CD34 negative phenotype showed high SLAMF6 expression (FIG. 4B). Three samples; AML 33, AML 34 and AML 144, showed SLAMF6 expression in their leukemic compartment (FIG. 4C). AML 33 (CD34 negative, mutations in DNMT3A, NPM1, FLT3-ITD, IDH1) showed expression in the myeloid compartment, AML 34 (CD34 positive, mutations in DNMT3A and IDH1) showed SLAMF6 expression in the myeloid as well as the more immature $CD34^+CD38^-$ compartment, and a sample with myelodysplastic syndrome MDS144 (mostly CD34 negative, mutations in RUNX1, ASXL1, TET2, and BCOR) showed expression only in a subset of the myeloid cells. Three additional samples; AML 32, MDS35 and AML 66 showed a low expression of SLAMF6 in their myeloid compartment (FIG. 4D). Four samples; AML 21, AML 28, MDS70 and AML 94 completely lacked SLAMF6 expression in their myeloid compartment (FIG. 4E). SLAMF6 was thus highly expressed in all evaluated AML samples carrying a TP53 mutation as well as in three out of ten AML samples of other genetic subtypes.

SLAMF6 Antibody Induces ADCC Mediated Killing of KG1 Cells

To evaluate SLAMF6 as a target for antibody-based therapies, a series of AML cell lines were first investigated for expression of SLAMF6. KG1 and K562 cells both expressed high levels of SLAMF6, while OCI-AML 3 showed no expression (FIG. 5A). To evaluate if SLAMF6 antibodies were able to elicit cell killing by recruiting human NK effector cells, ADCC experiments were performed using KG1 cells. As shown in FIG. 5B, a specific killing of SLAMF6 expressing KG1 cells was observed.

SLAMF6 Expression is Retained after Serial Xenografting

To establish a disease model allowing in vivo studies for antibody-based targeting of SLAMF6, primary AML samples were transplanted to sublethally irradiated NSGS mice. Three TP53 mutated AML samples were serially transplanted and two of these (AML 48 and AML 80) showed high leukemic engraftment in secondary mice. SLAMF6 expression was highly retained in both of these samples, showing the feasibility of studying SLAMF6 in vivo (FIG. 5C).

Discussion

To improve the survival of patients with neoplastic hematologic disorders (including AML), a better understanding of the disease- and relapse-causing leukemic stem cells and possibilities to specifically target such cells are needed. By identifying cell surface markers specifically expressed on AML stem cells, their prospective isolation for functional interrogation becomes feasible. Such cell surface markers may also provide attractive targets for directed treatments as shown for several markers including CD33, CD123 and IL1RAP.[9, 14, 33] Because AML is a heterogeneous disease both in terms of underlying molecular cause and response to therapy, searching for cell surface markers in specific genetic subtypes of AML might increase the chance of identifying such markers. This in turn could provide specific biological insights into AML subtypes with treatment implications in parity with ATRA treatment for t(15;17) acute promyelocytic leukemia.[34] In this study, TP53 mutated AML was a focus, which is one of the subtypes recognized by European Leukemia Net as having the worst prognosis of all AML subtypes.[35] Using an arrayed antibody screen of 362 cell surface markers, specifically upregulated markers were screened for on $CD3^-CD19^-CD34^+CD38^-$ AML cells compared to corresponding cells from normal bone marrow. Using this approach, several previously described markers were identified including CD123, IL1RAP and CD93, thus validating our screening approach. Importantly, SLAMF6 was identified as a new marker being upregulated on immature TP53 mutated AML cells and SLAMF6 antibodies were showed that can recruit human NK cells to elicit cell killing of AML cells.

SLAMF6 is one of nine members of the SLAM family of paralogue genes located on chromosome band 1q23, most of which play a role in immune regulation and some that have been suggested as therapeutic targets in different malignancies.[36] Elotuzumab is a naked antibody targeting SLAMF7 that has been shown to both mark myeloma cells for effector cell mediated killing and induce an immune response against the myeloma cells through the antibody's activating effect upon binding to normal NK cells.[37, 38] This dual mode of action immune therapy is a promising, novel treatment concept. Elotuzumab has shown promising effects in clinical trials for treatment of myeloma.[39] SLAMF6 is known to be expressed on human B, T and NK cells. Upon homophilic self-ligation of SLAMF6, internal signaling through tyrosine phosphorylation of SLAMF6 cytoplasmic tail, recruitment of SAP or EAT-2 is involved in NK cell and T cell activation.[4041] SLAMF6 also plays a role in T cell exhaustion and an anti-SLAMF6 antibody was shown to reactivate exhausted $CD8^+$ T cells, another potential antineoplastic effect that targeting SLAMF6 with an antibody could elicit.[42] However, SLAMF6 can also inhibit cellular functions through recruitment of SHP-1/2 in the absence of SAP, making the exact effects of SLAMF6 signaling or binding context- and cell-dependent.[43] In the present study, SLAMF6 was found to be upregulated in the immature $CD34^+CD38^-$ subpopulation of AML cells, which in most subtypes of AML has been shown to contain the highest AML stem cell activity as measured by long-term engraftment in immunodeficient mice.[15] Notably, SLAMF6 was not expressed on immature normal $CD34^+CD38^-$ bone marrow cells, suggesting that directed therapies against SLAMF6 would spare normal hematopoietic stem cells. SLAMF6 expression was however retained in $CD3^+$ T cells and $CD19^+$ B-cells in all AML samples analyzed, independent of genetic alterations in the AML sample. KG1 cells were also shown to express high levels of SLAMF6 and these cells were specifically killed in ADCC experiments using an anti-SLAMF6 antibody. Importantly, SLAMF6 was retained on AML cells after serial transplantation to NSGS mice.

In conclusion, SLAMF6 was identified as a cell surface marker upregulated on immature AML cells, for example those carrying a TP53 mutation. SLAMF6 was further demonstrated to provide a new target for antibody-based therapies in AML, thus opening up new avenues for the development of antibody-based therapeutic strategies for AML, including those subtypes with poor prognosis (such as TP53 mutated AML). Further, although the cell death mechanism of action demonstrated in this experiment is ADCC, the induction of cell death would be achievable with other mechanisms of action based on this finding that SLAMF6 is present on the immature AML cells. For example, SLAMF6 could be targeted with an antibody that comprises a radiolabel or cytotoxic moiety.

EXAMPLE 2

SLAMF6 Antibody Induces ADCC of AML Patient Cells

Summary

SLAMF6 antibodies can induce ADCC to kill AML patient cells.

Introduction

Killing of cancer cells through ADCC with a SLAMF6 antibody has never before been demonstrated. Here, it is demonstrated that SLAMF6-expressing primary AML patient samples and xenografted AML patient samples enriched for leukemia stem cells can be killed ex vivo by ADCC using SLAMF6 antibodies.

Materials and Methods

AML Patient Samples

Bone marrow and peripheral blood samples from AML patients were collected at the Department of Clinical Genetics, Skene University Hospital after written informed consent. Mononuclear cells were prepared by lymphoprep separation (GE Healthcare) and viably frozen. Protein expression of SLAMF6 on the leukemia cells was determined by flow cytometry with a SLAMF6 antibody (Biolegend).

Patient-Derived Xenografts

To generate patient-derived xenografts, primary AML patient cells were thawed, and T cells depleted by either CD3 microbead separation (Miltenyi Biotec) or treatment with the OKT3 anti-CD3 antibody (BioXCell). A total of ≥5 million cells were then transplanted by tail vein injection to sublethally irradiated NOD.Cg-$Prkdc^{scid}Il2rg^{tm1Wjl}$/SzJ-SGM3 (NSG-S) mice (250 cGy), a substrain of the NSG mouse overexpressing hGM-CSF, hIL-3 and hSCF (Jackson laboratory). Mice were euthanized upon signs of serious illness.

Antibody Dependent Cellular Cytotoxicity

ADCC assays were performed as described in Example 1. Target cells were labeled with the membrane dye PKH26 (Sigma-Aldrich, USA) and subsequently incubated with rabbit monoclonal SLAMF6 antibody or an isotype control (Biolegend) for 30 minutes. Freshly isolated NK cells from healthy donors were then added in a 10:1 ratio compared to target cells. Corresponding isotype antibodies and wells with only NK and target cells were used as controls. The ADCC effect was assessed by flow cytometry after 12-18 hours using an LSR Fortessa (BD Bioscience), with the viability dye DAPI (Sigma-Aldrich) and CountBright Absolute Counting Beads (Thermo Fisher Inc) added to each well.

Results

Treatment with a SLAMF6 antibody induced cell death in AML patient cells ex vivo by recruitment of NK effector cells and killing through ADCC (FIG. 6A). To enrich for leukemia stem cells by serial transplantation, patient cells from AML-83 were xenografted and passaged for two generations in vivo. ADCC was effective against both the primary AML patient cells and the leukemia stem cell-enriched patient cells. Protein expression of SLAMF6 on the surface of the patient samples was determined by FACS (FIG. 6B).

Discussion

These data show that an antibody against SLAMF6 can elicit killing of AML patient cells and of leukemia stem cell-enriched AML samples ex vivo, by binding to the target cell and recruiting effector cells to induce ADCC. This demonstrates that SLAMF6 antibodies have therapeutic activity against AML patient cells.

EXAMPLE 3

SLAMF6 expression on AML stem cells and AML cell lines

Summary

SLAMF6 is expressed on leukemic stem cells in a majority of AML patients in AML of diverse genetic background.

Introduction

To determine the relevance of SLAMF6 as a target for therapy in AML, SLAMF6 protein expression was investigated in a cohort of 42 primary AML patient samples and nine AML cell lines. The expression was further studied in the leukemic stem cell containing compartment with a $CD3^{-}CD19^{-}CD34^{+}$CD38low immunophenotype.

Materials and Methods

Bone marrow and peripheral blood samples were collected after written informed consent in accordance to the Declaration of Helsinki. Samples were collected from patients with AML and myelodysplastic syndrome (MDS). Mononuclear cells (MNC) were isolated using Lymphoprep (GE Healthcare Bio-Sciences AB, Sweden) and subsequently viably frozen. Patients included in the study and their clinical characteristics are shown in Table 5. The study was approved by a regional ethics committee in Lund (Dnr 2011/289). SLAMF6 expression was determined by flow-cytometry on an LSR Fortessa (BD Bioscience, USA) with commercially available antibodies targeting CD3, CD19, CD34, CD38 and SLAMF6 as well as a viability marker.

Results

A cohort of 42 primary AML samples was evaluated for SLAMF6 expression. For CD34 expressing AML samples, the CD34+ and the CD34+CD38low cells within the CD3−CD19− compartment known to be enriched for leukemic stem cells were specifically evaluated. Samples were classified as high ("SLAMF6high") when >50% of cells expressed SLAMF6, intermediate ("SLAMF6int") when 10-50% of cells expressed SLAMF6 and negative ("SLAMF6neg") when <10% of cells expressed SLAMF6. Within the CD3−CD19− myeloid compartment, 26% of AML samples were classified as SLAMF6high and 33% as SLAMF6int, within the CD34+ compartment 45% were classified to be SLAMF6high and 21% SLAMF6int and within the CD34+CD38low compartment 41% were SLAMF6high and 24% were SLAMF6int (FIG. 7). Further, SLAMF6 expression is not limited to one specific genetic background but is instead highly expressed in patients with a variety of different genetic alterations (FIG. 8). Furthermore, SLAMF6 is expressed in multiple AML cell lines (FIG. 9).

Discussion

SLAMF6 is shown to be aberrantly expressed on leukemic stem cells from primary AML samples carrying a large variety of genetic alterations.

TABLE 5

AML Patient Characteristics

| Pat# | Gender | Disease | FAB | ELN | Karyotype | Mutations | CD34% | Myeloid | CD34+ | CD34+ CD38low |
|---|---|---|---|---|---|---|---|---|---|---|
| 7 | F | tAML diagnosis | M4 | tAML | | IDH2, FLT3, KRAS, NPM1, WT1, DNMT3A | 1 | Int | — | — |
| 9 | F | AML diagnosis | M5 | LR | 46, XX | DNMT3A, TET2, NPM1 | 0 | Neg | — | — |
| 10 | M | sAML diagnosis | M4 | sAML | 46, XY, inv(9)(p11q12) | RUNX1, ASXL1, IDH2, JAK2, SRSF2, | 99 | Neg | Neg | Neg |
| 21 | M | AML diagnosis | M2 | IR | 46, XY | IDH2, STAG2, BCOR | 94 | Neg | Neg | Neg |
| 23 | M | AML diagnosis | M4 | LR | 46, XY, der(16)(q22) | NRAS | 46 | Int | High | High |
| 24 | M | AML diagnosis | M2 | LR | 46, XY | IDH2, NPM1, FLT3-ITD | 0 | Neg | — | — |
| 25 | M | AML diagnosis | M2 | LR | 45, X, −Y | NPM1, TET2 | 5 | Neg | — | — |
| 28 | M | sAML diagnosis | M2 | sAML | 46, XY | NPM1, FLT3-ITD, TET2 | 1 | Neg | — | — |
| 32 | M | AML diagnosis | M2 | HR | 47, XY, +13 | RUNX1, ASXL1 | 73 | Int | Int | Int |
| 33 | F | AML relapse | M4 | sAML | 46, XX | DNMT3A, NPM1, IDH1, CEBPA | 3 | High | — | — |
| 34 | F | AML diagnosis | M5 | IR | 46, XX | DNMT3A, IDH1, NRAS, CEBPA | 96 | High | High | High |
| 35 | F | MDS RAEB-2 | NA | HR | 46, XX | RUNX1, ASXL1, DNMT3A, IDH2 | 59 | Int | Int | Int |
| 37 | M | AML diagnosis | M5 | HR | Complex1 | TP53, FLT3 | 2 | Int | — | — |
| 48 | F | tAML dignosis | M2 | tAML | Complex2 | TP53 | 63 | High | High | High |
| 55 | M | tAML diagnosis | M2 | tAML | 45, XY, −7/45, X, −Y | SRSF2, ASXL1, EZH2, PTPN11 | 42 | High | High | High |
| 61 | F | AML diagnosis | M2 | LR | Complex3 | RUNX1, ASXL1, RB1 | 52 | High | High | High |
| 62 | F | AML diagnosis | M4 | HR | Complex4 | TP53, DNMT3A, | 15 | Neg | Neg | Neg |
| 66 | M | sAML diagnosis | M2 | sAML | 46, XY | IDH1, NPM1, JAK2, CEBPA | 4 | Neg | — | — |
| 70 | M | MPN/MDS | NA | NA | 46, XY | RUNX1, ASXL1, TET2 | 10 | Neg | Neg | Neg |
| 80 | M | AML diagnosis | M2 | HR | 48, XXYc, +i(12)(p10), der(17)t(13;17)(q1?4;p1?3) | TP53 | 35 | Int | High | High |

TABLE 5-continued

AML Patient Characteristics

| Pat# | Gender | Disease | FAB | ELN | Karyotype | Mutations | CD34% | Myeloid | CD34+ | CD34+ CD38low |
|---|---|---|---|---|---|---|---|---|---|---|
| 83 | M | sAML diagnosis | M2 | sAML | Complex5 | TP53, TET2, NF1 | 15 | Int | High | High |
| 85D | F | AML diagnosis | M2 | HR | Complex6 | TP53, DNMT3A | 60 | Neg | Neg | Neg |
| 85R | F | AML relapse | M2 | HR | N/A | TP53, DNMT3A | 91 | Int | Int | Int |
| 94 | M | AML diagnosis | M0 | HR | 47, XY, +10 | DNMT3A, IDH1, FLT3-ITD, RUNX1, BCOR, STAG2 | 98 | Neg | Neg | Neg |
| 97 | F | AML diagnosis | M4 | LR | 46, XX | NPM1, FLT3-ITD, IDH1, DNMT3A | 39 | Int | Int | Int |
| 104 | M | tAML diagnosis | M0 | tAML | 46, XY | NPM1, FLT3-ITD, IDH2, DNMT3A | 0 | Neg | — | — |
| 105 | F | AML diagnosis | M4 | IR | 46, XX | NPM1, FLT3-ITD, DNMT3A, | 10 | High | High | High |
| 110 | M | AML diagosis | M2 | IR | 46, XY | IDH2, SRSF2, STAG2, | 7 | Neg | — | — |
| 111 | M | sAML diagnosis | M2 | sAML | 47, XY, +8/47, XY, +mar | RUNX1, BCOR | 4 | Neg | — | — |
| 117 | M | AML diagnosis | M2 | LR | 46, XY, t(8;21)(q22;q22) | KIT, NRAS | 57 | High | High | Int |
| 123 | F | AML diagnosis | M4 | LR | 46, XX, t(16;16)(p13;q22) | — | 70 | High | High | High |
| 124 | M | AML diagnosis | M4 | LR | 46, XY, inv(16)(p13q22) | KIT | 91 | High | High | High |
| 126 | F | AML diagnosis | M1 | HR | 46, XX | IDH2, CBFC, CEBPA, RAD21, MEIS1 | 60 | Neg | Neg | Neg |
| 136 | F | AML diagnosis | M4 | LR | 46, XX | NPM1, IDH2 | 4 | High | — | — |
| 138 | M | AML diagnosis | M4 | HR | 48, XY, +13, +19 | RUNX1, TET2, ZRSR2 | 98 | Neg | Neg | Neg |
| 144 | F | MPN/MDS | NA | NA | 47, XX, +8 | RUNX1, ASXL1, TET2, BCOR | 15 | Int | Neg | Neg |
| 151 | M | sAML diagnosis | M1 | sAML | 46, XY, ?del(Y)(q11) | RUNX1, ASXL1, TET2, IDH1, SRSF2, PHF6 | 96 | Neg | Neg | Neg |
| 154 | M | tAML diagnosis | M0 | tAML | 46, XY, inv(2)(p21q31), t(3;12)(q26;p13) | RUNX1, SF3B1, NF1, PTPN11, ASXL2, IKZF1 | 20 | Int | High | High |
| 155 | M | AML diagnosis | M5 | HR | Complex7 | TP53, FLT3 | 2 | High | — | — |
| 157 | M | sAML diagnosis | M4 | sAML | 46, XY | SRSF2, NRAS | 49 | Int | Int | Int |
| 161 | F | AML diagnosis | M2 | LR | 46, XX, t(8;21)(q22;q22) | FLT3-ITD, KIT, KRAS, RUNX1 | 64 | Int | Int | Int |
| 172 | F | AML diagnosis | M4 | HR | 46, XX, t(3;12)(q26;p13) | FLT3-ITD, ASXL1, RUNX1 | 26 | Int | High | High |

Abbreviations;
sAML: secondary AML,
tAML: therapy-related AML,
ELN: European Leukemia net risk classification 2017,
LR: low risk,
IR: intermediate risk,
HR: high risk
Complex1: 47, XY, +6, +i(8)(q10), −18, −22, +mar/45-46, XY, −3, +add(6)(p21), +i(8)(q10), der(16)t(3;16)(p12;q11), −22
Complex2: 43-47, XX, del(5)(q13q33), der(8)t(8;12)(p22;p13), add(11)(p15), −12, add(13)(p11), −18, del(20)(q11), add(22)(q13), +mar
Complex3: 45, X, −X, der(8)t(8;21)(q22;q22), del(9)(q13), del(13)(q21q21), del(17)(p?13), der(21)t(8;21)ins(21;?)(q22;?)
Complex4: 46, XX, der(3)t(1;3)(p13;q27), −5, add(7)(q22), der(16)t(?5;16)(q?;p11), der(17)t(5;17)(q?;q21), der(21)t(11;21)(q13;q22), +mar
Complex5: 45, XY, der(13;14)(q10;q10)/42-44, idem, −5, −7, −9, −10, −11 , ?hsr(11)(q23), −14, −16, −20 , +4mar
Complex6: 43-49, XX, −3, add(6)(p21), −13, add(13)(q34), add(17)(p11), +2-5r/46, XX, del(5)(q13q33)
Complex7: 47, XY, +8, t(9;11)(p21;q23)/46-47, idem, der(9)del(9)(p12)del(9)(q12), der(17)t(9;17)(q31;p13)/46-47, idem, der(7;10)(q10;q10), +add(8)(p11)

EXAMPLE 4

Activation of SLAMF6 on T Cells Promotes Killing of AML Cells

Summary

Stimulation of T cells with an activating SLAMF6 antibody induces T cell-mediated killing of AML cells.

Introduction

SLAMF6 is a self-ligand, binding to other SLAMF6 molecules on the surface of interacting cells. Since SLAMF6 is expressed both on leukemia stem cells and on certain normal immune cells (e.g. T, B and NK cells), modulating these interactions could have therapeutic potential. Therefore, the effect on T cell-mediated killing of AML cells by T cell stimulation was determined with an activating SLAMF6 antibody.

Materials and Methods

T cells were isolated by CD3 microbead separation (Miltenyi Biotec) of leukocyte concentrate collected from healthy donors and viably frozen. T cell-mediated killing was assessed by incubating 80,000 T cells and 20,000 HNT-34 target cells with a SLAMF6 antibody or an isotype control (Biolegend) for 72 hours before quantification on an LSR Fortessa (BD Biosciences) with CountBright Absolute Counting Beads (Thermo Fisher) and antibodies against CD3 and CD33 (Biolegend).

Results

T cell stimulation with an activating antibody against SLAMF6 markedly increased T cell-mediated killing of AML target cells at all tested concentrations (FIG. 10).

Discussion

These data show that targeting SLAMF6 on immune cells modulates their response to leukemia and induces T cell-mediated killing of AML cells. A therapeutic agent could thus act either on AML cells, on interacting immune cells or on both cell types in combination, to elicit cell killing of leukemic cells.

EXAMPLE 5

Knockout of SLAMF6 from AML Cells Promotes T Cell-Mediated Killing

Summary

SLAMF6 protects AML cells from T cell-mediated killing. Knocking out SLAMF6 in AML cells promotes T cell expansion, activation and killing of the AML cells.

Introduction

The functional importance of SLAMF6 on AML cells was determined by knocking out SLAMF6 in AML cells by CRISPR-Cas9 and analyzing the effect on T cell-mediated killing.

Materials and Methods

SLAMF6 knockout cell lines were generated by introduction of Cas9 protein (PNA Bio) and one of two different SLAMF6 gRNA constructs, or a negative control gRNA against luciferase, by electroporation with an ECM 830 Electroporation System (Harvard Apparatus), followed by sorting of successfully transfected cells after 24 h with a FACS Aria (BD Biosciences). Knockout was verified by FACS with a SLAMF6 antibody (Biolegend) before initiation of experiments. T cells were isolated by CD3 microbead separation (Miltenyi Biotec) of leukocyte concentrate collected from healthy donors. T cell activation and T cell-mediated killing were assessed by incubation of 80,000 T cells and 20,000 target cells for 72 hours before quantification on an LSR Fortessa (BD Biosciences) with CountBright Absolute Counting Beads (Thermo Fisher) and antibodies against CD3 and CD33 (Biolegend).

Results

Removal of SLAMF6 from KG-1 AML cells by CRISPR-Cas9 (FIG. 11D) resulted in expansion and activation of interacting T cells, and increased T cell-mediated killing of the AML cells (FIG. 11A-C).

Discussion

This finding demonstrates that SLAMF6 protects leukemia cells against T cell-mediated killing and that targeting of SLAMF6 on AML cells or modulation of the SLAMF6-SLAMF6 interaction between leukemia cells and immune cells promotes an anti-leukemia immune response.

REFERENCES

1. Dombret H, Gardin C. An update of current treatments for adult acute myeloid leukemia. Blood. 2016 Jan. 7; 127 (1):53-61.
2. Stein E M, Tallman M S. Emerging therapeutic drugs for AML. Blood. 2016 Jan. 7; 127(1):71-8.
3. Estey E H. Acute myeloid leukemia: 2019 update on risk-stratification and management. Am J Hematol. 2018 Oct. 16; 93(10):1267-91.
4. Rucker F G, Schlenk R F, Bullinger L, Kayser S, Teleanu V, Kett H, et al. TP53 alterations in acute myeloid leukemia with complex karyotype correlate with specific copy number alterations, monosomal karyotype, and dismal outcome. Blood. 2012 Feb. 23; 119:2114-21.
5. Stengel A, Kern W, Haferlach T, Meggendorfer M, Fasan A, Haferlach C. The impact of TP53 mutations and TP53 deletions on survival varies between AML, ALL, MDS and CLL: an analysis of 3307 cases. Leukemia. 2017 March; 31(3):705-11.
6. Middeke J M, Herold S, Rücker-Braun E, Berdel W E, Stelljes M, Kaufmann M, et al. TP53 mutation in patients with high-risk acute myeloid leukaemia treated with allogeneic haematopoietic stem cell transplantation. Brit J Haematol. 2016 Jan. 13; 172(6):914-22.
7. Wong T N, Ramsingh G, Young A L, Miller C A, Touma W, Welch J S, et al. Role of TP53 mutations in the origin and evolution of therapy-related acute myeloid leukaemia. Nature. 2015 Feb. 16; 518(7540):552-5.
8. Jin L, Lee E M, Ramshaw H S, Busfield S J, Peoppl A G, Wilkinson L, et al. Monoclonal antibody-mediated targeting of CD123, IL-3 receptor alpha chain, eliminates human acute myeloid leukemic stem cells. Cell Stem Cell. 2009 Jul. 2; 5(1):31-42.
9. Ågerstam H, Karlsson C, Hansen N, Sandén C, Askmyr M, Palffy von S, et al. Antibodies targeting human IL1RAP (IL1R3) show therapeutic effects in xenograft models of acute myeloid leukemia. Proc Natl Acad Sci USA. 2015 Aug. 25; 112(34):10786-91.
10. Majeti R, Chao M P, Alizadeh A A, Pang W W, Jaiswal S, Gibbs K D Jr, et al. CD47 Is an Adverse Prognostic Factor and Therapeutic Antibody Target on Human Acute Myeloid Leukemia Stem Cells. Cell. 2009 Jul. 23; 138 (2):286-99.
11. Kikushige Y, Shima T, Takayanagi S-I, Urata S, Miyamoto T, Iwasaki H, et al. TIM-3 Is a Promising Target to Selectively Kill Acute Myeloid Leukemia Stem Cells. Cell Stem Cell. 2010 Dec. 3; 7(6):708-17.
12. van Rhenen A, van Dongen GAMS, Kelder A, Rombouts E J, Feller N, Moshaver B, et al. The novel AML stem cell associated antigen CLL-1 aids in discrimination between normal and leukemic stem cells. Blood. 2007 Oct. 1; 110(7):2659-66.
13. Cowan A J, Laszlo G S, Estey E H, Walter R B. Antibody-based therapy of acute myeloid leukemia with gemtuzumab ozogamicin. Front Biosci (Landmark Ed). 2013 Jun. 1; 18:1311-34.
14. Appelbaum F R, Bernstein I D. Gemtuzumab ozogamicin for acute myeloid leukemia. Blood. 2017 Nov. 30; 130(22):2373-6.
15. Thomas D, Majeti R. Biology and relevance of human acute myeloid leukemia stem cells. Blood. 2017 Mar. 23; 129(12):1577-85.
16. Radhakrishnan S V, Bhardwaj N, Luetkens T, Atanackovic D. Novel anti-myeloma immunotherapies targeting the SLAM family of receptors. OncoImmunology. 2017; 6(5):e1308618.
17. Yigit B, Wang N, Herzog R W, Terhorst C. SLAMF6 in health and disease: Implications for therapeutic targeting. Clin Immunol. 2018 Oct. 23.
18. Munitz A, Bachelet I, Fraenkel S, Katz G, Mandelboim O, Simon H-U, et al. 2B4 (CD244) Is Expressed and Functional on Human Eosinophils. J Immunol. 2004 Dec. 20; 174(1):110-8.
19. Lewis T, Olson D J, Gordon K A, Sandall S L, Miyamoto J, Westendorf L, et al. Abstract 1195: SGN-CD352A: A novel humanized anti-CD352 antibody-drug conjugate for the treatment of multiple myeloma. Cancer Res. 2016 Jul. 15; 76(14 Supplement): 1195.
20. Korver W, Singh S, Liu S, Zhao X, Yonkovich S, Sweeney A, et al. The lymphoid cell surface receptor NTB-A: a novel monoclonal antibody target for leukaemia and lymphoma therapeutics. Brit J Haematol. 2007 May; 137(4):307-18.
21. Yigit B, Halibozek P J, Chen S-S, O'Keeffe M S, Arnason J, Avigan D, et al. A combination of an anti-SLAMF6 antibody and ibrutinib efficiently abrogates expansion of chronic lymphocytic leukemia cells. Oncotarget. 2016 May 3; 7(18):26346-60.
22. Askmyr M, Agerstam H, Hansen N, Gordon S, Arvanitakis A, Rissler M, et al. Selective killing of candidate AML stem cells by antibody targeting of IL1RAP. Blood. 2013 May 2; 121(18):3709-13.
23. Barreyro L, Will B, Bartholdy B, Zhou L, Todorova T I, Stanley R F, et al. Overexpression of IL-1 receptor accessory protein in stem and progenitor cells and outcome correlation in AML and MDS. Blood. 2012 Aug. 9; 120(6):1290-8.
24. Landberg N, Palffy von S, Askmyr M, Lilljebjörn H, Sandén C, Rissler M, et al. CD36 defines primitive chronic myeloid leukemia cells less responsive to imatinib but vulnerable to antibody-based therapeutic targeting. Haematologica. 2018 March; 103(3):447-55.
25. Jordan C T, Upchurch D, Szilvassy S J, Guzman M L, Howard D S, Pettigrew A L, et al. The interleukin-3 receptor alpha chain is a unique marker for human acute myelogenous leukemia stem cells. Leukemia. 2000 October; 14(10):1777-84.
26. Iwasaki M, Liedtke M, Gentles A J, Cleary M L. CD93 Marks a Non-Quiescent Human Leukemia Stem Cell Population and Is Required for Development of MLL-Rearranged Acute Myeloid Leukemia. Cell Stem Cell. 2015 Oct. 1; 17(4):412-21.
27. Saxena A, Sheridan D P, Card R T, McPeek A M, Mewdell C C, Skinnider L F. Biologic and clinical significance of CD7 expression in acute myeloid leukemia. Am J Hematol. 1998 August; 58(4):278-84.
28. Quek L, Otto G W, Garnett C, Lhermitte L, Karamitros D, Stoilova B, et al. Genetically distinct leukemic stem cells in human CD34− acute myeloid leukemia are arrested at a hemopoietic precursor-like stage. J Exp Med. 2016 Jul. 25; 213(8):1513-35.
29. Sasca D, Szybinski J, Schüler A, Shah V, Heidelberger J, Haehnel P S, et al. NCAM1 (CD56) promotes leukemogenesis and confers drug resistance in AML. Blood. 2019 May 23; 133(21):2305-19.
30. Gal H, Amariglio N, Trakhtenbrot L, Jacob-Hirsh J, Margalit O, Avigdor A, et al. Gene expression profiles of AML derived stem cells; similarity to hematopoietic stem cells. Leukemia. 2006 December; 20(12):2147-54.
31. Dourado K M C, Baik J, Oliveira V K P, Beltrame M, Yamamoto A, Theuer C P, et al. Endoglin: a novel target for therapeutic intervention in acute leukemias revealed in xenograft mouse models. Blood. 2017 May 4; 129(18): 2526-36.
32. The Cancer Genome Atlas Research Network. Genomic and Epigenomic Landscapes of Adult De Novo Acute Myeloid Leukemia. N Engl J Med. 2013 May 30; 368 (22):2059-74.
33. Testa, Pelosi, Castelli. CD123 as a Therapeutic Target in the Treatment of Hematological Malignancies. Cancers. 2019 September; 11(9):1358-31.
34. Lo-Coco F, Avvisati G, Vignetti M, Thiede C, Orlando S M, Iacobelli S, et al. Retinoic Acid and Arsenic Trioxide for Acute Promyelocytic Leukemia. N Engl J Med. 2013 Jul. 11; 369(2):111-21.
35. Dohner H, Estey E, Grimwade D, Amadori S, Appelbaum F R, Büchner T, et al. Diagnosis and management of AML in adults: 2017 ELN recommendations from an international expert panel. Blood. 2017 Jan. 26; 129(4): 424-47.
36. Calpe S, Wang N, Romero X, Berger S B, Lanyi A, Engel P, et al. The SLAM and SAP Gene Families Control Innate and Adaptive Immune Responses. Adv Immunol. 2008. Vol. 97: 177-250.
37. Tai Y-T, Dillon M, Song W, Leiba M, Li X-F, Burger P, et al. Anti-CS1 humanized monoclonal antibody HuLuc63 inhibits myeloma cell adhesion and induces antibody-dependent cellular cytotoxicity in the bone marrow milieu. Blood. 2008 Aug. 15; 112(4):1329-37.
38. Collins S M, Bakan C E, Swartzel G D, Hofmeister C C, Efebera Y A, Kwon H, et al. Elotuzumab directly enhances NK cell cytotoxicity against myeloma via CS1 ligation: evidence for augmented NK cell function complementing ADCC. Cancer Immunol Immun. 2013 Oct. 26; 62(12):1841-9.
39. Dimopoulos M A, Dytfeld D, Grosicki S, Moreau P, Takezako N, Hori M, et al. Elotuzumab plus Pomalidomide and Dexamethasone for Multiple Myeloma. N Engl J Med. 2018 Nov. 8; 379(19):1811-22.
40. Flaig R M, Stark S, Watzl C. Cutting Edge: NTB-A Activates NK Cells via Homophilic Interaction. J Immunol. 2004 May 20; 172(11):6524-7.
41. Eissmann P, Watzl C. Molecular Analysis of NTB-A Signaling: A Role for EAT-2 in NTB-A-Mediated Activation of Human NK Cells. J Immunol. 2006 Aug. 18; 177(5):3170-7.
42. Yigit B, Wang N, Hacken ten E, Chen S-S, Bhan A K, Suarez-Fueyo A, et al. SLAMF6 as a Regulator of Exhausted CD8+ T Cells in Cancer. Cancer Immunol Res. 2019 Jul. 17:1-33.
43. Kageyama R, Cannons J L, Zhao F, Yusuf I, Lao C, Locci M, et al. The Receptor Ly108 Functions as a SAP Adaptor-Dependent On-Off Switch for T Cell Help to B Cells and NKT Cell Development. Immunity. 2012 Jun. 29; 36(6):986-1002.
44. Guo et al., 2008, Nature 453(7194):529-33
45. Plant et al., 1995, Analyt Biochem 226(2), 342-348
46. Fields & Song, Nature 340:245-246 (1989)
47. Orlandi et al, 1989. Proc. Natl. Acad. Sci. U.S.A. 86:3833-3837
48. Winter et al., 1991, Nature 349:293-299
49. Kohler et al., 1975. Nature 256:4950497
50. Kozbor et al., 1985. J. Immunol. Methods 81:31-42
51. Cote et al., 1983. Proc. Natl. Acad. Sci. USA 80:2026-2030
52. Cole et al., 1984. Mol. Cell. Biol. 62:109-120
53. Jones et al., 1986. Nature 321:522-525
54. Riechmann et al., 1988, Nature 332:323-329
55. Presta, 1992, Curr. Op. Struct. Biol. 2:593-596
56. H Zola (CRC Press, 1988) "Monoclonal Antibodies: A manual of techniques"
57. J G R Hurrell (CRC Press, 1982) "Monoclonal Hybridoma Antibodies: Techniques and Applications"
58. Harlow & Lane, 1988, "Antibodies: A Laboratory Manual", Cold Spring Harbor Laboratory, New York)
59. Hoogenboom & Winter, 1991, J. Mol. Biol. 227:381
60. Marks et al., 1991, J. Mol. Biol. 222:581

61. Cole et al., 1985, In: Monoclonal antibodies and Cancer Therapy, Alan R. Liss, pp. 77
62. Boerner et al., 1991. J. Immunol. 147:86-95
63. Skerra, Curr Opin Biotechnol. 2007 August; 18(4):295-304
64. Hoppe-Seyler & Butz, 2000, J Mol Med. 78 (8): 426-30
65. Bunka D H & Stockley P G, 2006, Nat Rev Microbiol. 4 (8): 588-96
66. Drabovich et al., 2006, Anal Chem. 78 (9): 3171-8
67. Remington's Pharmaceutical Sciences, 18th edition, A. R Gennaro, Ed., Mack Publishing Company (1990)
68. Handbook of Pharmaceutical Excipients, 3rd edition, A. Kibbe, Ed., Pharmaceutical Press (2000)
69. U.S. Pat. No. 4,235,871
70. U.S. Pat. No. 5,851,451
71. EP 0 213 303
72. Yigit et al., 2019, Cancer Immunology Research
73. Wu et al., 2016, Nature Immunology

EMBODIMENT PARAGRAPHS

Accordingly, the present application also provides aspects according to the following numbered paragraphs:

1. An agent comprising or consisting of a binding moiety with specificity for Signaling Lymphocytic Activating Molecule Family Member 6 (SLAMF6) for use in inducing cell death and/or inhibiting the growth and/or proliferation of pathological stem cells and/or progenitor cells associated with a neoplastic hematologic disorder, wherein the cells express SLAMF6.

2. An agent comprising or consisting of a binding moiety with specificity for Signaling Lymphocytic Activating Molecule Family Member 6 (SLAMF6) for use in detecting pathological stem cells and/or progenitor cells associated with a neoplastic hematologic disorder, wherein the cells express SLAMF6.

3. An agent according to paragraph 1 or paragraph 2 wherein the neoplastic hematologic disorder is a leukemia, optionally wherein
(a) the pathological stem cells are leukemic stem cells; and/or
(b) the progenitor cells are leukemic progenitor cells.

4. An agent according to any one of the preceding paragraphs wherein the cells expressing SLAMF6 also express $CD34^{+}CD38^{-}$.

5. An agent according to any one of the preceding paragraphs wherein the neoplastic hematologic disorder is associated with cells comprising a TP53 mutation.

6. An agent according to paragraph 5 wherein the cells expressing SLAMF6 also express $CD34^{+}CD38^{-}$ and wherein the cells comprise a TP53 mutation.

7. An agent according to any one of the preceding paragraphs wherein the neoplastic hematologic disorder is selected from the group consisting of chronic myeloid leukemia (CML), myeloproliferative disorders (MPD), myelodysplastic syndrome (MDS), acute lymphoblastic leukemia (ALL) and acute myeloid leukemia (AML).

8. An agent according to any one of the preceding paragraphs wherein the neoplastic hematologic disorder is acute myeloid leukemia (AML).

9. An agent according to any one of the preceding paragraphs wherein the binding moiety has specificity for human SLAMF6.

10. An agent according to any one of the preceding paragraphs wherein SLAMF6 is localised on the surface of a cell.

11. An agent according to any one of the preceding paragraphs wherein the agent is capable of modulating an interaction between an immune cell and leukemic stem cells and/or an immune cell and leukemic cells.

12. An agent according to paragraph 11 wherein the immune cells are selected from the group consisting of: B cells, T cells and/or NK cells; preferably wherein the immune cells express SLAMF6.

13. An agent according to any one of the preceding paragraphs wherein the agent is capable of killing the pathological stem cells and/or progenitor cells.

14. An agent according to paragraph 13 wherein the agent is capable of inducing apoptosis of the stem cells and/or progenitor cells.

15. An agent according to paragraph 13 or 14 wherein killing of the cells is induced by antibody-dependent cell-mediated cytotoxicity (ADCC) and/or by a T cell mediated mechanism.

16. An agent according to any one of the preceding paragraphs wherein the agent comprises or consists of a polypeptide.

17. An agent according to paragraph 16 wherein the agent comprises or consists of an antibody or an antigen-binding fragment thereof with binding specificity for SLAMF6, or a variant, fusion or derivative of said antibody or antigen-binding fragment, or a fusion of a said variant or derivative thereof, which retains the binding specificity for SLAMF6.

18. An agent according to paragraph 17 wherein the agent comprises or consists of an antibody or antigen-binding fragment thereof with binding specificity for SLAMF6.

19. An agent according to paragraph 18 wherein the agent comprises or consists of an intact antibody.

20. An agent according to paragraph 18 wherein the agent comprises or consists of an antigen-binding fragment of an antibody.

21. An agent according to paragraph 20 wherein antigen-binding fragment is selected from the group consisting of Fv fragments (e.g. single chain Fv, disulphide-bonded Fv and domain antibodies) and Fab-like fragments (e.g. Fab fragments, Fab' fragments and $F(ab)_2$ fragments).

22. An agent according to any one of paragraphs 17 to 21 wherein the antibody is a recombinant antibody.

23. An agent according to any one of paragraphs 17 to 21 wherein the antibody is a monoclonal antibody.

24. An agent according to any one of paragraphs 17 to 21 wherein the antibody is a polyclonal antibody.

25. An agent according to any one of paragraphs 17 to 24 wherein the antibody or antigen-binding fragment thereof is human or humanised.

26. An agent according to any one of paragraphs 1 to 16 wherein the agent comprises or consists of a non-immunoglobulin binding moiety.

27. An agent according to any one of paragraphs 1 to 16 wherein the agent comprises or consists of an aptamer.

28. An agent according to paragraph 27 wherein the agent comprises or consists of a peptide aptamer.

29. An agent according to paragraph 27 wherein the agent comprises or consists of a nucleic acid aptamer.

30. An agent according to any one of paragraphs 1 to 15 wherein the agent comprises or consists of a small chemical entity.

31. An agent according to any one of the preceding paragraphs further comprising a moiety for increasing the in vivo half-life of the agent.

32. An agent according to paragraph 31 wherein the moiety for increasing the in vivo half-life is selected from the group consisting of polyethylene glycol (PEG), human serum albumin, glycosylation groups, fatty acids and dextran.

33. An agent according to paragraph 31 or 32 wherein the agent is PEGylated.

34. An agent according to any one of the preceding paragraphs further comprising a cytotoxic moiety.

35. An agent according to paragraph 34 wherein the cytotoxic moiety comprises or consists of a radioisotope.

36. An agent according to paragraph 35 wherein the radioisotope is selected from the group consisting of astatine-211, bismuth-212, bismuth-213, iodine-131, yttrium-90, lutetium-177, samarium-153 and palladium-109.

37. An agent according to paragraph 34 wherein the cytotoxic moiety comprises or consists of a toxin (such as saporin or calicheamicin).

38. An agent according to paragraph 34 wherein the cytotoxic moiety comprises or consists of a chemotherapeutic agent (such as an antimetabolite).

39. An agent according to any one of the preceding paragraphs further comprising a detectable moiety.

40. An agent according to paragraph 39 wherein the detectable moiety comprises or consists of a radioisotope.

41. An agent according to paragraph 40 wherein the radioisotope is selected from the group consisting of: technetium-99m; indium-111; gallium-67; gallium-68; arsenic-72; zirconium-89; iodine-12; thallium-201.

42. An agent according to paragraph 39 wherein the detectable moiety comprises or consists of a paramagnetic isotope.

43. An agent according to paragraph 42 wherein the paramagnetic isotope is selected from the group consisting of: gadolinium-157; manganese-55, dysprosium-162, chromium-52; iron-56.

44. A pharmaceutical composition comprising an effective amount of an agent as defined in any one of the preceding paragraphs and a pharmaceutically-acceptable diluent, carrier or excipient.

45. A pharmaceutical composition according to paragraph 44 adapted for parenteral delivery.

46. A pharmaceutical composition according to paragraph 44 adapted for intravenous delivery.

47. A kit comprising an agent as defined in any one of paragraphs 1 to 43 or a pharmaceutical composition as defined in any one of paragraphs 44 to 46.

48. Use of an agent as defined in any one of paragraphs 1 to 43 in the preparation of a medicament for inducing cell death and/or inhibiting the growth and/or proliferation of pathological stem cells and/or progenitor cells associated with a neoplastic hematologic disorder, wherein the cells express SLAMF6.

49. Use of an agent as defined in any one of paragraphs 1 to 43 in the preparation of a diagnostic agent for detecting pathological stem cells and/or progenitor cells associated with a neoplastic hematologic disorder, wherein the cells express SLAMF6.

50. Use of an agent as defined in any one of paragraphs 1 to 43 for detecting pathological stem cells and/or progenitor cells associated with a neoplastic hematologic disorder, wherein the cells express SLAMF6.

51. The use according to paragraph 48, 49 or 50 wherein the neoplastic hematologic disorder is a leukemia.

52. A use according to any one of paragraphs 48 to 51 wherein the neoplastic hematologic disorder is selected from the group consisting of chronic myeloid leukemia (CML), myeloproliferative disorders (MPD), myelodysplastic syndrome (MDS), acute lymphoblastic leukemia (ALL) and acute myeloid leukemia (AML).

53. The use according to paragraph 52 wherein the neoplastic hematologic disorder is acute myeloid leukemia (AML).

54. A method for inducing cell death and/or inhibiting the growth and/or proliferation of pathological stem cells and/or progenitor cells associated with a neoplastic hematologic disorder in an individual, comprising the step of administering to the individual an effective amount of an agent as defined in any one of paragraphs 1 to 43, or a pharmaceutical composition as defined in paragraph 44 to 46, wherein the cells express SLAMF6.

55. A method according to paragraph 54 wherein the neoplastic hematologic disorder is a leukemia.

56. A method for detecting pathological stem cells and/or progenitor cells associated with neoplastic hematologic disorder in an individual, comprising the step of administering to the individual an effective amount of an agent as defined in any one of paragraphs 1 to 43, or a pharmaceutical composition as defined in paragraph 44 to 46 wherein the cells express SLAMF6.

57. An in vitro method for diagnosing or prognosing a neoplastic hematologic disorder, the method comprising:

(a) providing a bone marrow or peripheral blood sample of haematopoietic cells from an individual to be tested;

(b) isolating a subpopulation of $CD34^+$, $CD38^-$ cells from the haematopoietic cells; and (c) determining whether stem cells, contained within the $CD34^+$, $CD38^-$ cells, express the cell surface marker SLAMF6;

wherein stem cells that exhibit the cell surface marker profile $CD34^+$, $CD38^-$ and $SLAMF6^+$ are indicative of the individual having or developing leukemia optionally wherein the method also includes a step comprising quantification of levels of immune cells (such as B cells, T cells and/or NK cells), preferably wherein the immune cells express SLAMF6.

58. A method according to any one of paragraphs 54 to 57 wherein the neoplastic hematologic disorder is a leukemia.

59. A method according to any one of paragraphs 54 to 58 wherein the neoplastic hematologic disorder is selected from the group consisting of chronic myeloid leukemia (CML), myeloproliferative disorders (MPD), myelodysplastic syndrome (MDS), acute lymphoblastic leukemia (ALL) and acute myeloid leukemia (AML).

60. The method according to paragraph 59 wherein the neoplastic hematologic disorder is acute myeloid leukemia (AML).

61. An agent for use in medicine substantially as described herein with reference to the description.

62. A pharmaceutical composition substantially as described herein with reference to the description.

63. Use of an agent substantially as described herein with reference to the description.

64. A method of treatment or diagnosis as described herein with reference to the description.

65. A kit substantially as defined herein with reference to the description.

The invention claimed is:

1. A method for inducing cell death and/or inhibiting proliferation of pathological stem cells and/or progenitor cells associated with Acute Myeloid Leukemia (AML) or Myelodysplastic Syndrome (MDS) in an individual in order to treat the AML or MDS, comprising the step of administering to the individual an effective amount of an antibody or antigen-binding fragment thereof with binding specificity for Signaling Lymphocytic Activating Molecule Family Member 6 (SLAMF6), wherein the cells express SLAMF6 and are $CD34^{+}CD38^{-}$.

2. A method according to claim 1, wherein the AML or MDS is associated with cells comprising a TP53 mutation.

3. A method according to claim 1, wherein the binding moiety has specificity for human SLAMF6, and/or wherein SLAMF6 is localised on the surface of a cell.

4. A method according to claim 1, wherein the antibody or antigen-binding fragment thereof is capable of modulating an interaction between an immune cell and leukemic cells and/or an immune cell and leukemic stem cells, optionally wherein the immune cells are selected from the group consisting of: B cells, T cells and/or NK cells.

5. A method according to claim 1, wherein the antibody or antigen-binding fragment thereof:

(a) is capable of killing the pathological stem cells and/or progenitor cells, optionally by antibody-dependent cell-mediated cytotoxicity (ADCC) and/or by a T cell mediated mechanism;

(b) is capable of inducing apoptosis of the stem cells and/or progenitor cells, optionally by antibody-dependent cell-mediated cytotoxicity (ADCC) and/or by a T cell mediated mechanism.

6. A method according to claim 1, wherein the antibody or antigen-binding fragment thereof comprises or consists of:

(a) an intact antibody; or (b) an antigen-binding fragment selected from the group consisting of: Fv fragments, single chain Fv, disulphide-bonded Fv, Fab-like fragments, Fab fragments, Fab' fragments, and F (ab) 2 fragments; and/or (c) a recombinant antibody; or (d) a monoclonal antibody; or (e) a polyclonal antibody;

optionally wherein the antibody or antigen-binding fragment thereof is human or humanized.

7. A method according to claim 1, wherein the antibody or antigen-binding fragment thereof further comprises:

(a) a moiety for increasing in vivo half-life of the antibody or antigen-binding fragment thereof, optionally wherein the moiety for increasing the in vivo half-life is selected from the group consisting of polyethylene glycol (PEG), human serum albumin, glycosylation groups, fatty acids and dextran; and/or wherein the antibody or antigen-binding fragment thereof is PEGylated; and/or (b) a cytotoxic moiety, optionally wherein the cytotoxic moiety comprises or consists of a radioisotope, optionally wherein the radioisotope is selected from the group consisting of astatine-211, bismuth-212, bismuth-213, iodine-131, yttrium-90, lutetium-177, samarium-153 and palladium-109; or wherein the cytotoxic moiety comprises or consists of a toxin; and/or (c) a detectable moiety, optionally wherein the detectable moiety comprises or consists of a radioisotope, optionally wherein the radioisotope is selected from the group consisting of: technetium-99m; indium-111; gallium-67; gallium-68; arsenic-72; zirconium-89; iodine-12; thallium-201; or wherein the detectable moiety comprises or consists of a paramagnetic isotope, optionally wherein the paramagnetic isotope is selected from the group consisting of: gadolinium-157; manganese-55, dysprosium-162, chromium-52; iron-56.

8. A method according to claim 1, wherein the method is for reducing the risk of relapse in an individual with AML or MDS.

9. The method according to claim 4, wherein the immune cells express SLAMF6.

* * * * *